(12) United States Patent
Makower et al.

(10) Patent No.: US 11,911,555 B2
(45) Date of Patent: Feb. 27, 2024

(54) CELLULITE TREATMENT SYSTEM AND METHODS

(71) Applicant: REVELLE AESTHETICS, INC., Mountain View, CA (US)

(72) Inventors: Joshua Makower, Los Altos Hills, CA (US); Jonathan Podmore, San Carlos, CA (US); Earl Bright, II, Sunnyvale, CA (US); John Hanley, Manhattan Beach, CA (US); Pablo Acosta, Newark, CA (US); Theodore Ketai, Chico, CA (US); William Sauway Law, Palo Alto, CA (US); Bryan Hartley, Redwood City, CA (US)

(73) Assignee: Revelle Aesthetics, Inc., Mountain View, CA (US)

( * ) Notice: Subject to any disclaimer, the term of this patent is extended or adjusted under 35 U.S.C. 154(b) by 391 days.

(21) Appl. No.: 17/154,193

(22) Filed: Jan. 21, 2021

(65) Prior Publication Data
US 2021/0138127 A1    May 13, 2021

Related U.S. Application Data

(63) Continuation of application No. PCT/US2019/042865, filed on Jul. 22, 2019.

(60) Provisional application No. 62/798,515, filed on Jan. 30, 2019, provisional application No. 62/736,016, (Continued)

(51) Int. Cl.
*A61B 5/00* (2006.01)
*A61B 17/3207* (2006.01)
*A61M 1/00* (2006.01)
*A61M 29/02* (2006.01)

(52) U.S. Cl.
CPC .......... *A61M 1/85* (2021.05); *A61B 5/0059* (2013.01); *A61B 5/444* (2013.01); *A61B 17/32075* (2013.01); *A61M 29/02* (2013.01); *A61B 2217/005* (2013.01); *A61H 2207/00* (2013.01);
(Continued)

(58) Field of Classification Search
CPC .. A61M 1/85; A61M 29/02; A61M 2029/025; A61M 2210/04; A61M 29/00; A61B 5/444; A61B 2217/005; A61B 2017/00761; A61B 2017/00792; A61B 2017/3407; A61B 17/3403; A61B 2017/3492; A61H 2207/00
See application file for complete search history.

(56) References Cited

U.S. PATENT DOCUMENTS

| | | |
|---|---|---|
| 5,478,347 A | 12/1995 | Aranyi |
| 5,649,947 A | 7/1997 | Auerbach et al. |
| 5,728,112 A | 3/1998 | Yoon |

(Continued)

FOREIGN PATENT DOCUMENTS

| | | |
|---|---|---|
| CN | 201617909 | 11/2010 |
| CN | 202154724 | 3/2012 |

(Continued)

*Primary Examiner* — Nicholas J. Weiss
*Assistant Examiner* — Linnae E. Raymond

(57) ABSTRACT

Systems and methods for treating cellulite including an apparatus that applies or a method involving disrupting, stretching, re-orienting or tearing septa to eliminate or reduce the appearance of cellulite. In one approach, an expandable member is placed between tissue layers to stretch or tear septa connecting tissue layers between which fat deposits are contained.

7 Claims, 44 Drawing Sheets

Related U.S. Application Data filed on Sep. 25, 2018, provisional application No. 62/702,314, filed on Jul. 23, 2018.

(52) U.S. Cl.
CPC ... *A61M 2029/025* (2013.01); *A61M 2210/04* (2013.01)

(56) References Cited

U.S. PATENT DOCUMENTS

| | | | |
|---|---|---|---|
| 5,749,147 A | 5/1998 | Hasegawa | |
| 6,377,854 B1 | 4/2002 | Knowlton | |
| 7,179,272 B2* | 2/2007 | Kieturakis | A61B 17/00234 |
| | | | 606/190 |
| 7,217,265 B2 | 5/2007 | Hennings et al. | |
| 7,442,192 B2 | 10/2008 | Knowlton | |
| 7,671,423 B2 | 3/2010 | Voldman | |
| 7,871,423 B2 | 1/2011 | Livneh | |
| 8,167,280 B2 | 5/2012 | Chomas et al. | |
| 8,348,867 B2 | 1/2013 | Deem et al. | |
| 8,439,940 B2* | 5/2013 | Chomas | A61B 17/320016 |
| | | | 606/172 |
| 8,652,123 B2 | 2/2014 | Gurtner | |
| 8,979,881 B2 | 3/2015 | Clark, III | |
| 9,358,033 B2 | 6/2016 | Ballakur et al. | |
| 9,539,439 B2 | 1/2017 | Jones et al. | |
| 9,615,882 B2 | 4/2017 | Shroff et al. | |
| 9,919,168 B2 | 3/2018 | Altshuler et al. | |
| 9,974,519 B1 | 5/2018 | Schwarz et al. | |
| 10,117,892 B2 | 11/2018 | Perry | |
| 10,271,866 B2 | 4/2019 | Clark, III | |
| 2003/0130628 A1 | 7/2003 | Duffy | |
| 2003/0158566 A1 | 8/2003 | Brett | |
| 2004/0204734 A1 | 10/2004 | Wagner et al. | |
| 2004/0243159 A1 | 12/2004 | Shiuey | |
| 2004/0260210 A1 | 12/2004 | Ella et al. | |
| 2005/0251120 A1 | 11/2005 | Anderson et al. | |
| 2006/0172255 A1 | 8/2006 | Hochman et al. | |
| 2006/0241663 A1 | 10/2006 | Rice et al. | |
| 2006/0241673 A1 | 10/2006 | Zadini et al. | |
| 2007/0005091 A1* | 1/2007 | Zadini | A61B 17/32 |
| | | | 606/192 |
| 2008/0006551 A1* | 1/2008 | Tolley | A61B 17/3403 |
| | | | 206/365 |
| 2008/0015624 A1 | 1/2008 | Sonoda et al. | |
| 2008/0051627 A1* | 2/2008 | Raju | A61B 1/00082 |
| | | | 600/116 |
| 2008/0058603 A1 | 3/2008 | Edelstein et al. | |
| 2008/0109023 A1* | 5/2008 | Greer | A61B 17/320016 |
| | | | 606/170 |
| 2008/0200863 A1 | 8/2008 | Chomas et al. | |
| 2008/0275569 A1* | 11/2008 | Lesh | A61B 17/3468 |
| | | | 623/23.72 |
| 2009/0093737 A1 | 4/2009 | Chomas et al. | |
| 2009/0275899 A1 | 11/2009 | Deem et al. | |
| 2010/0057056 A1* | 3/2010 | Gurtner | A61B 17/320016 |
| | | | 606/45 |
| 2010/0106063 A1 | 4/2010 | Chomas et al. | |
| 2010/0137799 A1* | 6/2010 | Imai | A61M 5/46 |
| | | | 604/115 |
| 2010/0237163 A1 | 9/2010 | Chomas et al. | |
| 2010/0256596 A1 | 10/2010 | Chomas | |
| 2011/0028898 A1 | 2/2011 | Clark, III et al. | |
| 2011/0295297 A1 | 12/2011 | Shirley et al. | |
| 2011/0319839 A1 | 12/2011 | Del Vecchio | |
| 2012/0022510 A1 | 1/2012 | Welches et al. | |
| 2012/0150208 A1 | 6/2012 | Messmer | |
| 2013/0123771 A1 | 5/2013 | Clark, III et al. | |
| 2013/0190739 A1 | 7/2013 | Clark, III et al. | |
| 2013/0190740 A1 | 7/2013 | Clark, III et al. | |
| 2013/0197427 A1 | 8/2013 | Merchant et al. | |
| 2014/0276693 A1 | 9/2014 | Altshuler et al. | |
| 2014/0335072 A1* | 11/2014 | Hart | A61P 43/00 |
| | | | 424/94.67 |
| 2017/0172619 A1* | 6/2017 | Kirkemo | A61B 6/12 |
| 2018/0116905 A1 | 5/2018 | Capelli et al. | |
| 2018/0214169 A1 | 8/2018 | Gutwein et al. | |
| 2019/0046738 A1 | 2/2019 | Banker | |
| 2020/0046391 A1 | 2/2020 | Capelli et al. | |

FOREIGN PATENT DOCUMENTS

| | | | |
|---|---|---|---|
| CN | 202821527 | 3/2013 | |
| CN | 204191319 | 3/2015 | |
| CN | 104644244 | 5/2015 | |
| CN | 204500879 | 7/2015 | |
| EP | 2504047 | 10/2012 | |
| GB | 2350080 A | 11/2000 | |
| WO | WO-2016040820 A1 * | 3/2016 | ......... A61B 1/00183 |
| WO | WO2019060924 | 3/2019 | |

* cited by examiner

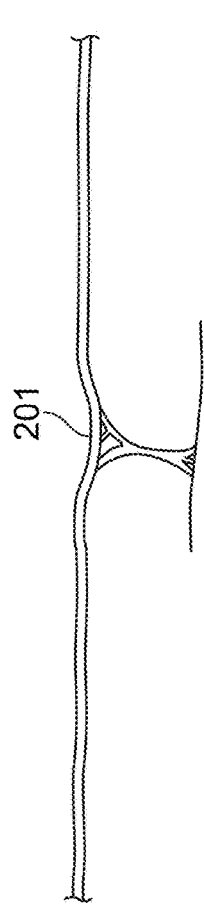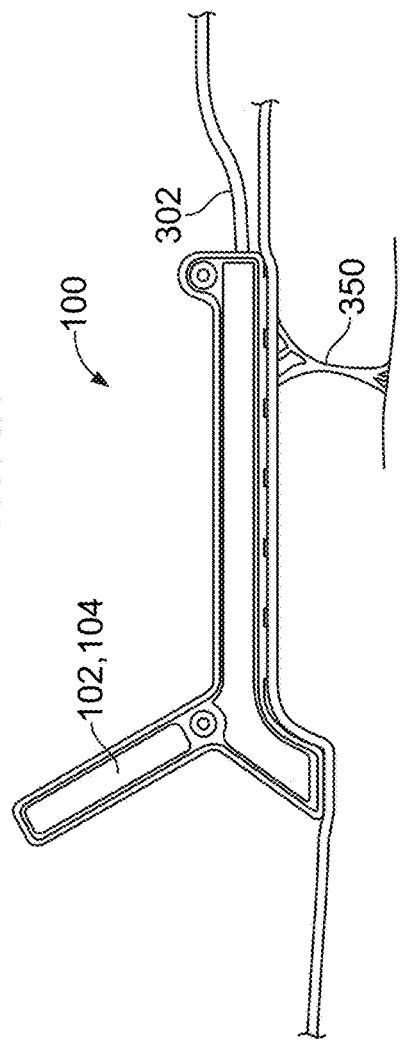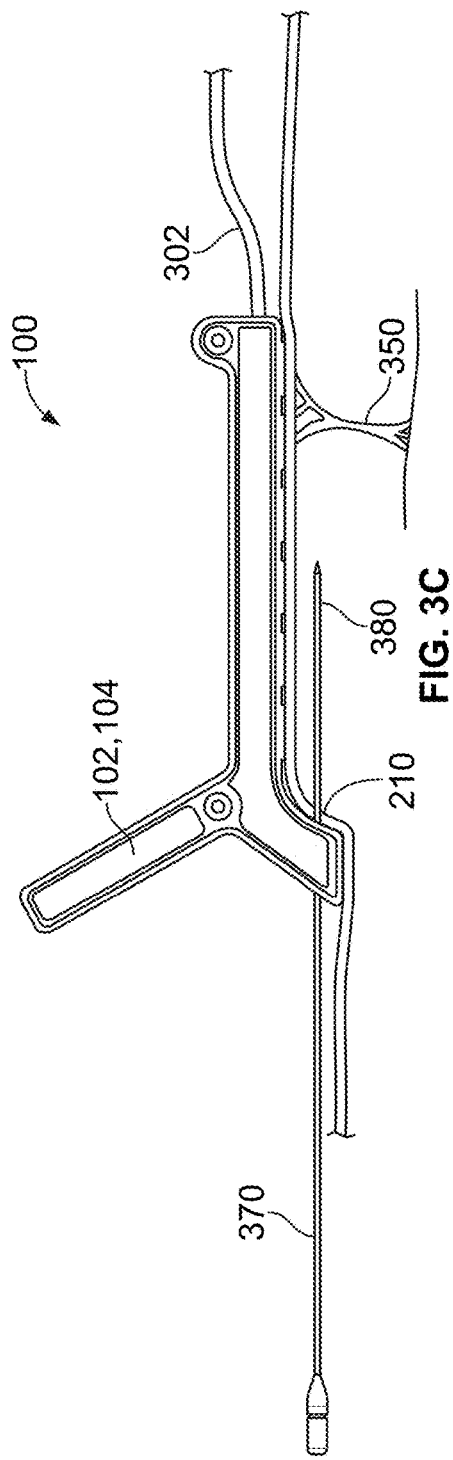

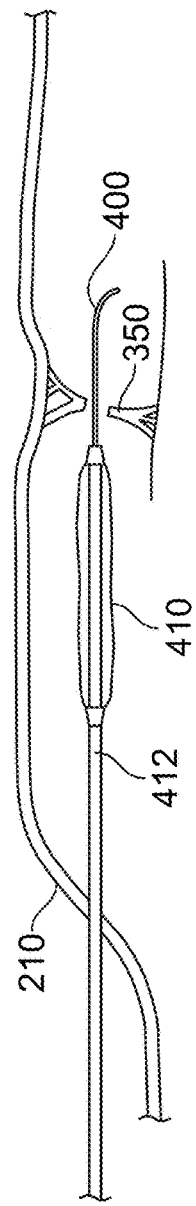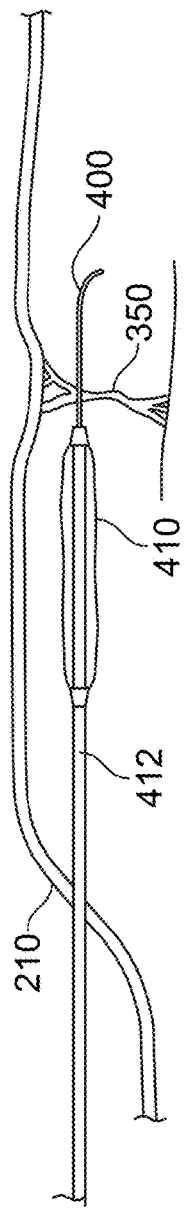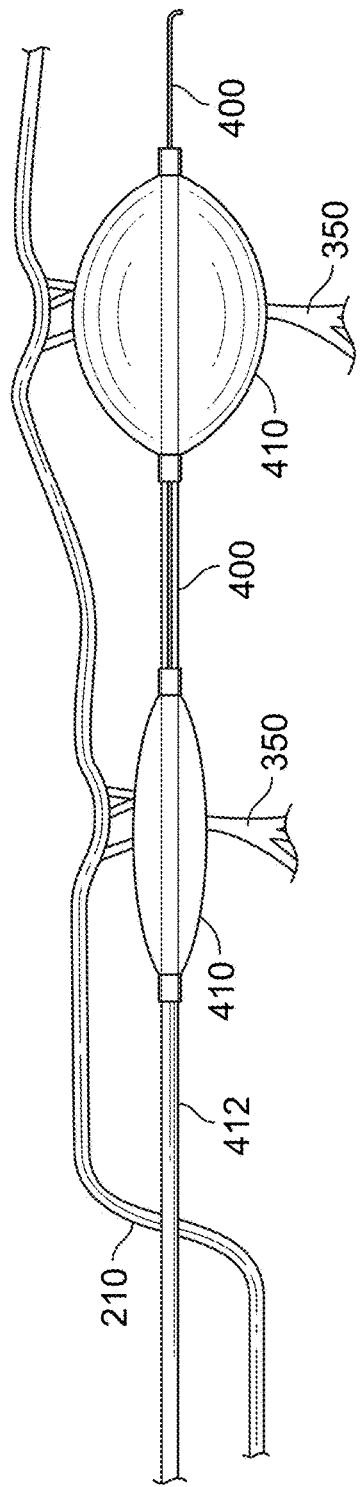

FIG. 4A  FIG. 4B

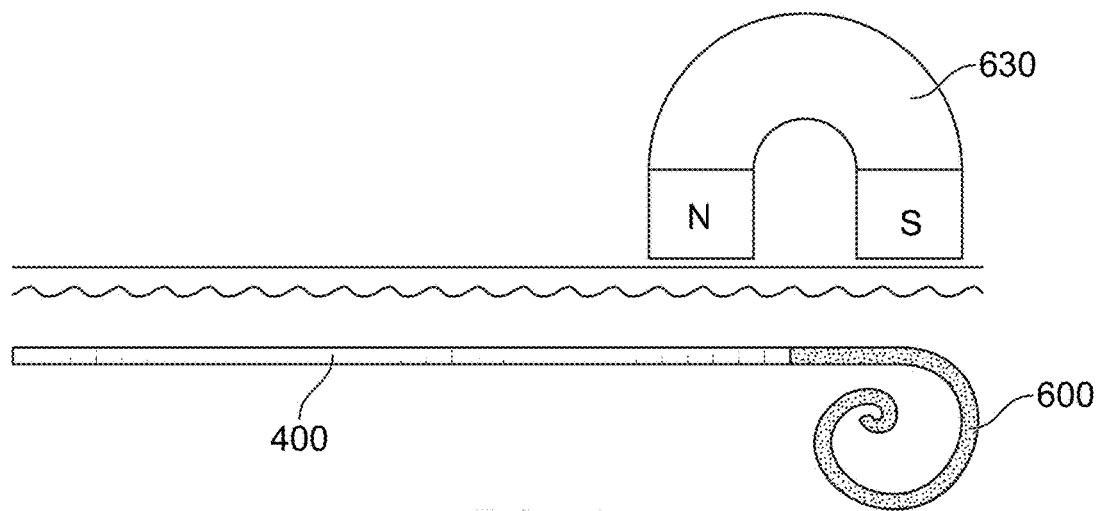
FIG. 5J
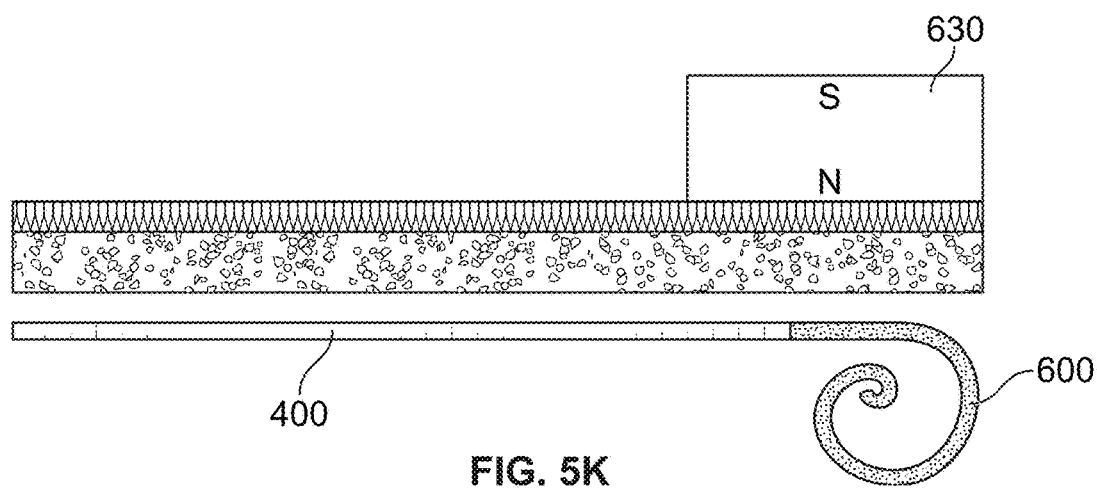
FIG. 5K
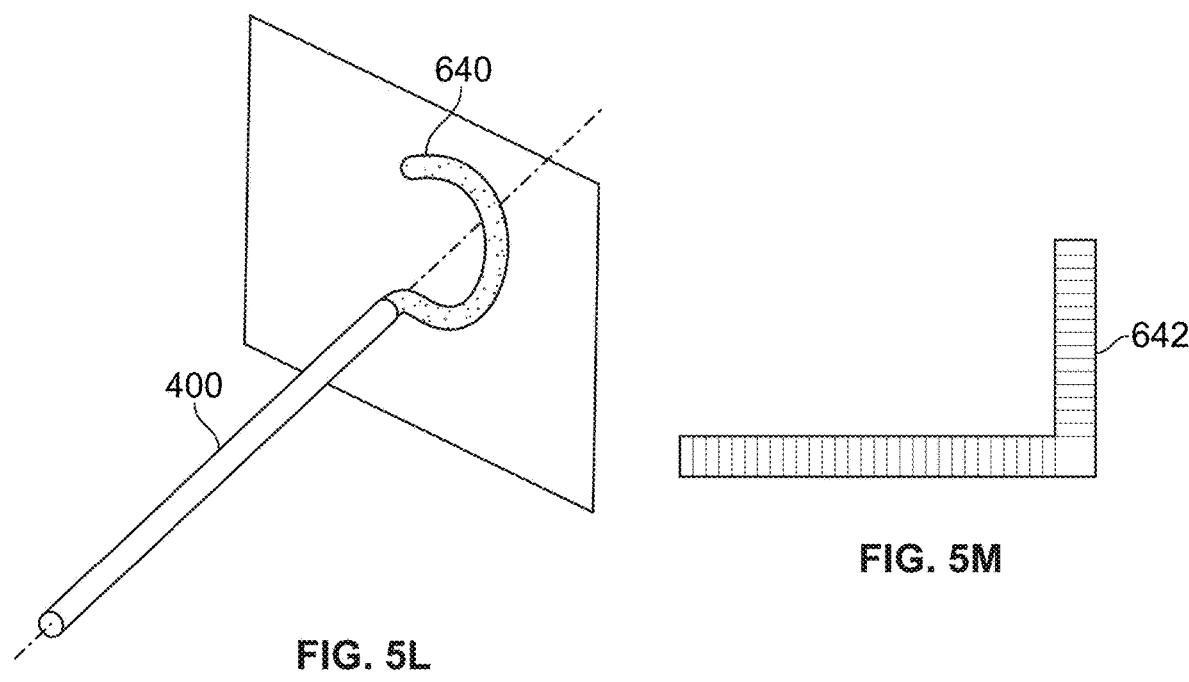
FIG. 5L
FIG. 5M

CELLULITE TREATMENT SYSTEM AND METHODS

The present disclosure generally relates to systems and methods for treating cellulite. This application claims the benefit and priority of PCT/US19/42865, filed Jul. 22, 2019 and U.S. Patent Application Nos. 62/702,314 filed Jul. 23, 2018; 62/736,016 filed Sep. 25, 2018; and 62/798,515 filed Jan. 30, 2019, the entirety of the contents of which are hereby incorporated by reference.

FIELD OF THE DISCLOSURE

Background of the Disclosure

There is a continuing need for an effective and atraumatic approach to treating cellulite, also known as gynoid lipodystrophy, nodular liposclerosis, edematofibrosclerotic panniculopathy, panniculosis, adiposis edematosa, demopanniculosis deformans or status protrusus cutis. Moreover, there is a need for proactive treatment modalities that prevent future or reoccurrence of cellulite and which are easy and effective to use.

It has been reported that more than 85% of women have cellulite thus suggesting that cellulite is a physiologic rather than pathologic condition. The existence of fat in the reticular dermis alone is not thought to cause cellulite. Cellulite can be described as the herniation of subcutaneous fat within fibrous connective tissue that is expressed as dimpling of the skin. This fat loading can lead to stress on connective tissue located between fat lobulas. Such dimpling is more common in women than men due to the orientation of subcutaneous fibrous structures defining chambers containing fat cells. In fact, it is this structure that is believed to cause the appearance of cellulite more than being overweight. Often, cellulite appears on the pelvic region including the buttocks, lower limbs and abdomen.

Subdermal fat layers below the epidermis are contained between dermal layers connected by septa which act as connective tissue between the dermal layers. In men, the septa are arranged more randomly and densely oriented in a more criss-crossed configuration while the septa in women are generally more parallel in arrangement. Also, men have thicker dermis and more angled septa relative to the skin surface whereas women have relatively thinner dermis which thins with age, and septa that are perpendicular to the skin surface. Moreover, women with cellulite have exhibited thickening of the septa in the regions of cellulite and tensioning of septa highlights cellulite. In women, fat storage in adipose tissue has a biological purpose in that it is maximized ensuring adequate caloric availability for pregnancy and lactation. An increase in fluid retention or proliferation of adipose tissue in such subdermal fat layers can further result in the appearance of cellulite where the septa is maintaining a first distance between dermal layers, thus creating dimples, whereas pockets between septa bulge. Over time, the septa may stretch, then eventually contract and harden thus retaining tissue layers at fixed distances, but pockets between such septa may be expanded thus adding to the appearance of cellulite.

Various approaches have been taken to treat or address cellulite. Early treatments involved attempts at increasing circulation and fat oxidation in areas exhibiting cellulite. Here, substances such as hyaluronic acid and aminophylline were injected in the target areas to reduce cellulite. Other approaches involved electroporating the target areas followed by the application of mesotherapy, or applying dermatological creams or other supplements to cellulite. These approaches could be supplemented by massage or massage was used alone for the purpose of promoting increased fat reabsorption or drainage of fluids and toxins in the treated areas. Ultrasound has also been proposed to disrupt subcutaneous tissues and fat and has been used in combination with liposuction. Low acoustic pressure in combination with the infiltration of microbubbles has also been employed to reduce the appearance of cellulite, as has the use of other energies such as lasers and radio frequency. Such approaches have been characterized by limited or unpredictable results. More recently, the cutting of septa with blades or needles in the subdermal region has been employed. This approach, however, has been found to be labor intensive and very traumatic to the tissue leading to bleeding, bruising, tough tissue nodules, long, painful recoveries and inconsistent results.

An attempted approach at a less traumatic cellulite treatment has been described in Altshuler et al. (US2011/0046523A1) in which the objective is to stretch rather than cut the septa. In order to minimize the stretching force needed for eliminating the appearance of cellulite, the approach utilizes heating of the septa and fascia tissue adjacent to the fat tissue to a sufficient temperature for a sufficient amount of time to achieve lasting elongation of the septa. By increasing the temperature of the connective tissue to be treated with a stretching force, the amount of force required to improve the length of (e.g., elongate) the connective tissue is reduced. Altshuler et al. states in this way negative side effects to the body area being treated including tearing, bruising and pain can be reduced and/or avoided. Altshuler et al. also states it is believed that similar improvement of the appearance of cellulite may be achieved by exposing at least one of the fascia and/or the septa to a relatively cold temperature and a stretching force for a sufficient amount of time to achieve lasting elongation of the septa and/or the fascia in order to fracture the septa and/or the fascia, both elongation and fraction are believed to improve cellulite appearance. In order to perform the treatments of Altshuler et al., measurement and control of the temperature of the septa and fascia have to be taken and maintained in addition to controlling the stretching force.

Accordingly, there is a need for atraumatic, effective and efficient approaches to treating, minimizing or eliminating cellulite with simple systems. These approaches should be associated with predictable results and be relatively easy to employ.

The present disclosure addresses these and other needs.

SUMMARY OF THE DISCLOSURE

Briefly and in general terms, the present disclosure is directed towards atraumatic cellulite treatment systems and methods that minimize tissue trauma, reduce and/or eliminate bleeding and bruising. The system includes an apparatus that facilitates and methods involving re-orienting, tearing, and/or stretching of septum or septa in a location of cellulite. In one aspect, the treatment approach involves a focal balloon contouring system.

In one embodiment, a cellulite treatment stabilizer is provided and configured with a plurality of suction ports arranged to stabilize tissue and includes a proximal, lower portion defining tissue engagement structure arranged to facilitate creating a tissue insertion site. In one approach, a downward application of pressure facilitates the creation of a tissue insertion site.

In another embodiment, a cellulite treatment stabilizer additionally or alternatively includes a plurality of channels for receiving cellulite treatment instrumentation. In one aspect, the channels are arranged to facilitate access to a plurality of tissue depths.

In a further embodiment, a cellulite treatment stabilizer is configured to be generally or approximately arranged in a parallel fashion, along a common plane or in a similar direction with a balloon on a shaft configured to be advanced between tissue layers, the stabilizer including structure configured to extend longitudinally along the outside of the skin and a lower proximal portion configured to create a tissue insertion site.

In yet a further embodiment, an elongate cellulite treatment stabilizer is provided and configured to be arranged in a parallel fashion, along a common plane or similarly directed with a balloon on a shaft configured to be placed between tissue layers, a lower surface of the stabilizer is configured with friction structure for engaging and stabilizing tissue.

In another embodiment, a cellulite treatment balloon is mounted on a stiff shaft and is sized and shaped to be advanced between tissue layers and is used in combination with a parallel arranged or similarly directed stabilizer that stabilizes tissue during balloon advancement. In one approach, the stabilizer is configured to be removed once the balloon is placed at a treatment site before treatment.

In one particular aspect, fibrous septa that connect superior and inferior fascia plateaus within skin can be crossed with a dilator using one or more of an array of tools, such as a needle, guidewire, expandable members, balloon devices, to stretch, tear, or re-orient septum or the septa. By doing so, the target subcutaneous connective tissue associated with the surface defect can be directly modified with minimal impact to surrounding blood vessels, lymphatic system and fat can be more evenly distributed and skin can assume a smoother appearance in an atraumatic manner. In one method, anesthetic is injected into the treatment site transcutaneously or subcutaneously, stabilization and/or retraction force is applied to the target skin to create a stabilized surface, an introducer tube and/or wire is inserted subcutaneously across the treatment site, stabilization and/or retraction force is released, and an expandable member is placed subcutaneously at the treatment site and is expanded, and expanded repeatedly as necessary. Remote imaging or ultrasonic or fluoroscopic energy can be employed to observe the procedure. A resizing or alternative configuration of the dilator or expandable member and additional expansion can be employed to complete the treatment of a particular area. The treatment device is then repositioned to treat additional areas. The treatment device can be configured to treat a plurality of areas simultaneously or in succession without repositioning or a spot treatment approach can be taken. Langer lines can be employed as a reference to direct treatment. Additionally, through one or more entry points, various treatment trajectories and expansion areas are directed and in certain applications a steerable introducer is used to access treatment areas. Further, anti-inflammatory, collagenase, deoxycholic acid, salicylic acid, glycolic acid, hyaluronic acid or cellulite treatment medicants can be employed at the interventional site separately or directly by an expandable dilator or other procedural instrumentation.

In one particular embodiment, the system includes one or more generally elongate suction stabilizers configured, sized and shaped to cooperatively provide and create a stable insertion site and controlled depth, and includes an access needle, an introducer tube and/or a guidewire and an expandable member attached to an elongate member associated with each or a single stabilizer. The suction stabilizer includes a plurality of ports configured to apply suction to a patient's skin to create a stabilizing surface and includes one or more guide channels through which instrumentation is configured for insertion subcutaneously at the treatment site. In another approach, the guide channel can be adjustable and lockable in various locations to set the location or depth of insertion into skin. Moreover, the stabilizer can employ other mechanical approaches to adhering to tissue such as adhesive or pinching or rolling structures.

In various aspects of atraumatic treatment, the dilator is a balloon available in various sizes, number and shapes, a balloon on a needle defining a single assembly, a balloon with stiff members on its surface for enhancing localized force, an expandable cage, a mechanistically expandable dilator, dual balloons configured for expanding tissue on opposite sides of septum, a resorbable stent, resorbable filler material, patient's own fat harvested from another location, permanent fillers or spacers, or in a more traumatic embodiment, structure including a rotating structure or blade. In other aspects of slightly more traumatic embodiments, the expandable member can be replaced with or additionally include a cutting balloon or harmonic scalpel, selective cautery structure or energy transmitting structure for dissecting tissue and/or controlling bleeding.

The cellulite treatment system also involves in certain approaches, a bright light configured at or emitted through a tip of treatment structure or placed along or at strategic locations along treatment structure for the purpose of locating intra-dermal structures at the interventional site. In this way, direct observation of the treatment device by transillumination through the skin is provided and positioning and performance thereof subcutaneously is readily available to an operator.

In a further embodiment, means for anchoring a distal end or tip of the interventional device is provided to provide a rail during exchange of devices and other movements along and within the interventional site for therapy delivery. Accordingly, one or more of a coil, magnets, hook or hooks and other structure are configured to stabilize instrumentation.

Moreover, objective measurement devices are included in the treatment system to assess the results of therapy. In one approach, laser light energy such as bright light or laser light is emitted and received by the measurement device and surfaces of treated areas is scanned. The measurement device creates a complete three-dimensional map of all cellulite relative to normal skin. By comparing improvement of volume of divots versus normal idealized surfaces, the operator can calculate total and local volume benefits of therapy and track improvement over time.

Additionally, the dilator approach to creating spaces subcutaneously have applications to treating other conditions or maladies. For example, the disclosed dilators are employed for body sculpting, eliminating wrinkles, treating acne scars and/or lifting and repositioning skin. Foam fillers or spacers of varying lengths and other structures such as subcutaneous attachment structures that are absorbable or permanent are used to accomplish such objectives.

These and other features of the disclosure will become apparent to those persons skilled in the art upon reading the details of the systems and methods as more fully described below.

BRIEF DESCRIPTION OF THE DRAWINGS

FIG. 1R is a partial cross-sectional side view, depicting a dilator cover.

FIGS. 3A-L are cross-sectional views, depicting various aspects of a cellulite treatment procedure.

FIGS. 4A-C are longitudinal views, depicting connecting tissue before and after treatment.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described.

It must be noted that as used herein and in the appended claims, the singular forms "a", "an", and "the" include plural referents unless the context clearly dictates otherwise. Thus, for example, reference to "the system" includes reference to one or more systems and equivalents thereof known to those skilled in the art, and so forth.

Figure 1A:
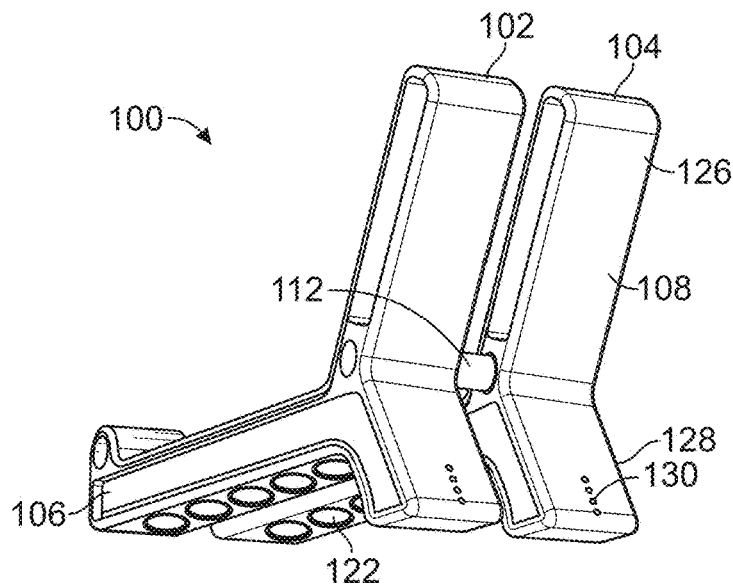
FIGS. 1A-H are various views, depicting a stabilizer configured to facilitate creation of an entry site into skin.
Figure 1B:
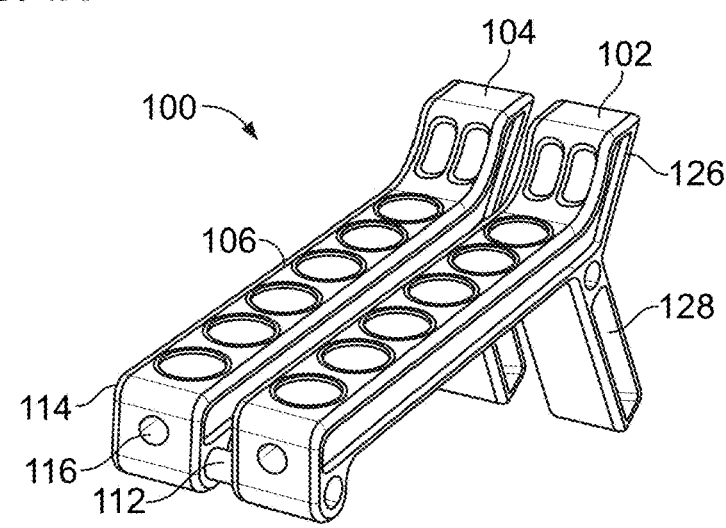
Figure 1C:
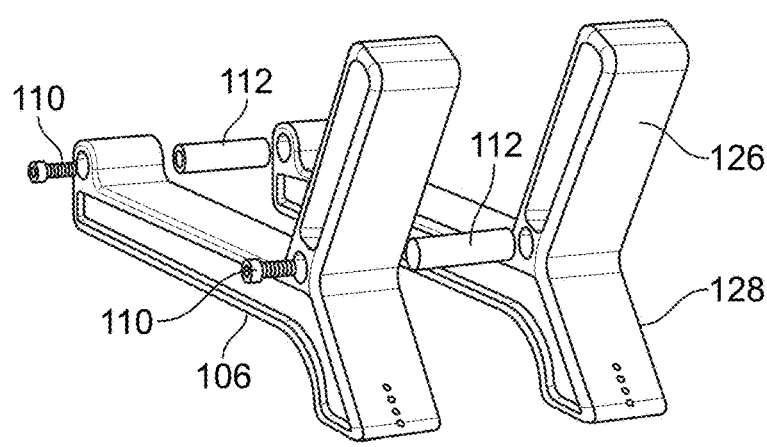
Figure 1D:
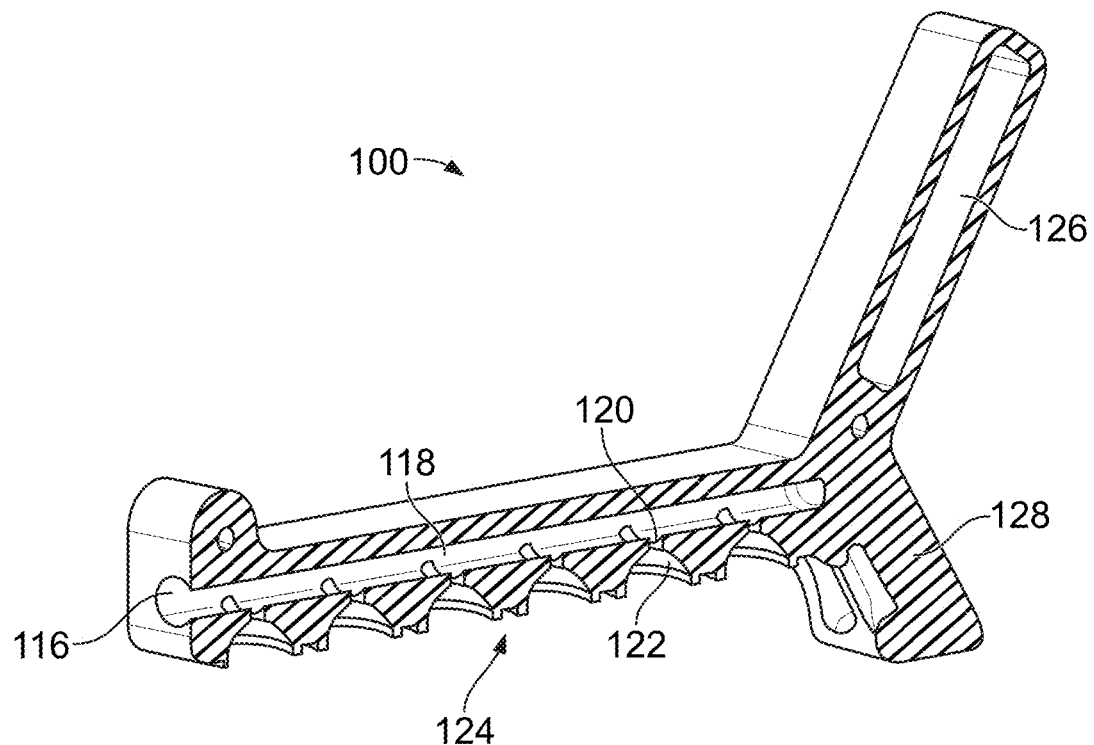
Figure 1E:
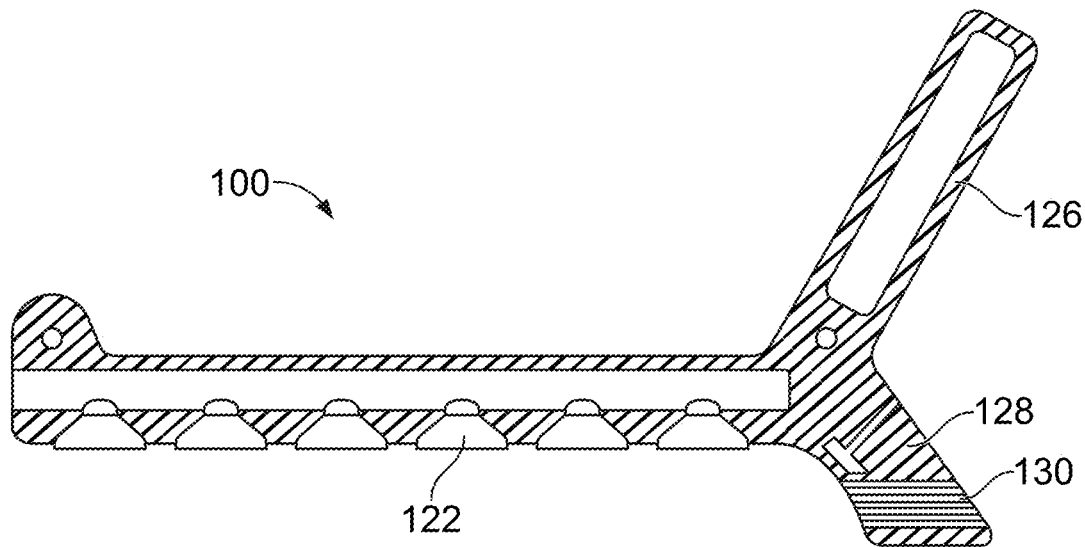

With reference to FIGS. 1A-E, there are shown various views of one approach to a stabilizer assembly 100 for a focal balloon contouring system. In addition to the stabilizer assembly, as described below, the focal balloon contouring system includes one or more of suction tubing, a trocar needle, a guidewire, an introducer, an inflation device and a balloon catheter or dilator. The stabilizer assembly includes first 102 and second 104 stabilizer bodies defining elongate structures 106 extending from a handle portion 108. The stabilizer bodies 102, 104 are arranged in a parallel fashion and are attached at two points by screws 110. Spacers 112 are further provided to maintain the parallel positioning of the stabilizer bodies 102, 104. Formed in a terminal end 114 of each elongate portion 106 is an opening 116 in communication with an elongate chamber 118 extending within the elongate portion 106. As best seen in FIG. 1D, the chamber 118 includes a plurality of downwardly directed lateral openings 120 that expand to define generally cone or cup-shaped cavities 122 directed towards a lower surface 124 of the elongate portion 106. The lower surface has a dimension ranging from about 5 cm to 24 cm, preferably 10 cm. A suction force is applied through the terminal end opening 116 and cavities 122 to provide a stabilization and/or retraction force that can be applied to a treatment side so that a stable platform is created to insert an interventional device within tissue. In one approach, suction force is provided by a suction or vacuum pump. In an alternative approach, suction and or a vacuum is provided by a syringe or alternatively by a cam-based structure involving pulling a lever such as in a cam-based suction cup.

In use, the stabilizer 100 adheres to the skin to create a stable plane of intervention at a fixed distance below the skin level for inserting interventional devices within tissue. The stabilizer adhering to the skin holds it and creates a counterforce while the skin is pierced and the treatment tools are advanced subcutaneously to the desired location. In certain embodiments, the stabilization and/or retraction force can be used to lift or position tissue to create a stable insertion site without pulling the tissue into a cavity or recess. In alternative approaches, the system can include a single stabilizer body or guiding structure between the two stabilizer bodies for the insertion of instrumentation. Further, a patch or film can first be applied to flatten skin prior to employing the stabilizer, the patch or film providing a surface against which a more even and consistent suction can be applied.

Figure 1F:
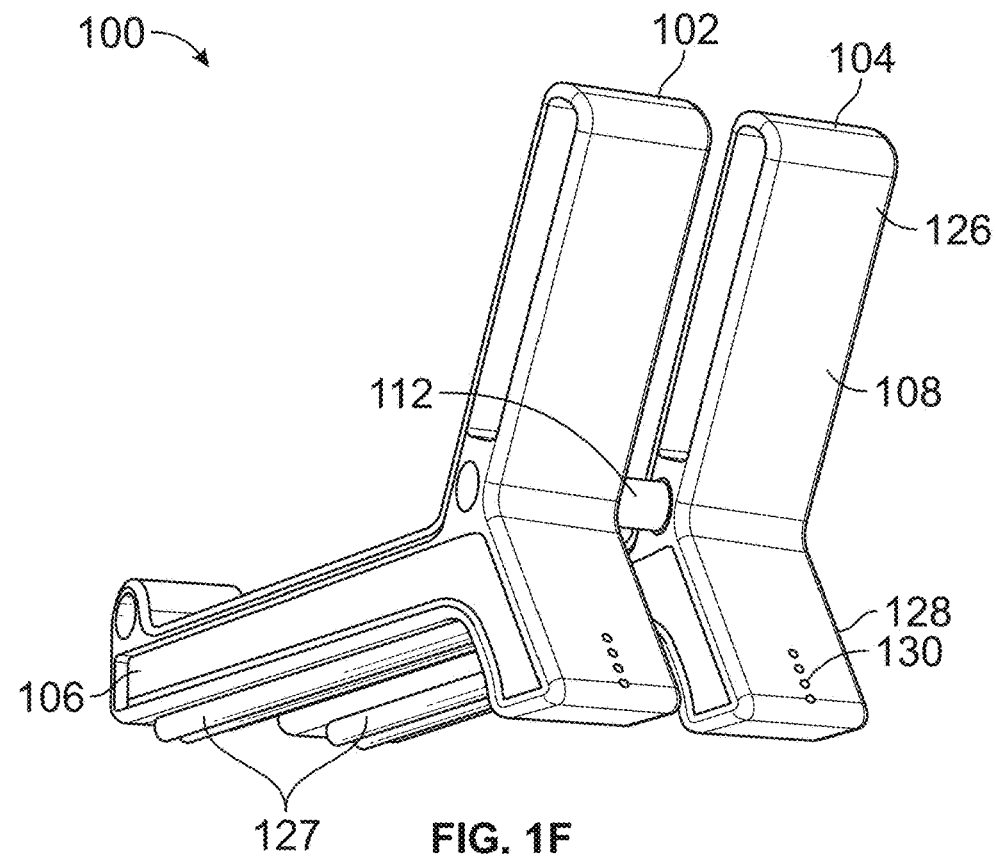
Figure 1G:
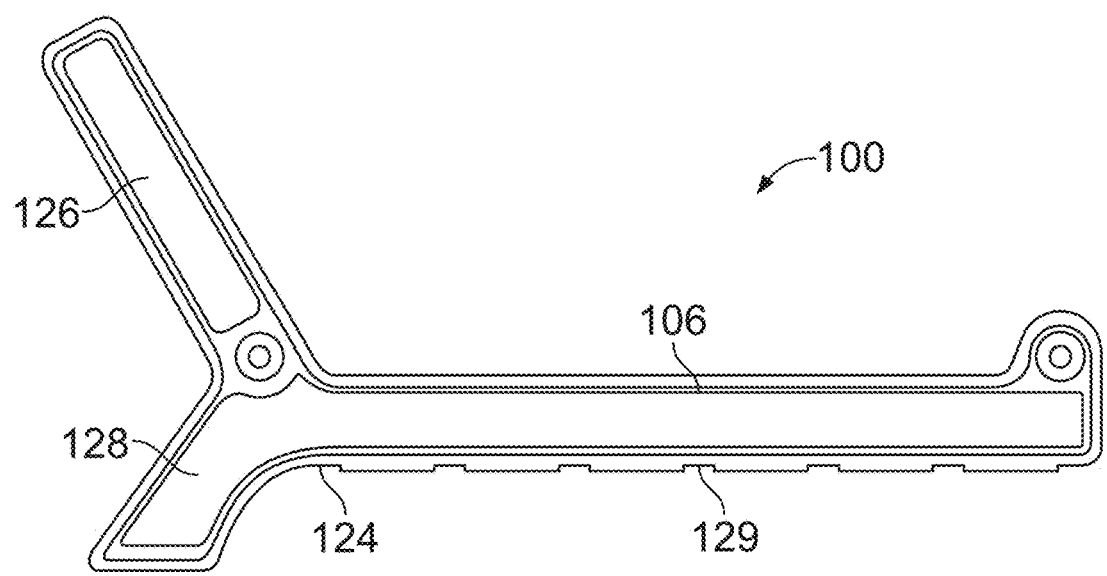
Figure 1H:
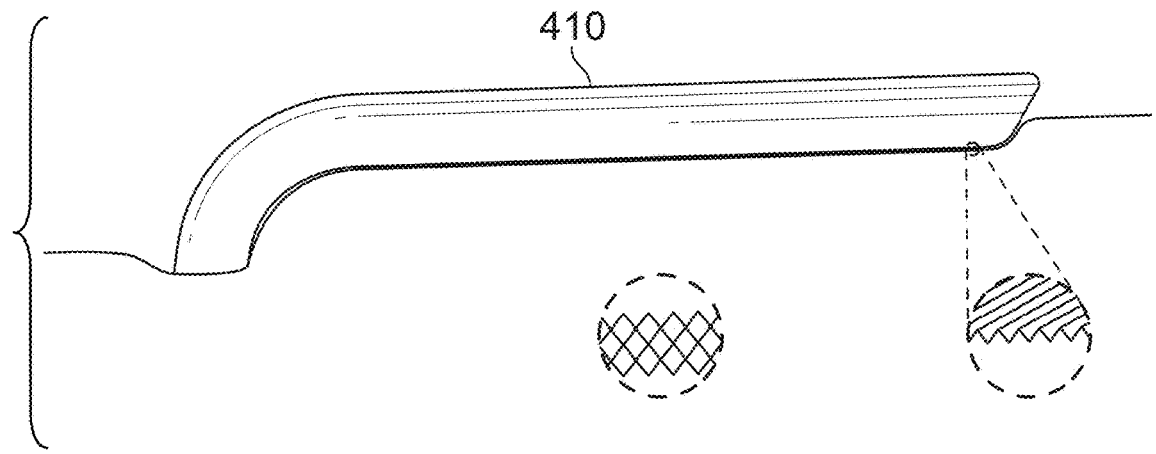

In one or more embodiments, the stabilizer assembly is used to guide the initial device or guidewire into place and is then removable, allowing for the impact of the therapy to be observed directly in real time at the skin level without distortion from suction and it outlays a path along which a single device or sequence of devices can be used to intervene on one or more lesion areas. Moreover, the stabilizer assembly does not create large areas of suction into which blood can be pooled creating large regions of bruising or tissue damage and it facilitates a reduced number of entry points, perhaps a single entry, to access multiple regions across a wide area of skin Additionally, various other structure can be employed to adhere to tissue to create a stable insertion site such as adhesive or double-sided adhesive strips attached to tissue that are engaged by the underside of the stabilizer or pinching or rolling structures which are configured to grip tissue. In one particular approach, as shown in FIG. 1F, a stabilizer can include rollers 127 configured to grasp and retain structure for the purpose of stabilization of an interventional site. Additionally, adhesive 129 (FIG. 1G) is applied to the lower surface 124 of the elongate portion 106 and when placed into engagement with tissue, the adhesive 129 adheres to the tissue thereby providing necessary force for holding the tissue. Such approaches can be used in addition to or in replace of employing suction force. In yet another approach (See FIG. 1H), the stabilizer 100 is simply placed against tissue and a pressure is applied rather than employing suction as a component of stabilization. To aid in the engagement between the stabilizer 100 and tissue, the bottom surface of the stabilizer 100 can be knurled or rough textured. In another aspect, a sticky mat material can be configured along at least a portion or the entirety of the bottom surface of the stabilizer. Moreover, structure associated with providing suction can be omitted from the stabilizer thus simplifying its design.

The handle portion 108 includes an upper portion 126 and a lower portion 128. The upper handle portion 126 (not shown in FIG. 1H) is sized and shaped to be grasped by hand for device manipulation. The lower handle portion 128 includes a series of channels 130 that are parallel and spaced vertically in the lower handle portion 128. These channels 130 are sized and shaped to slidingly receive interventional treatment instrumentation. It has been noted that an optimal interventional treatment site is in the range of 6-10 mm below the surface of the skin. Thus, the channels 130 are arranged to introduce instrumentation between tissue layers within that range.

Figure 1I:
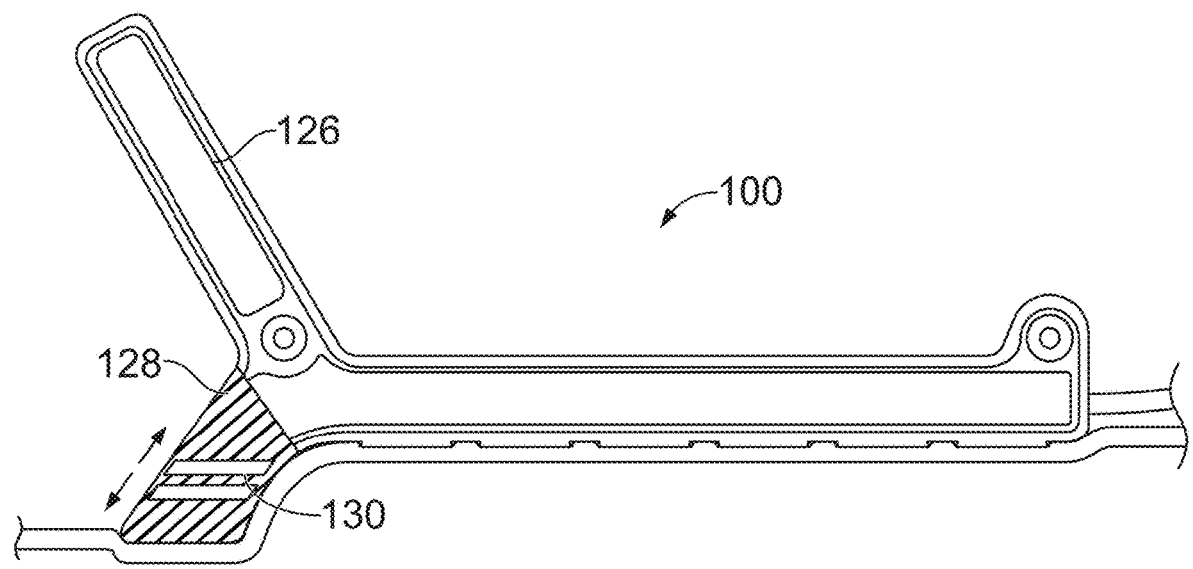
FIGS. 1I-K are enlarged views, depicting the structure of cavities formed in a stabilizer.

In an alternative approach (FIG. 1I), rather than having multiple parallel channels 130, the lower handle portion 128 is equipped with a single channel or a plurality of channels that is or are translatable and lockable at desired positions. Also, the number of channels can be reduced in number or include only a single channel and/or the channel or channels can be enlarged so that they can receive a dilator assembly. Thus, the stabilizer can remain in place while a dilator and/or balloon catheter is advanced to and from an interventional site. Moreover, the channels can include threads and outer portions of the various devices intended to be advanced through the channels can include corresponding threaded structure to thereby provide a more controlled advancement and withdrawal of parts through the channels. Accordingly, it is also to be recognized that structure of the stabilization device itself, such as the lower portion 128 of the handle 108 can be employed to create an indentation in skin and a path to create an insertion site by inserting tooling through the channels 130 formed in the handle 108.

Figure 1J:
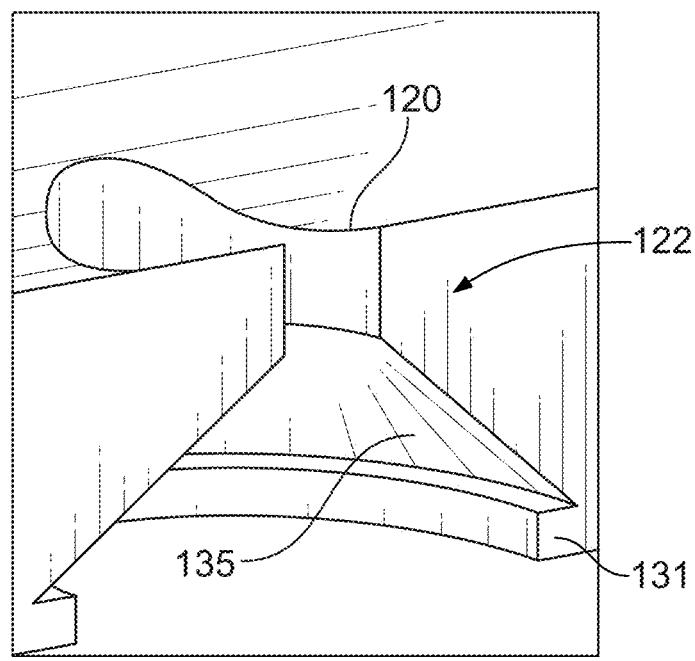
Figure 1K:
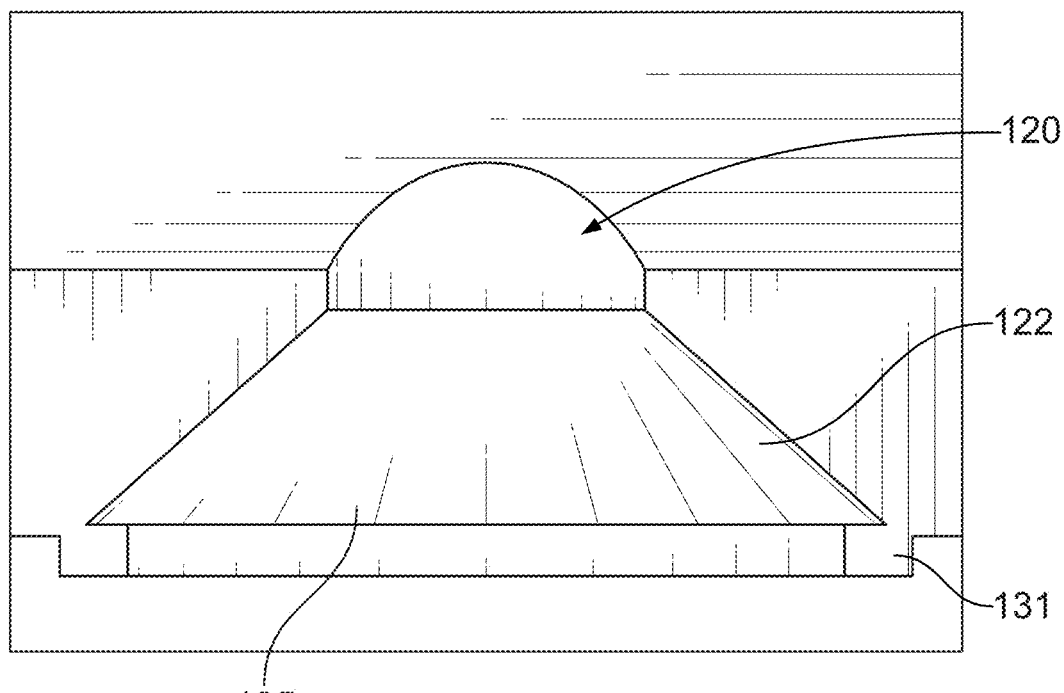
Figure 1L:
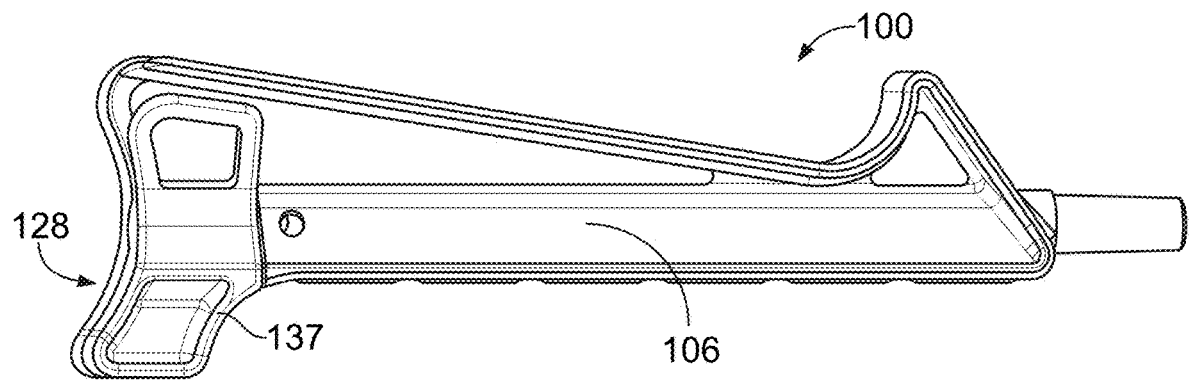
FIGS. 1L-P are various views, depicting details of an alternative embodiment of a stabilizer.
Figure 1M:
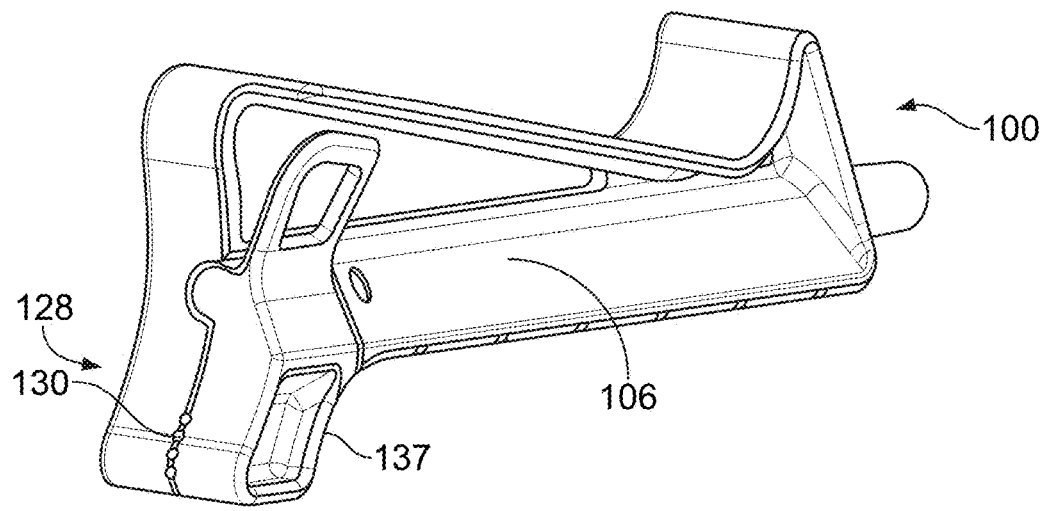
Figure 1N:
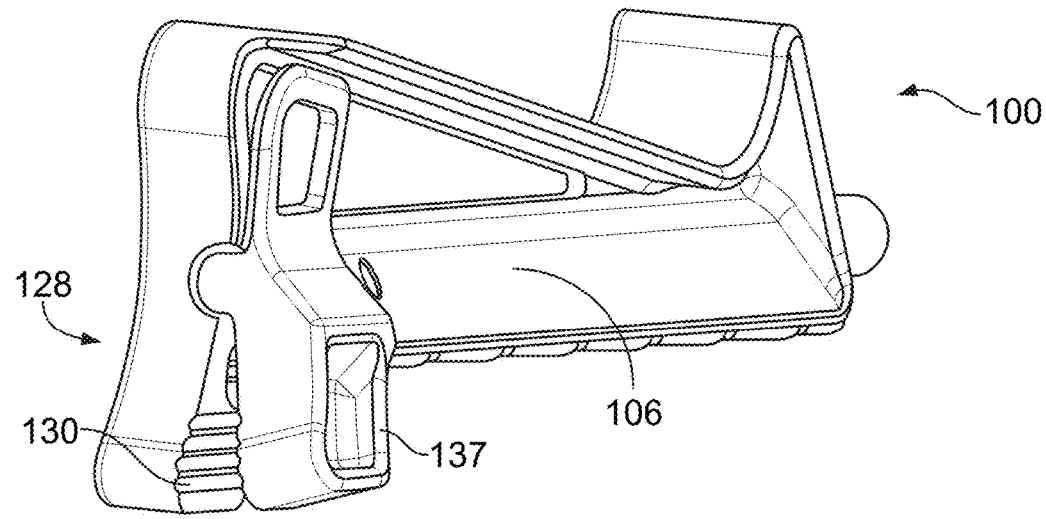

Further, in one or more embodiments as best seen in enlarged views of FIGS. 1J-K, the suction regions of the stabilizer 100 includes a plurality of cavities 122 including an edge 131 and a central hole 120 configured within a relatively deep cup 135 defined within the cavity 122. Such structure is arranged and configured to facilitate the application of a suction force to target tissue such as a skin surface. In use, the edge 131 of the cavities 122 are placed against the target tissue and a suction force is applied. The cavities 122 provide a conduit or path through which the suction force is delivered to the target tissue to thereby provide stabilization to the tissue.

Turning to FIGS. 1L-P, there is shown yet another embodiment of a stabilizer 100. As with the previously presented stabilizers, this embodiment is designed to stabilize the skin during the introduction of cellulite interventional devices between tissue layers. As before, to accomplish this, the stabilizer is connected to a controllable suction apparatus (not shown) present in a standard office or procedure room. With the connection made, vacuum is delivered to the cavities configured along the elongate portion 106. Once vacuum is achieved, interventional devices are introduced through guide channels 130 positioned in the lower handle portion 128.

Figure 1O:
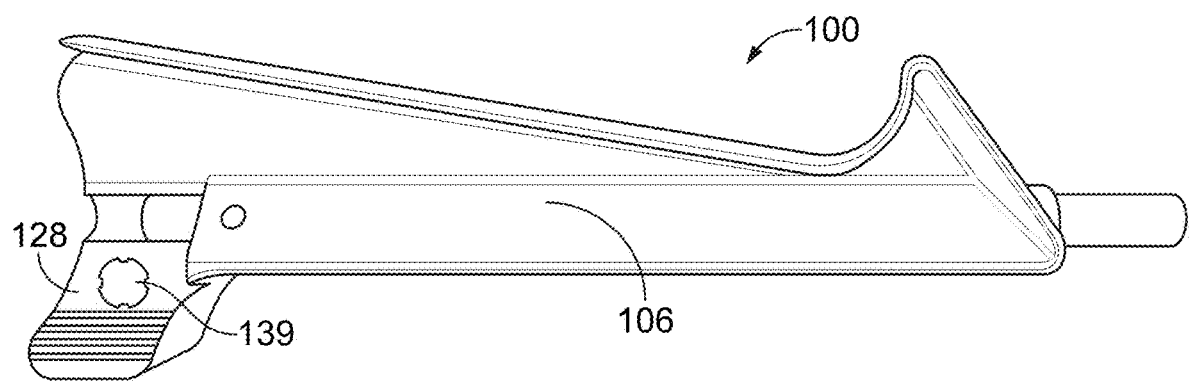
Figure 1P:
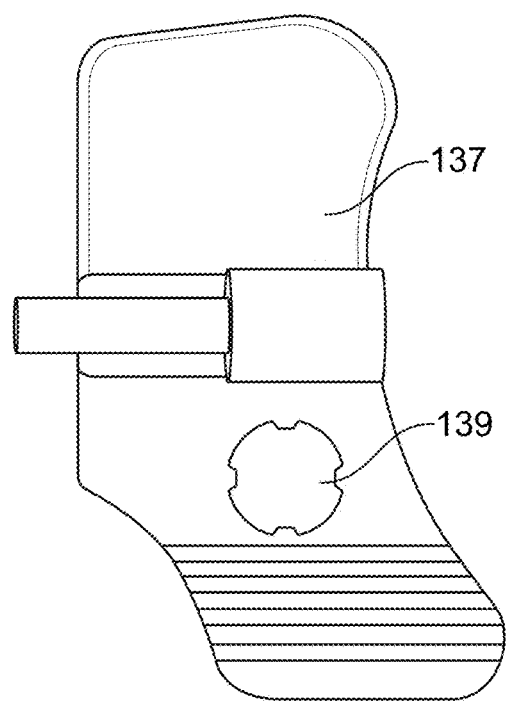

In the present approach, the stabilizer 100 includes an arm 137 that is configured to rotate between open, partially open and closed positions relative to the lower handle portion 128. When closed, the guide channel grooves on each arm for a cylindrical channel 130 through which a needle is inserted. In certain approaches, the needle is omitted and the dilator tip is made sharp enough so that it can puncture the skin and, with sufficient guidance be delivered to a target site. The arm 137 is rotatable within the lower handle 128 such that the user can pinch the upper lever 136 against the stabilizer to release the cylindrical channel 130 from around the needle and allow removal from the needle while leaving the needle in place. The arm 137 is slidable out of the stabilizer 100 for disassembly. As best seen in FIGS. 1O and 1P, the magnet 139 is positioned in one or both of the arm 137 and lower handle portion 128, the magnet 139 configured to maintain a releasable engagement between the arm 137 and lower handle 128. Moreover, disassembly of the arm 137 from the lower portion 128 facilitates cleaning and sterilization of these parts. In one approach, the magnets are formed from Samarium-Cobalt and are held in place and encapsulated with a medical grade epoxy. Further, the arm 137 and remaining portions of the stabilizer are created from stainless steel (Grade 316). The stabilizer 100 is intended to be steam sterilized in an autoclave per standard autoclave procedures before each use.

As stated, subdermal fat layers below the epidermis are contained between dermal layers connected by septa which act as connective tissue between the dermal layers. Women with cellulite have exhibited thickening of the septa in the regions of cellulite and the tensioning of septa highlights cellulite. In women, fat storage in adipose tissue has a biological purpose in that it is maximized ensuring adequate caloric availability for pregnancy and lactation. These septa may eventually contract and harden to retaining tissue layers at fixed distances, leaving pockets between such septa expanded that add to the appearance of cellulite. It is these septa that are to be stretched, re-oriented or torn to minimize or eliminate the appearance of cellulite.

Figure 1Q:
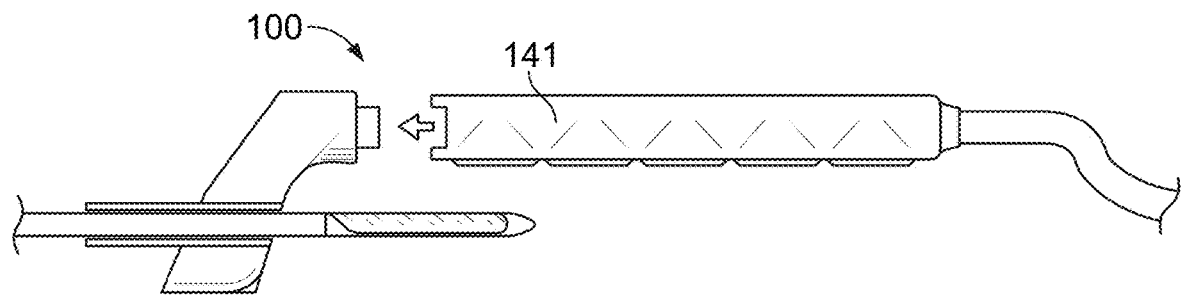
FIG. 1Q is a partial cross-sectional side view, depicting a stabilizer with a detachable suction array.

As shown in FIG. 1Q, the stabilizer 100 can include a removable suction array 141. In this way, the suction component of the stabilizer can be removed when suction is not needed and re-attached when there is a need for suction. Various approaches to removable connections can be employed such as interference fit or snap arrangement.

Figure 1R:
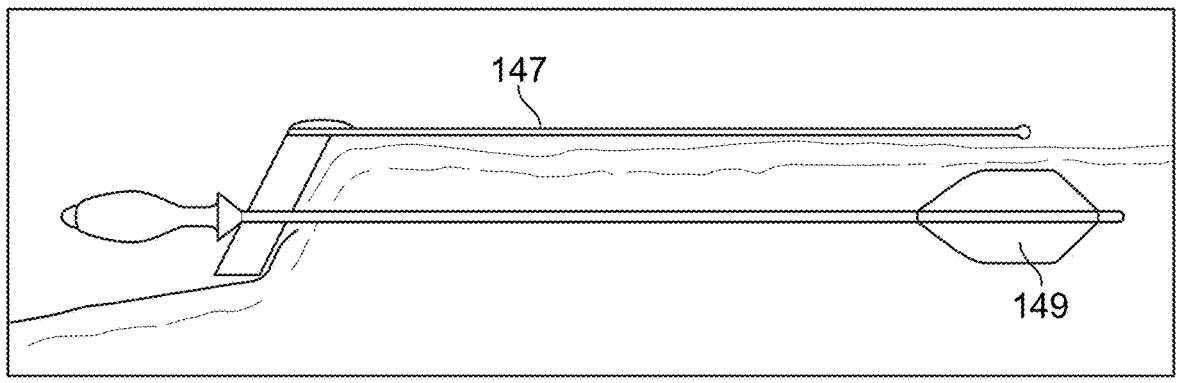
FIG. 1R is a partial cross-sectional side view, depicting an armature for facilitating treatment localization.

In place of a removed suction array, or embodied in separate instrumentation there can be provided an armature 147 that provides a visual cue concerning the location of a dilator or balloon 149 of a treatment device (See FIG. 1R). That is, the armature can include markings or the length of the armature 147 can be used to indicate the location or range of locations that a balloon 149 resides when placed in lower handle 128 and advanced between tissue layers and out of direct view by the user. The armature 147 can be removed and replaced as desired by the operator to aid in the treatment process.

Figure 1S:
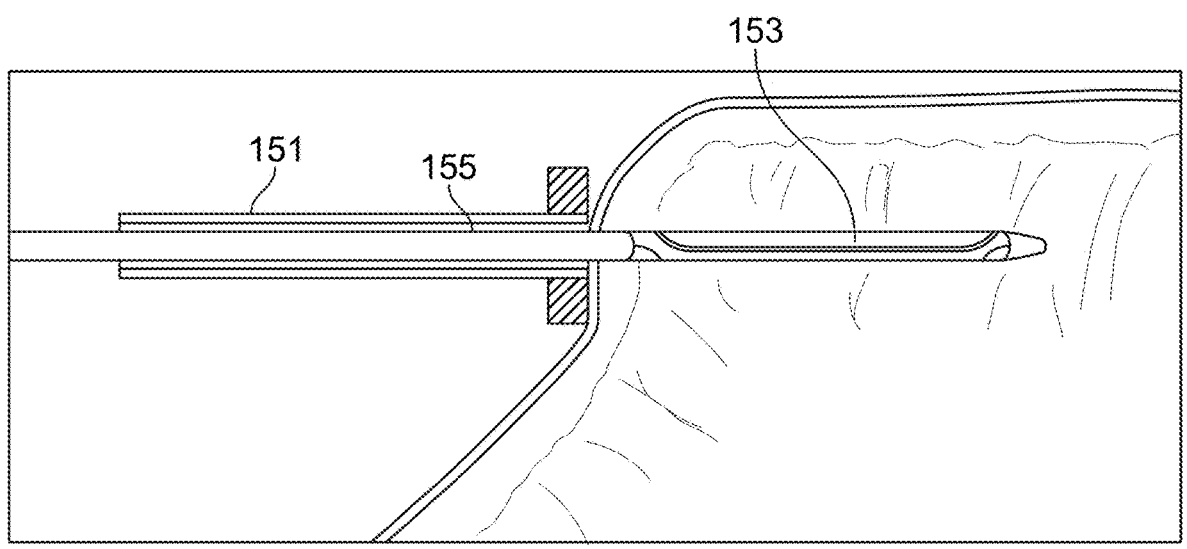

As shown in FIG. 1S, a cover 151 (e.g. PTFE material) can be configured about a dilator assembly both for protection during shipping as well as structure to keep the balloon 153 tight about the supporting shaft 155 for introduction into a desired depth of skin. Once the device is introduced, the sheath is not necessary so the sheath 151 is configured to unsheath the balloon 153 and stop at an insertion site. In one aspect, the sheath can include structure that facilitates its mating with corresponding structure of a stabilizer. After completion of a treatment, the balloon 153 is withdrawn into the sheath 151 to prepare it for reintroduction at a new location.

Figure 2A:
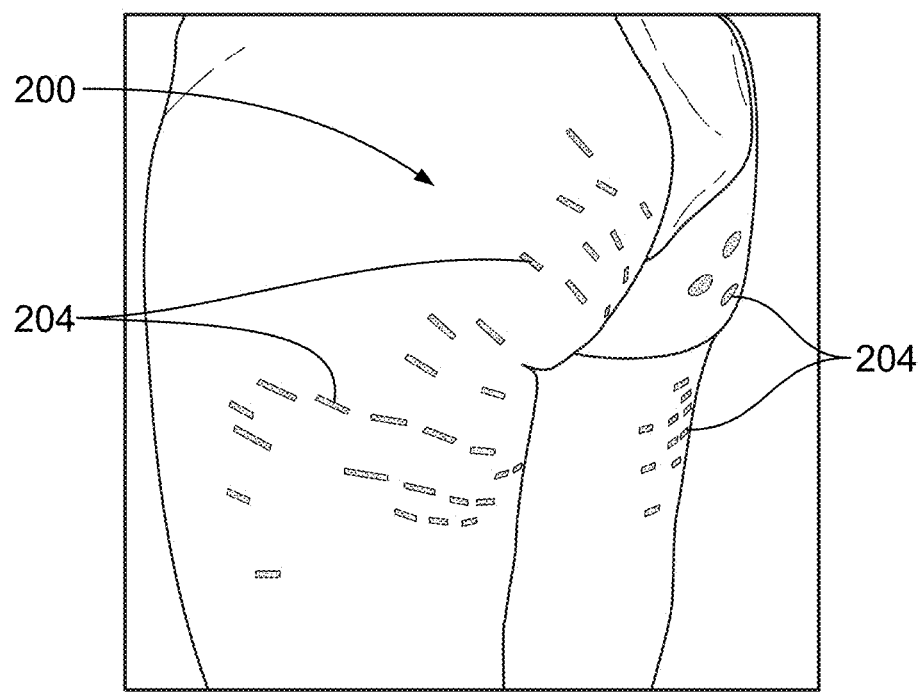
FIGS. 2A and B are perspective views, depicting cellulite on a subject's skin and a plan for treating the cellulite.
Figure 2B:
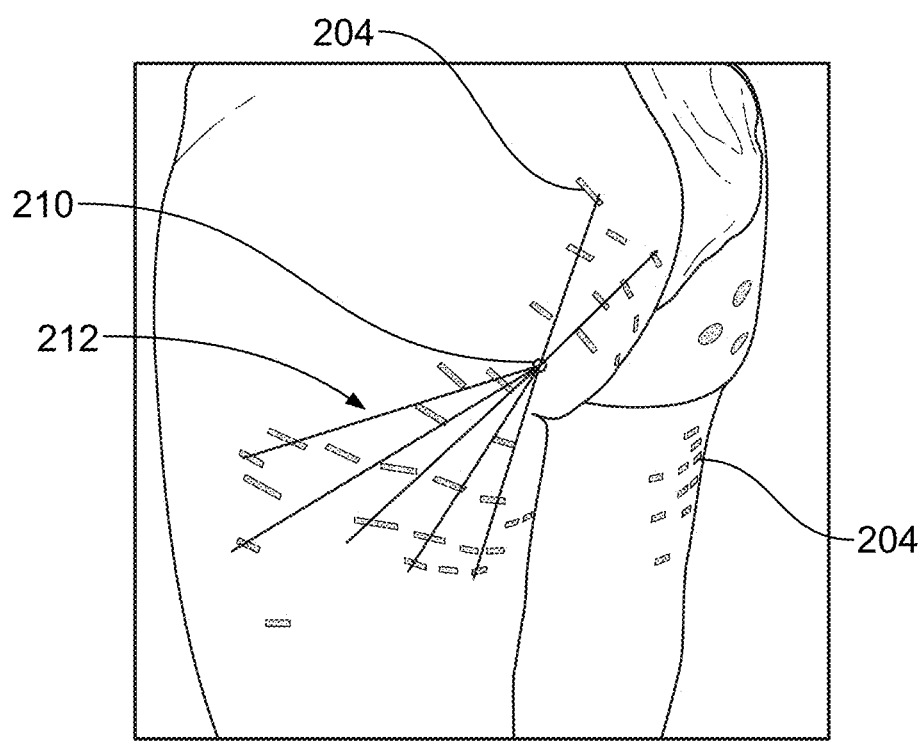
FIG. 2C is a perspective view, depicting treatment across and along Langer lines.

Turning to FIG. 2A, there is shown a person exhibiting cellulite 200 about their thighs and buttocks. In one approach to treatment, dimples characteristic of the cellulite 200 intended to be treated are identified or circled with markings 204, preferably while the patient is standing. An instrument insertion site 210 is then chosen and paths 212 selected and determined to most efficiently and atraumatically treat cellulite. Preferably an instrument insertion site is chosen that is in a crease or fold such as where the buttocks meets the thigh or in the crease between the two buttocks at a location that is not seen when the buttocks are in natural contact for improved cosmesis after the procedure healing period. Such treatment paths are selected by the operator preferably using a straight edge that bends or contours to the patient or can be generated automatically by employing a computerized controller programmed to most efficiently address and measure cellulite residing in a pre-defined treatment site. The computerized controller can be associated with a scanner that identifies specific dimples and areas for treatment such as by employing laser technology. In this regard, the computerized controller includes a program specific to cellulite treatment and is used in conjunction with an electronic and mechanical device and comprises or includes a non-transitory computer-readable storage medium and a computer-program mechanism embedded therein to both identify treatment areas and to plot primary and alternative approaches to treatments. Once a treatment regimen is developed, the system 100 is used to minimize or eliminate cellulite in a target area. Moreover, the measurement device creates a complete three-dimensional map of all cellulite relative to normal skin. By comparing improvement of volume of divots or dimples versus normal idealized surfaces, the operator calculates total and local volume benefits of therapy and track improvement over time.

Figure 2C:
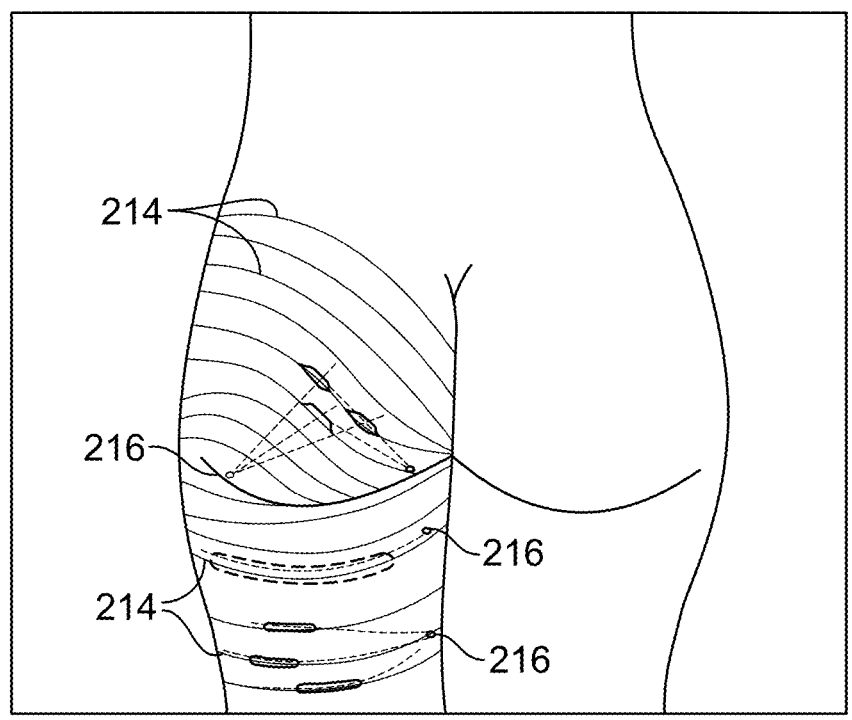

In one specific approach, as shown in FIG. 2C, the cellulite treatment follows or references Langer lines 214 existing in tissue. Langer lines 214 correspond to natural orientations of tissue fibers that exist in humans, and have been recognized as being generally parallel to the orientation of muscle fibers. The Langer lines 214 can be used as a reference to treat cellulite. Notably, cellulite appears to be related to and fall along the locations of Langer lines. In one approach, multiple treatment targets along Langer lines are treated from a single entry 216, the Langer lines 214 providing a map along which treatment is accomplished. Thus, treatment can be directed along Langer lines 214 as shown on the thigh for illustrative purposes to treat targeted septa, or additionally or alternatively, treatment can be transverse to Langer lines 214 as shown on the buttock for illustrative purposes to treat targeted septa. Treatment can also be directed at various positions about connecting tissue or septa. That is, septa can be stretched, ruptured or disrupted from various sides or angles respecting septa. Thus, septa can be treated from above, below or the sides of septa to achieve the best results. For example, in a particular situation, treatment can be most effective from above a particular connecting tissue to take advantage of gravity where treatment forces placed on the connecting tissue coincide with the direction of gravity or the direction that gravity most often works on a standing body, as it has been observed that cellulite is often most visible in a standing individual.

Figure 3D:
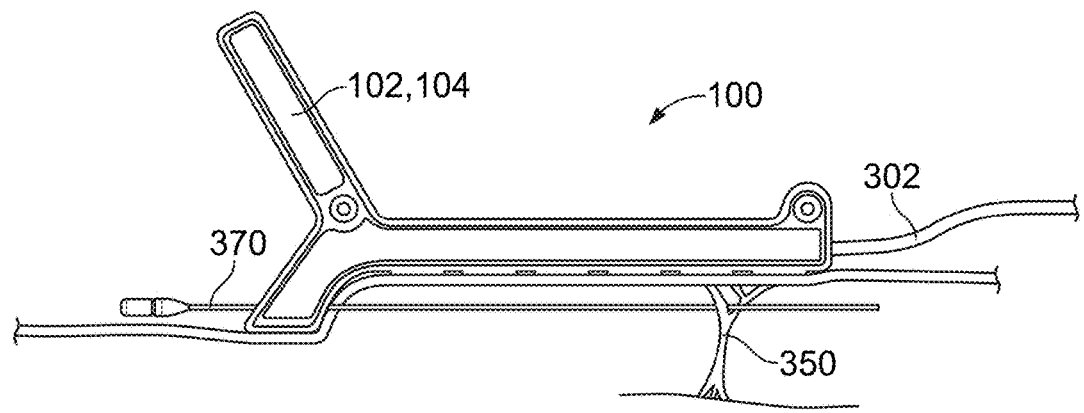
Figure 3E:
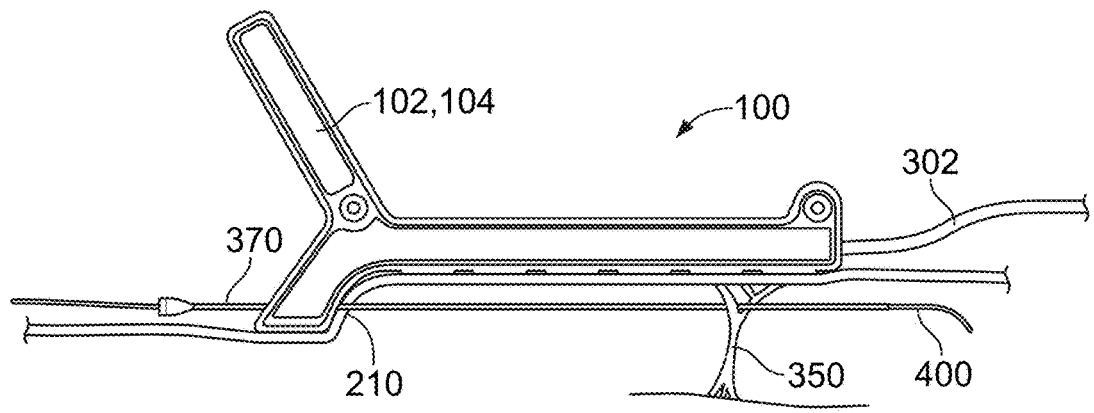

Referring now to FIGS. 3A-K, there is shown various aspects of one embodiment of the present invention for treating cellulite expressed as dimples 210 in the skin surface involving a focal balloon contouring system (FIG. 3A). While following a treatment regimen and aligning channels 130 of a lower handle portion 128 of one or more stabilizer body(ies) 102, 104 with an identified insertion site 210, suction is applied within the treatment system 100 such as by employing any one of conventional suction means such as through a tube 302. As suction force, or alternatively another adhering force or pressure, is applied to the skin 304 of a subject undergoing a cellulite treatment procedure, the skin 304 is drawn into engagement with the underside or lower portion 124 of the stabilizer 102, 104 and against cup-shaped cavities 122 (FIG. 3B). When held in such a configuration, there is provided a stable platform or foundation for creating subcutaneous access through the insertion site 210 (FIG. 3C). The particular channel 130 selected for inserting interventional instruments is selected based upon the subject's anatomy as it relates to the septa 350 (only one shown for simplicity) connecting tissue layers 360, 362 that define the chambers retaining fatty or other tissues. While anesthetic and/or sedation is taking effect, ultrasound can be used to assess the subcutaneous trajectory and depth of the various connective tissue bands responsible for the surface unevenness. The ultrasound evaluation can help with the particular channel selected for the desired depth. The ultrasound evaluation can also help with positioning the dilator strategically at the connection point between the connective tissue and the dermis or the facia.

After determining the subcutaneous depth to be accessed for the stretching, tearing, re-orienting (e.g. criss-crossing) or disrupting of septum 350, a catheter or hypotube 370 containing a trocar tipped obturator or needle 380 or other tool such as a dilator with a sharpened tip is inserted through the desired channel 130 formed in the lower handle 128 portion of the stabilizer 102, 104 (FIG. 3C). Where a dilator with a sharpened tip is employed to create access to target tissue, the guidewire may also be omitted, thus allowing the dilator to create the desired path both into tissue as well as between target tissue layers. Further, the dilator itself can also be omitted and a thus, the treatment can be performed by a balloon catheter having a sharpened tip and a proximally configured taper that is designed to create a path within tissue. As stated, it is expected that the depth that these tools are inserted will be between about 6 and about 10 mm below the skin surface 304, but it is anticipated that lesser and greater depths may also be optimal for a particular subject. In any event, the depth selected is chosen for stretching, disrupting, tearing or re-orienting of the subject's septa 350. Moreover, in one embodiment, it is to be appreciated that the catheter or hypotube 370 is formed from a substantially rigid material so that a consistent plane below the skin surface is accessed. The lower handle 128 portion of the stabilizer 102 presses on the thigh or buttocks to create a depression behind the tool resulting in a vertical portion of the skin in the notch between the lower handle 128 portion and the lower surface 124 of the elongate portion 106.

Figure 3F:
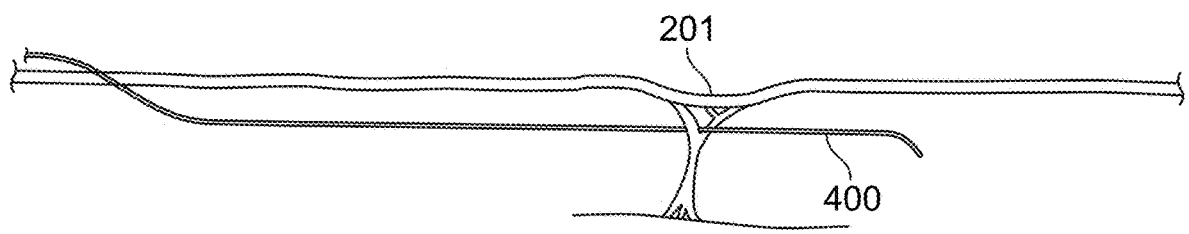
Figure 3G:
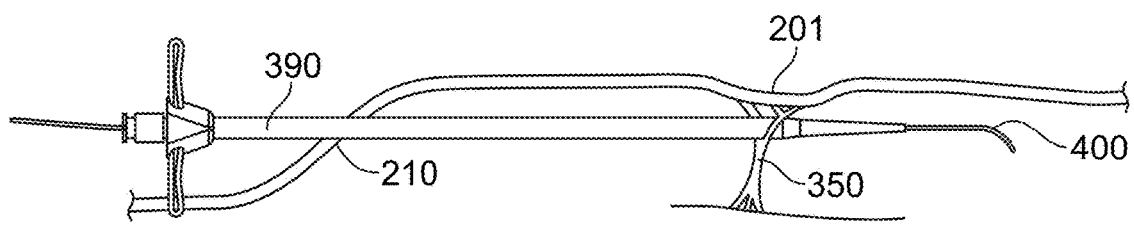

Alternatively, the lower handle 128 portion can be placed along the side of the thigh or buttock that naturally forms a substantially vertical wall relative to another surface of the thigh or buttock. The vertical portion created by the depression or naturally formed portion allows for the selection of the desired channel 130 corresponding to the desired depth of treatment. Once the hypotube 370 and needle 380 are advanced to a desired location and between the skin and facia, the needle 380 is removed (FIG. 3D) from the interventional site. Next, a guidewire is placed through the hypotube (FIG. 3E) and the hypotube is removed from the site followed by the stabilizer (FIG. 3F). As can be seen in FIG. 3F, removal of the stabilizer results in the reappearance of the dimple 201, while the guidewire 400 remains between tissue layers. The guidewire may assume a path mimicking the dimple 201 subcutaneously (not shown). A guidewire 400 inserted through the introducer assembly 390 is positioned so that it extends beyond a distal terminal end thereof and across targeted septum. As will be described further below, a distal end of the guidewire 400 can include structure facilitating the anchoring of the guidewire 400 in place. Thus, the guidewire 400 provides a path along a desired and pre-determined depth within tissue and between the skin and fascia. With the guidewire in place, an introducer assembly 390 is introduced over the guidewire (FIG. 3G). It is noted that the stabilization, retraction or compression force is no longer needed as the desired tissue plane has been accessed and the guidewire facilitates the subsequent instruments staying along the previously marked treatment path. The introducer assembly 390 can be employed in the present treatment path as well in subsequent treatment paths being conducted from the same insertion site 210. Preferably, the introducer is 18 French in outer diameter, more preferably 16 French or less, so that the insertion site does not require a stitch or stitches to be closed and can be closed with an adhesive or adhesive bandage. The introducer 390 includes a lumen that is sized and shaped to accept interventional instrumentation and in certain embodiments, include structure sealing the access site so that bodily fluids do not flow out of the subject's body.

Moreover, as stated above, various approaches to creating stabilization and/or retraction forces and/or insertion sites on tissue are contemplated including employing friction or adhesion to tissue and holding such tissue against lateral movement, applying pinching forces or rolling forces and/or lifting tissue, or applying a downward force on tissue, such as with an inclined surface or wedge, to create a space for instrument insertion without using suction, friction or adhesion.

Figure 3H:
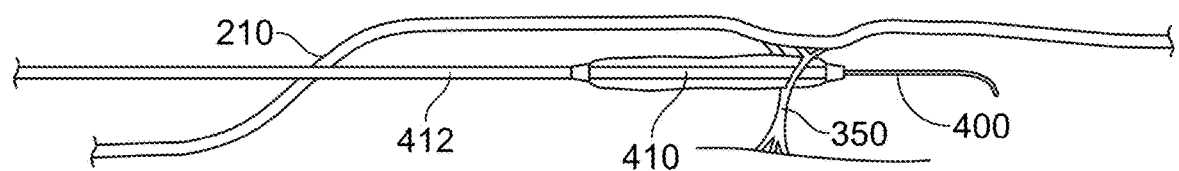
Figure 3I:
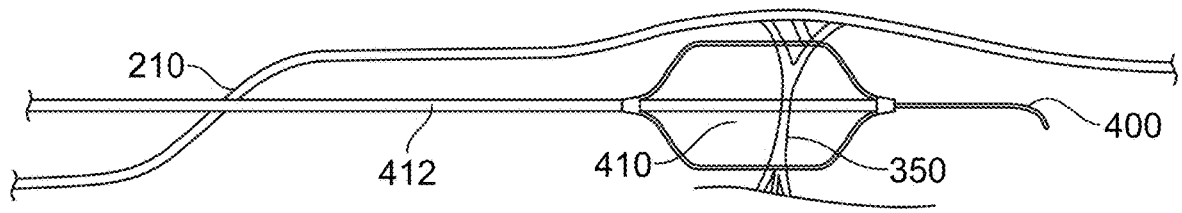

With the guidewire 400 in place, in one embodiment, the fixed dilator inside of the introducer assembly is removed, and an expandable dilator 410 attached to an elongate member 412 is then advanced through the introducer 390 lumen and along the guidewire 400 and toward the septum or septa to be stretched, torn or re-oriented (FIG. 3H). In another embodiment, the introducer assembly 390 is removed, and an expandable member attached to an elongate member is then advanced along the guidewire 400. Using palpation, direct visualization (for example, transillumination or endoscopic) or non-invasive visualization (for example, ultrasound or fluoroscopic) or other means for determining the position of the expandable dilator 410 such as markings along the length of the instruments or simply knowing the length of the dilator 410 and its path within tissue, or providing the interventional instrumentation with radiopaque markers, the expandable dilator 410 is placed at a site below where cellulite (for example a dimple 201) is seen on the subject's skin. Once so placed, the dilator is expanded to stretch, disrupt, re-orient or tear septum 350 connecting tissue layers (FIG. 3I). Expansion of the dilator results in selective rupture or tearing (FIG. 3J) or stretching (FIG. 3K) of targeted septum 350, and the removal or minimization of dimples and the expression of cellulite on skin. To facilitate this treatment and provide for the use of a smaller dilator, the skin is actively pushed down to bring it closer to the dilator as the dilator is expanded. Use of a smaller dilator helps in deployment and re-sheathing as smaller structures are more easily deployed and withdrawn. Re-sheathing is also facilitated post deployment where the dilator is partially retained within the introducer which is left in place rather than removing it completely from the treatment site.

In one embodiment, the dilator is a non-compliant balloon with a diameter of 14 millimeters and a length of 40 millimeters. An advantage of the current invention is that a sufficient force (for example, inflating the balloon to between about 1 atmosphere and about 4 atmospheres) is focally applied to a septum or septa quickly and easily to tear, re-orient the direction of, or stretch the septum or septa with minimal or no trauma to other tissues. Preferably, the dilator has a diameter between about 10 millimeters and about 30 millimeters, more preferably between about 12 millimeters and about 20 millimeters. Preferably, the dilator has a length between about 14 millimeters and about 60 millimeters, more preferably between about 20 millimeters and about 50 millimeters. In another embodiment, the dilator is a semi-compliant balloon that is relatively better for re-folding and re-sheathing. A dilator also can include a reduced taper so that the assembly has a better working length to taper ratio, and therefore less material overall to fold. In still yet another embodiment, the dilator is a non-compliant balloon covered by an elastic sleeve that helps the non-compliant balloon return to a low profile shape upon deflation. After sufficiently addressing such septum 350, the dilator 410 is deflated and retracted along the guidewire 400 to treat other septa residing below depressions formed in the skin pursuant to the pre-determined treatment path. The procedure is repeated along additional paths pursuant to the treatment regimen. The insertion site 210 is repeatedly used for subsequent treatments. Various approaches to treatment include over-the-wire, rapid exchange, fixed wire and stylet approaches. In another approach, the dilator 410 remains inflated and the user gradually pulls or drags the inflated dilator back along a portion or the entire length of the treatment path. In this way, a dilator can be deployed in a most distal position and dragged proximally to deform tissue and rupture or realign septa thus fewer deployments would be necessary to treat a target area.

In a related approach, as shown in FIG. 3L, the treatment device includes two or more dilators 410 arranged in line or parallel (not shown) that are independently expanded to rupture or stretch septa. In this way, a larger area is treatable without having to reposition the dilator 410.

Figure 4C:
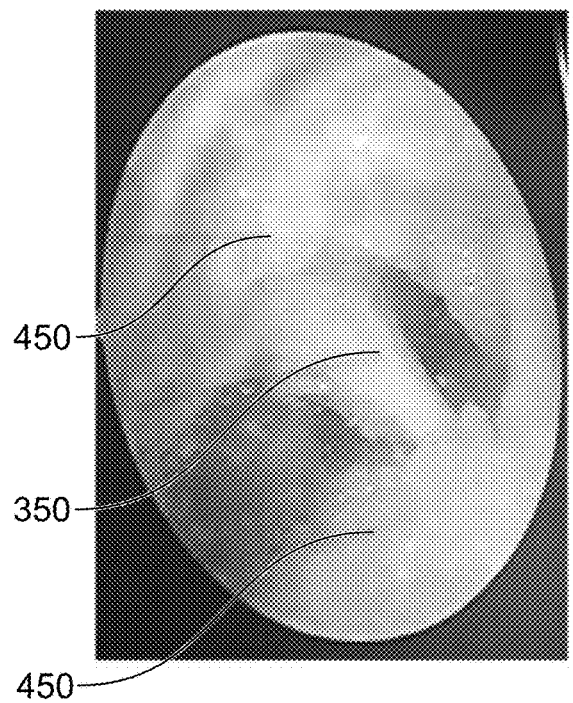
Figure 4C:
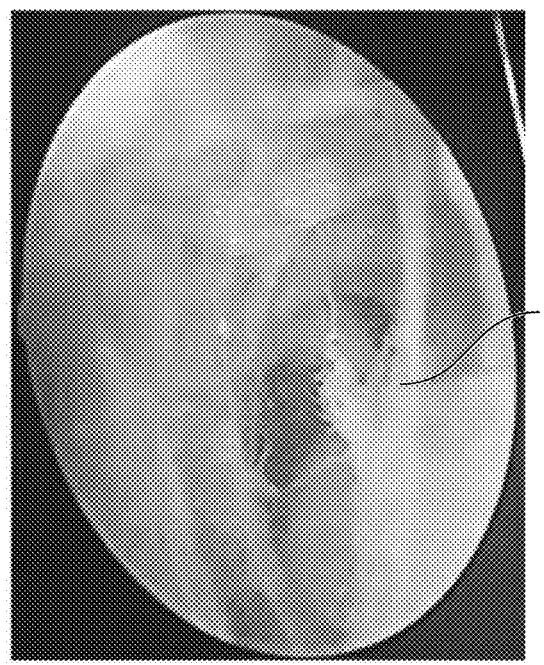
Figure 4C:
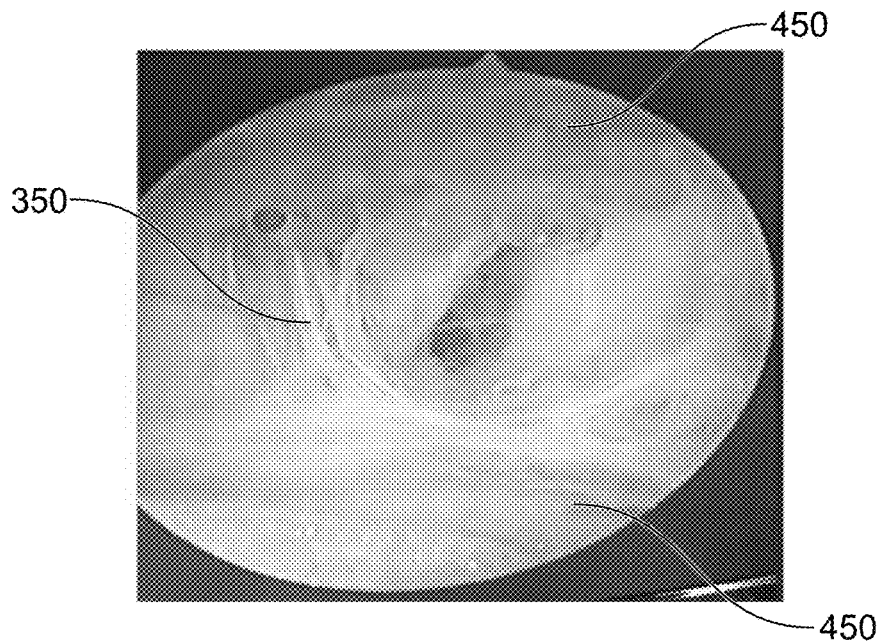

Turning to FIGS. 4A-J, one can appreciate the affect dilation has on septa 350 connecting tissue layers. As shown in FIG. 4A, prior to treatment sections of septa 350 form an uninterrupted wall of connective tissue between tissue layers 450. After treatment (FIG. 4B), the septa 350 are stretched and/or torn thus releasing the connection between tissue layers associated with such septa 350. In this regard, dilation accomplishes selective tearing, stretching, disruption or re-orienting of septa that had previously maintained a fixed distance between tissue layers thereby resulting in elimination and/or substantial reduction in depressions residing on the surface of the skin. In particular, as shown in FIG. 4C, the re-orienting or criss-crossing of small webbing of fibers 350 results from dilation such that certain of the fibers will stick to each other or have friction between them so that they do not return to their previous or pre-dilation configuration where they were more generally perpendicular in orientation relative to the skin surface. Dilation according to the present disclosure functions to selectively rupture septa that have become rigid and/or have shrunk in size or due to other physiological factors in order to accommodate the separation of tissue layers in some instances from the accumulation of fat between layers. Moreover, the disclosed approaches to dilation selectively target, disrupt, re-orient, stretch and/or tear septa that has thickened or is characterized by high tension in order to treat, minimize or eliminate the appearance of cellulite. The location, expansion and performance of the expandable member along the treatment paths can be identified through: palpation; transillumination built into the tool or in a guidewire or on the end of an illuminated obturator; ultrasound imaging; or visualization through the skin; fluoroscopically; or magnetically.

Figure 4D:
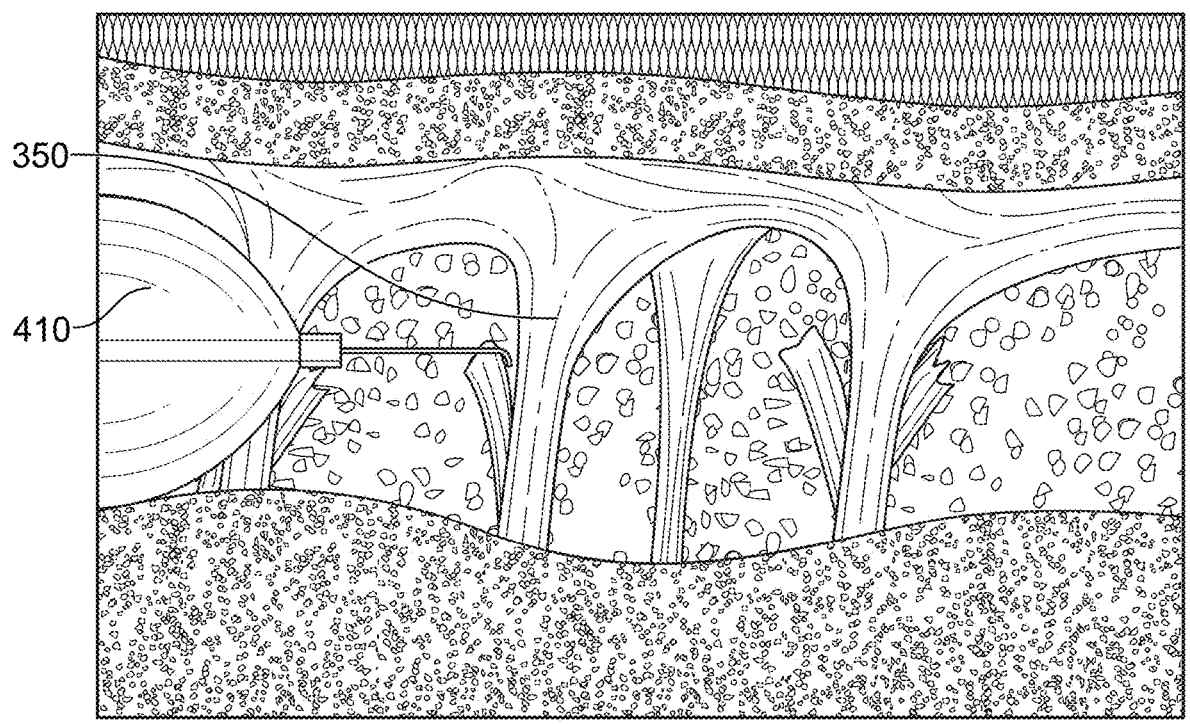
FIG. 4D is a side view, depicting rupturing and stretching of septa.
Figure 4E:
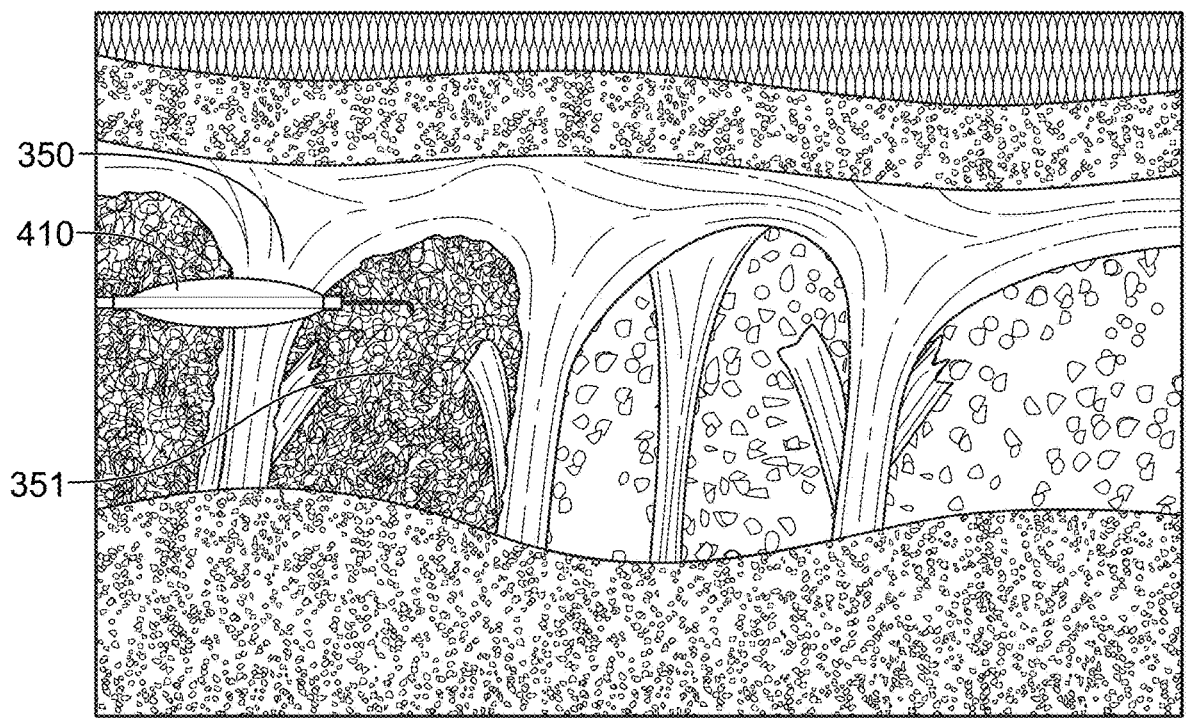
FIG. 4E is a side view, depicting filling spaces created by dilation.

As is also shown in FIGS. 4B-C, a subcutaneous space is created between tissue layers and can be used for the introduction of spacers, medicines or resorbable materials. As shown in FIG. 4D, when expanded, the dilator 410 both ruptures and stretches less dense septa 350 which helps to sustain the tissue elevation and creates a bit of a passageway subcutaneously. Additionally, a foam piece configured to fill this space, such a foam piece being delivered in a compressed configuration within a sheath in an over the wire approach to the interventional site. A similar approach can be employed to deliver other filler material such as fat 351 (See FIG. 4E). In this latter regard, a fat harvester or mixer can form part of the present system. The fat harvester or mixer is configured to pull fat from neighboring tissue and redistributes such material into the void created by dilation.

Figure 4F:
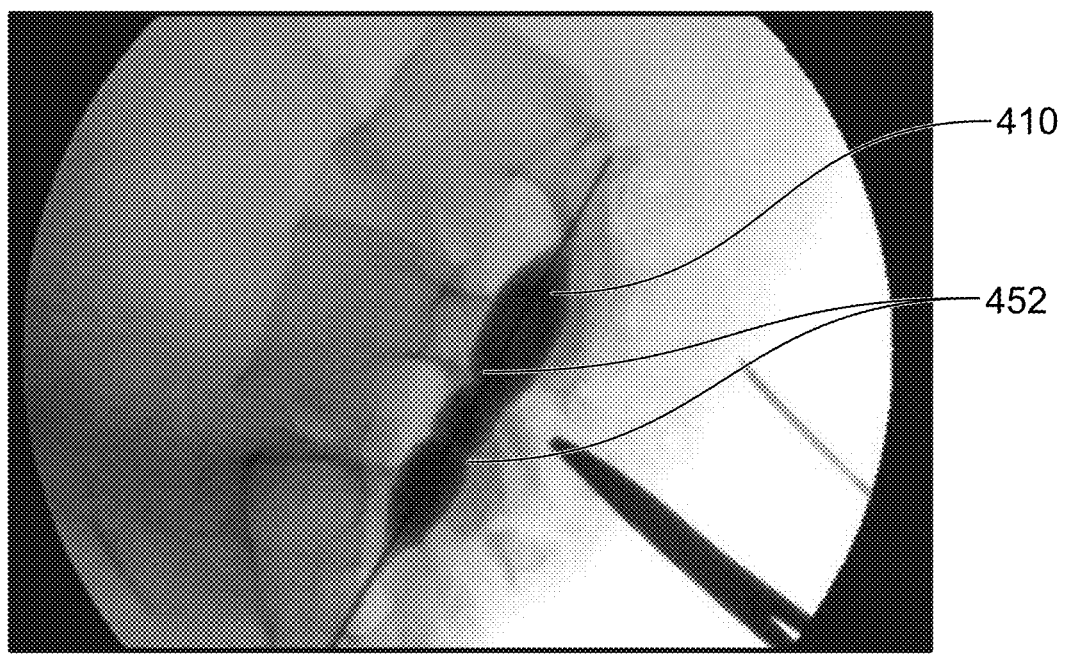
FIGS. 4F-J are remote images, depicting the expansion of a dilator at an interventional site.
Figure 4G:
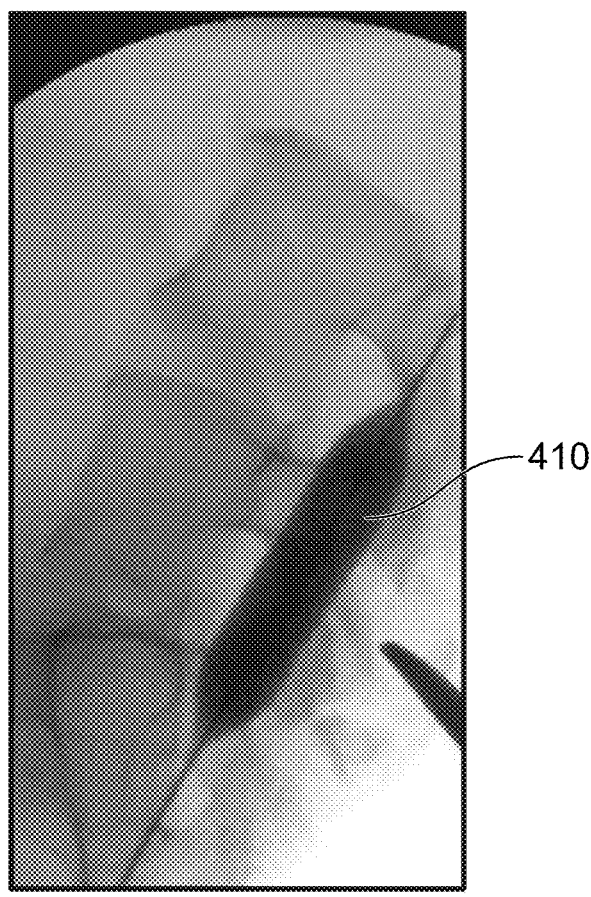
Figure 4H:
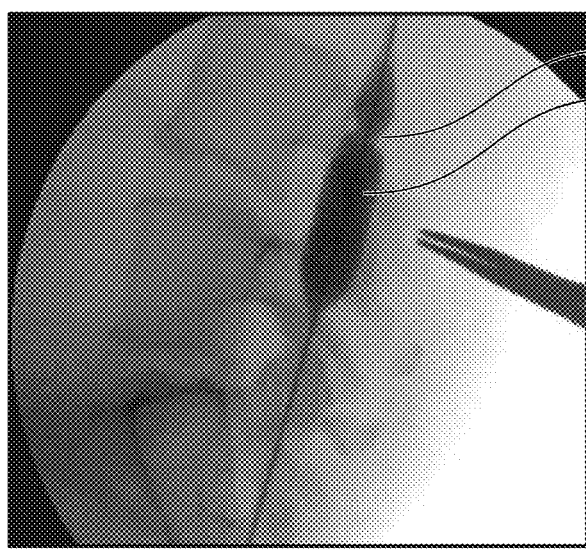
Figure 4I:
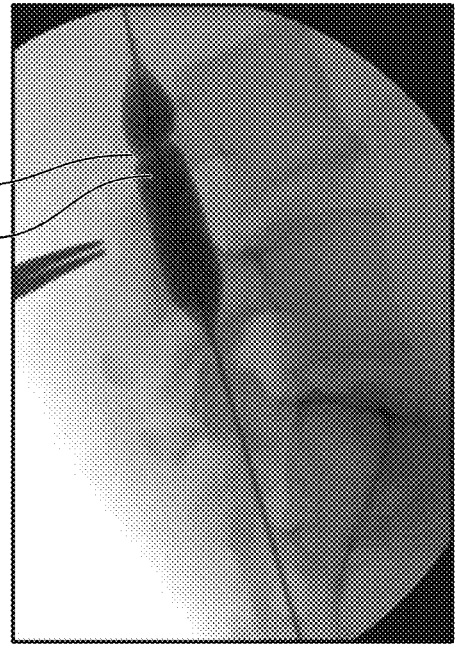
Figure 4J:
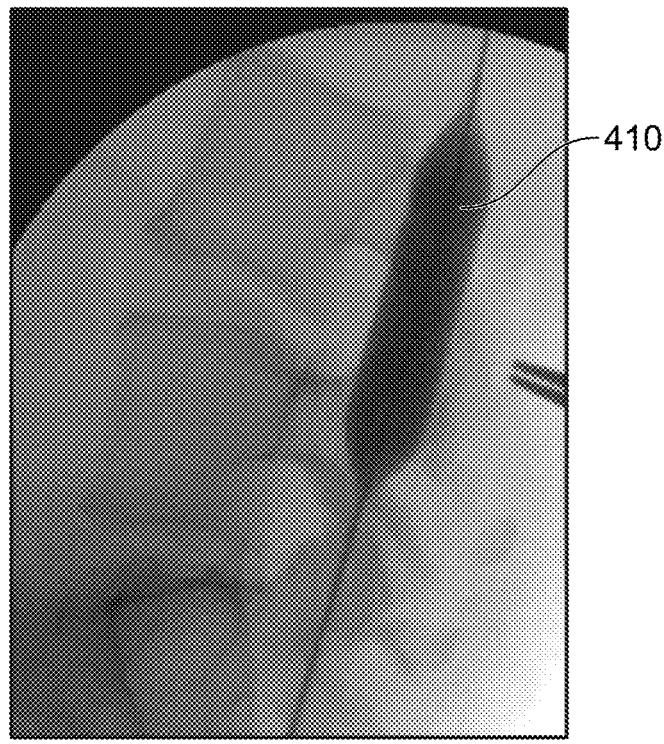

Turning to FIGS. 4F-J, there are shown various images reflecting the expansion of an expandable dilator 410 at an interventional site. As the expandable dilator 410 is expanded, it meets variable resistance from septa along its length. Accordingly, the dilator 410 is configured to exhibit enough expansion force so that selective treatment of septa is accomplished. With reference to FIG. 4F, the expandable dilator 410 can meet higher resistance from septa in two locations creating waists 452 along its length. Upon the application of further controlled expansion of the expandable dilator (FIG. 4G), the waists are resolved. As shown in FIGS. 4H-J, deep waists also can be initially created in the expandable dilator 410, and the same can be resolved by multiple increases in expansion forces provided by the expandable dilator. FIG. 4I shows the waits 452 partially resolved and FIG. 4J depicts a fully expanded expandable dilator 410. Such creation of waists and their being resolved can be observed using conventional remote imaging techniques (ultrasound; fluoroscopically; or magnetically), physically through palpation or via transillumination built into the tool or in a guidewire or on the end of an illuminated obturator. Once it is determined that the expandable dilator has fully expanded, the operator can assess whether the targeted cellulite has been treated as desired. Should further expansion be necessary, a larger or differently sized or shaped expandable dilator is employed at the interventional site.

Figure 4K:
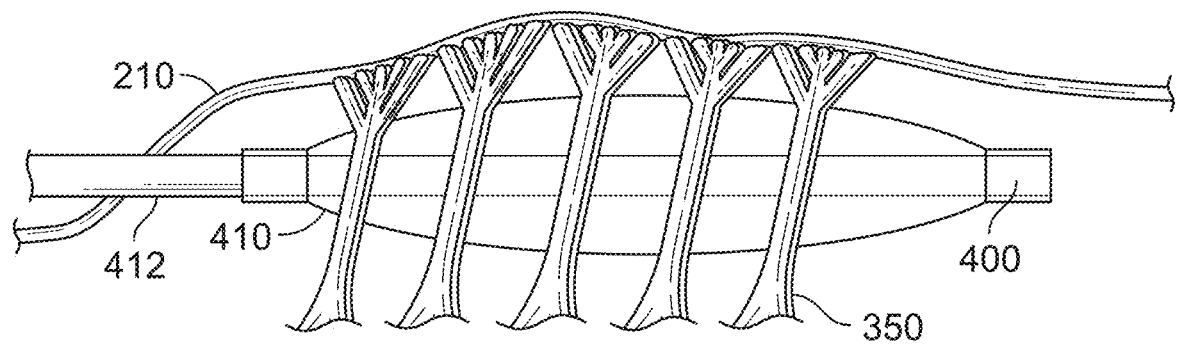
FIGS. 4K-M are side views, depicting the treatment of a plurality of dimples with a single dilator.
Figure 4L:
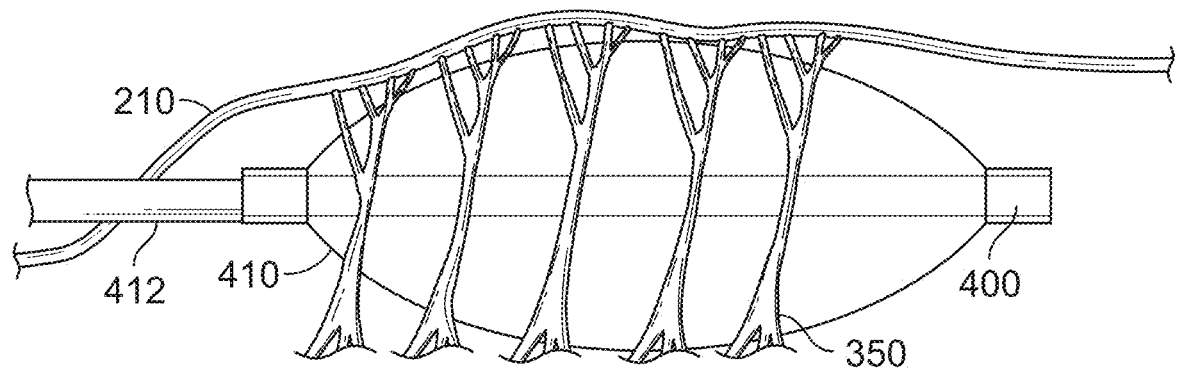
Figure 4M:
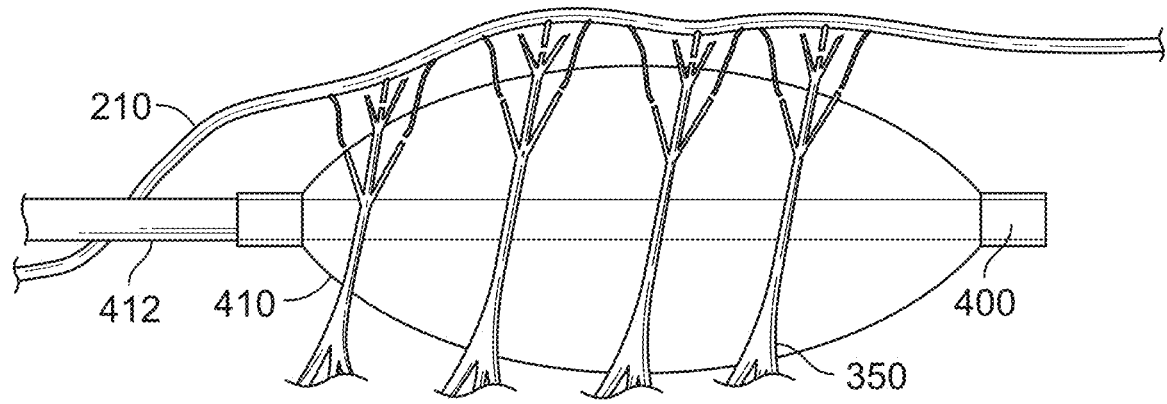

Moreover, as shown in FIGS. 4K-M, it is to be appreciated that one or more septa 350 can be traversed with a dilator 410. Once placed as desired, the dilator is expanded to stretch and/or rupture septa 350. In this way, a plurality of dimples formed on the surface of the skin can be treated with a single dilator 410.

As stated, after completing treatment of one target area, the procedure is repeated to treat other target areas. Accordingly, employing the same introducer assembly 390, the stabilizer 102, 104, hypotube 370 and needle 380 combination can be employed to access tissue layers below other sites or depressions existing in skin, and an expandable dilator 410 can be advanced over the guidewire 400 to such sites. It is to be recognized that the system can further include structure permitting the assembly to be steerable to subcutaneous treatment sites. In such an embodiment, the hypotube 370 and needle 380 would be configured to define longitudinally flexible material, and the instrumentation would be steered to the desired position within tissue. Moreover, in certain applications, the hypotube 370 has a stiffness that varies along its length. In another embodiment, a steerable or deflectable catheter or tube is used after the needle 380 has been removed.

Figure 5A:
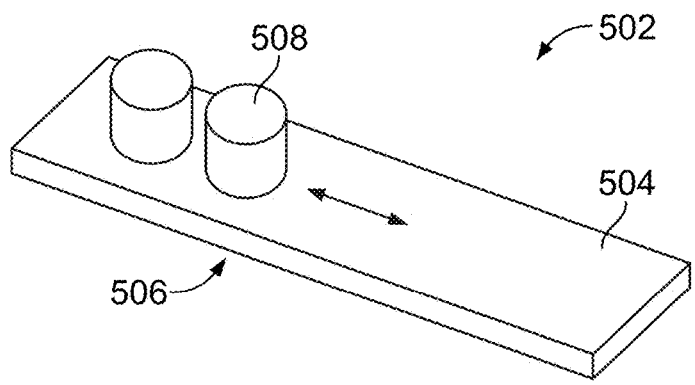
FIGS. 5A-O are side and cross-sectional views, depicting approaches to anchoring proximal and distal portions of the interventional instrumentation.
Figure 5B:
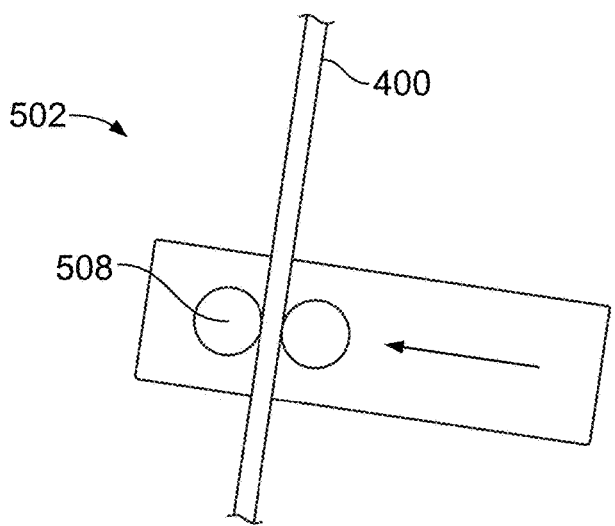

As stated, anchoring portions of the cellulite interventional instrumentation can facilitate the efficacy of a procedure. Moreover, the guidewire tip can embody flat ribbon constructions, tapered inner shafts, or tips configured to be atraumatic or blunt structures when placed or deployed as the tip is not required for navigating tortuous paths. Various approaches can be taken to stabilize or anchor a proximal portion of a guidewire 400. For example, as shown in FIGS. 5A-B, a proximal guidewire anchor assembly 502 includes a base 504, an underside of which 506 includes adhesive for attaching to the skin a subject undergoing a cellulite procedure. An upper side of the assembly includes a pair of spring loaded or lockable and slidable bosses 508 that are positioned to releasably engage a proximal end of the guidewire 400.

Figure 5C:
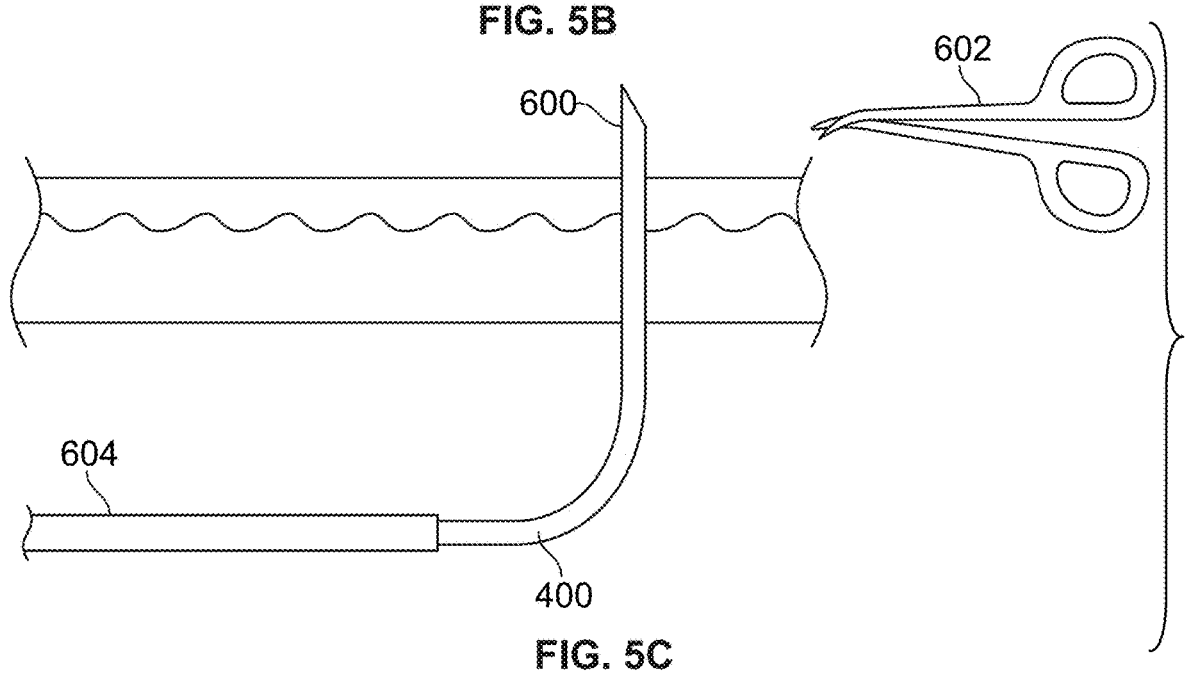
Figure 5D:
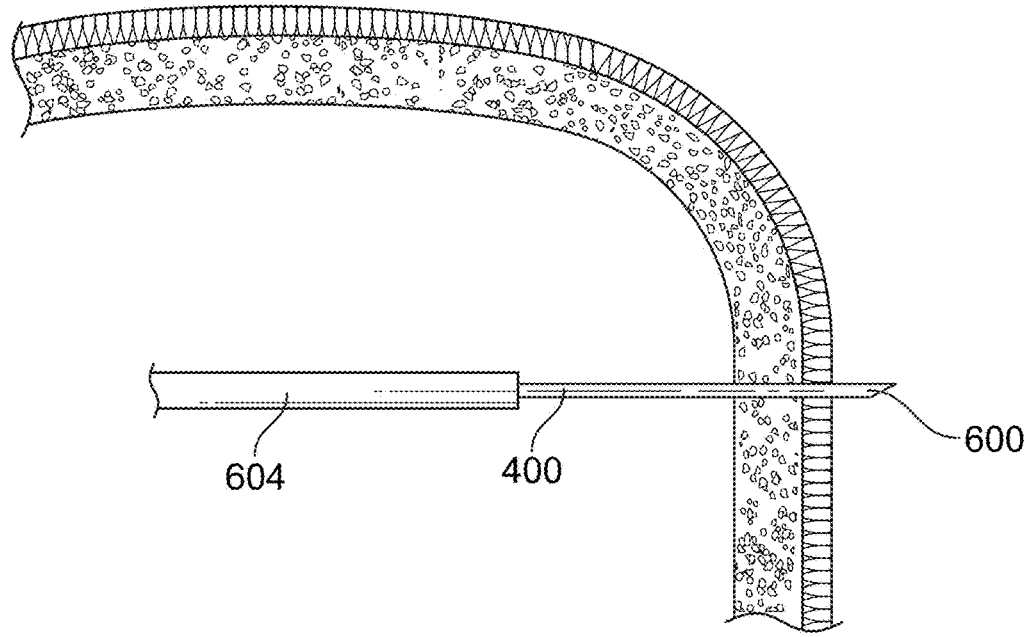

In other approaches, the guidewire 400 includes structures configured at or engageable with a distal portion thereof. As shown in FIG. 5C, the terminal end 600 of a guidewire 400 is or can be curved and advanced to an exterior of the skin of a subject undergoing the interventional procedure, or can be a straight member that exits a natural or formed curve in the subject's body, and the terminal end 600 is held in place with a clamp 602 or similar tool. When curved, the guidewire 400 is advanceable and retractable from and within a sleeve 603. The terminal end 600 of the guidewire 400 can also be straight and advanced through lifted and/or curve skin as shown in FIG. 5D. Once this straight terminal end 600 exits tissue, a clamp can be employed to hold the device in place.

Figure 5E:
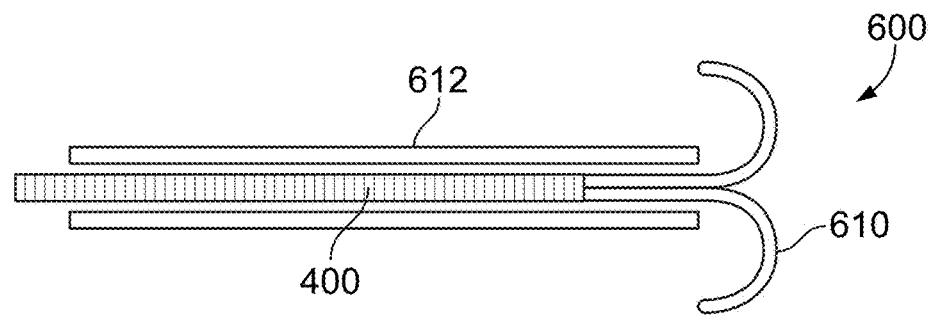
Figure 5F:
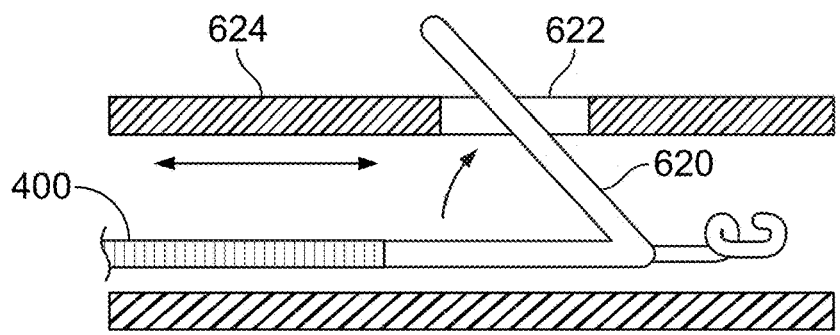
Figure 5G:
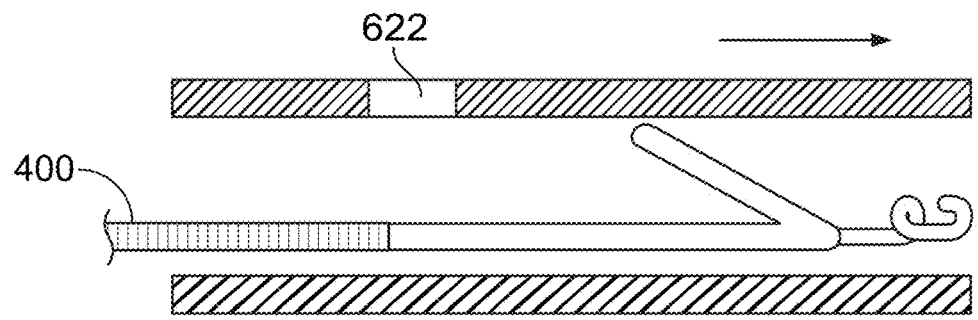

In another approach (FIG. 5E), the terminal end 600 of a guidewire 400 is equipped with a pair of curved portions 610 that act to anchor the guidewire 400 against both proximal and distal movement. The curved portions 610 can be ejected and retracted by sliding a sleeve 612 over the guidewire 400. In a similar approach (FIGS. 5F and G), the distal portion of the guidewire 400 can be provided with a v-hook 620 and atraumatic terminal end that is ejectable and retractable through a side hole 622 formed in a sleeve 624 that is advanceable over the guidewire 400.

Figure 5H:
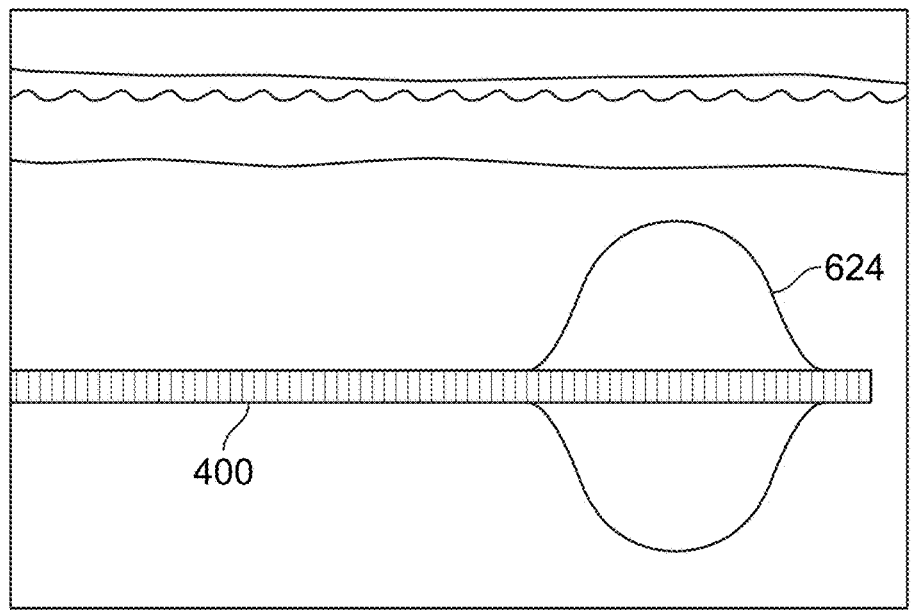
Figure 5I:
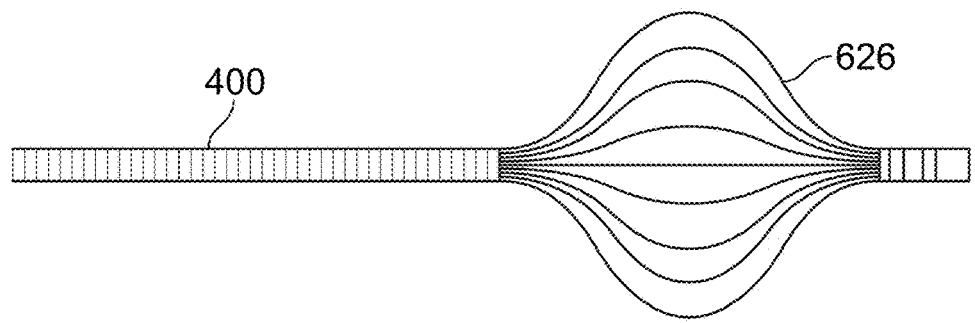

In yet other approaches to distal anchoring of the guidewire 400, the terminal end 600 is equipped with an expandable balloon 624 (FIG. 5H) or cage 626 (FIG. 5I) that act to engage surrounding tissue and anchor the guidewire 400 in place. Expansion, stabilization and retraction of such structure can be accomplished via relative movement of the guidewire and terminal end structure or a sleeve can be provided to deploy and capture the expanding structure. Additionally, the terminal end 600 of the guidewire 400 can be magnetized and held in place using a magnet 630 held on the outside of the skin in order to accomplish anchoring (See FIGS. 5J-K). Here, the north/south poles of the magnet can be placed against the skin or the magnet can embody a button (FIG. 5K) the magnetizes the magnet so that either the north or south pole is placed against the skin and the opposite pole faces away from the skin. Further, various other configurations for the terminal end 600 of the guidewire 400 can be utilized for anchoring such as a half circle 640 or L-bar 642 configured at the terminal end 600 (FIGS. 5L and M). Again, here, a sleeve can be provided to collapse and deploy such terminal end structure.

Figure 5N:
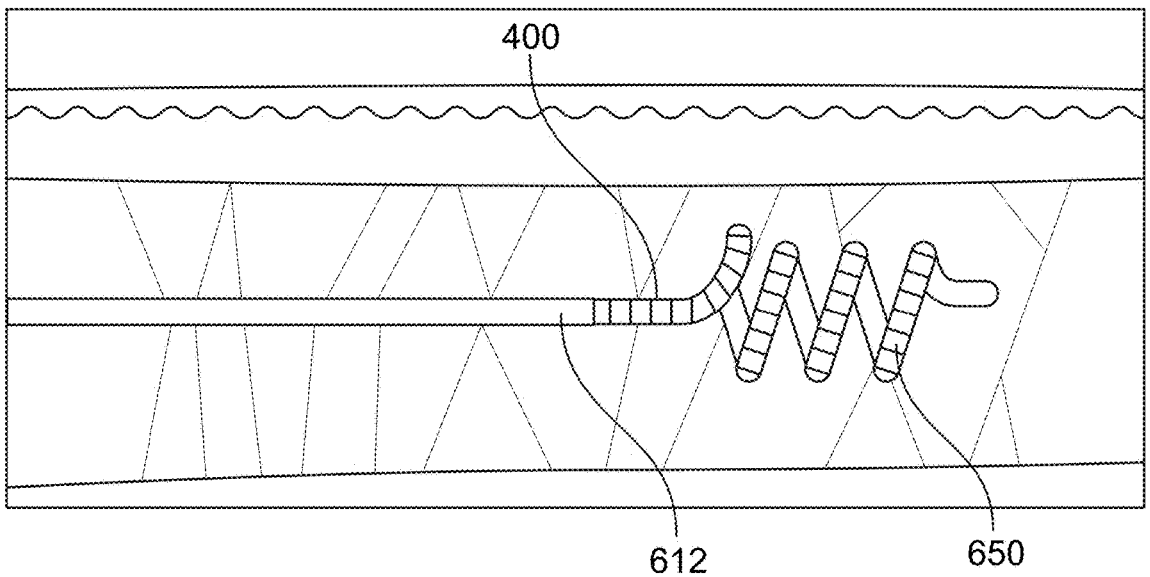
Figure 5O:
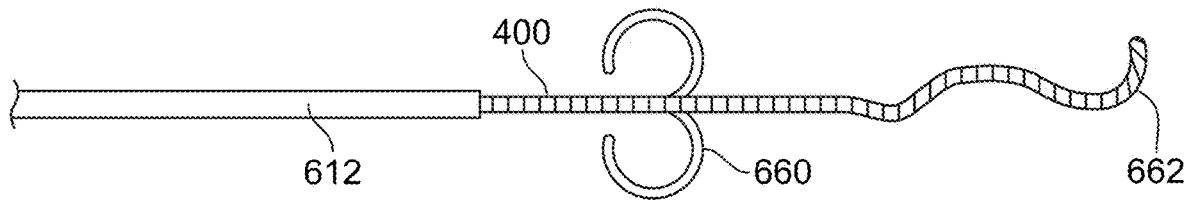

In still yet other approaches to stabilizing a distal end of a guidewire, the guidewire 400 is slidable within a sleeve 612 and terminates with a longitudinally extending coil 650 (FIG. 5N). Moreover, the terminal end portion of the guidewire 400 in another embodiment terminates with a pair of laterally extending curved portions 660 configured proximally of a wavy longitudinal structure that ends with a curved portion 662 (FIG. 5O). Each of these approaches also provide resistance against both proximal and distal movement of the guidewire once it is ejected from the sleeve 612. Advancing the sleeve 612 operates to collapse the lateral or longitudinal structure so that the sleeve 612 and guidewire 400 can be removed from or repositioned within an interventional site.

Various approaches and embodiments of expandable dilators also form part of the system 100, and the system can embody a kit including various sizes of system components including different expandable dilators. In one embodiment, the expandable dilator can be an expandable balloon, a stent, an expandable cage or other structure or can embody an expandable dilator including a plurality of telescoping members defining sequentially advanced and stacked dilators having progressively larger diameters and that accomplish the dilating function. Further, in one or more embodiments, the dilator is guided over a guidewire and includes jaws configured to open and mechanically dissect and/or spread apart and dilate the tissue. To treat a broad area, a series of two or more expandable dilators are deployed in parallel simultaneously. Additionally in a slightly more traumatic and ancillary embodiments, the dilator can be replaced with or additionally include or cooperate with a cutting balloon, a deployable pull-back cutter, harmonic scalpel, selective cautery structure or energy transmitting structure for dissecting tissue and/or controlling bleeding. Additionally, in a separate embodiment employing traumatic aspects to intervention, an atherectomy-style cutter configured to remove tissue through an opening on the side of the instrument, possibly also suctioning tissue, can be used in certain ancillary approaches.

Moreover, in certain embodiments, the system includes a squeezing tool that reproducibly applies lateral forces on the skin to emphasize the dimple or expression of cellulite so a before and after treatment effect can be obtained without requiring the patient to stand up and/or without having to remove the interventional tools. The squeezing tool is a clamp with elongated feet on opposite sides thereof or includes four fingers that pull radially inward once deployed on the surface of the skin and activated over the targeted cellulite region.

The elongate member attached to a balloon dilator is employed as the mechanism to expand and/or contract the expandable dilator by providing or removing air or other fluid (such as saline) to the dilator through the elongate member. Moreover, it is to be understood that various configurations, materials, lengths and sizes of balloon or balloons can be expandable dilators and such balloons can include stiff members on its surface for enhancing localized force. Also, the balloon catheter can be relatively short and stiff so that a guidewire is not necessary to the treatment procedure. The expandable dilators can be made from semi-compliant or non-compliant materials and can assume generally cylindrical structure or a myriad of other shapes. In one embodiment, the expandable dilator is formed from nylon. As such, balloon dilators can assume folded or rolled or pleated unexpanded configuration and then expand to its desired dilated configuration. Also, the expandable dilators can be symmetrical or asymmetrical about the elongate member in axial or rotational directions in each embodiment. Further, the balloon can be drug eluting/weeping or coated with medication or other cellulite treatment materials such as anti-inflammatory, collagenase, deoxycholic acid, salicylic acid, glycolic acid, hyaluronic acid, or cellulite treatment medicants. In addition, other instruments can be used to inject these materials or hydrogel or other biodegradable solutions into the treatment path or site. In this way, cellulite can be treated completely physically and chemically or medically and depending on the anatomy being treated a particular dilator or series of dilators can be selected for use. Also, a gel is formulated so that it accomplishes the desired stretching or rupture of tissue and remains in site long enough to generate desired plastic deformation or rupture and dissolves soon after. Such a gel can be deployed using a syringe.

Figure 6A:
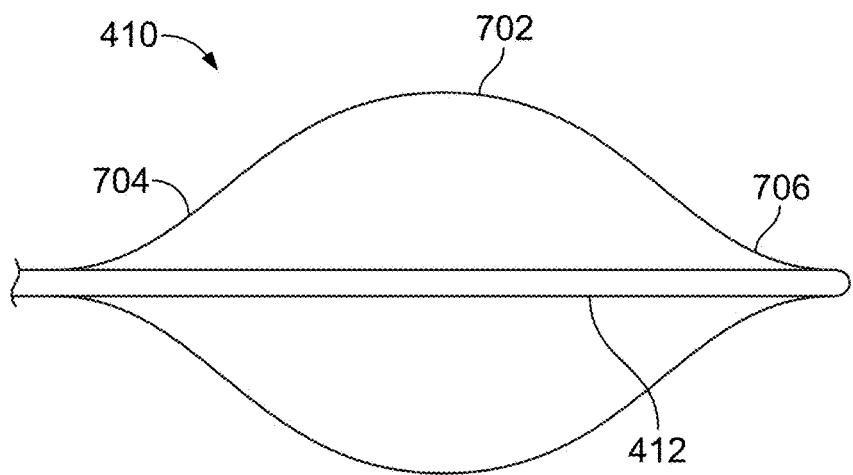
FIGS. 6A-U are side, cross-sectional and perspective views, depicting various approaches to expandable dilators.
Figure 6B:
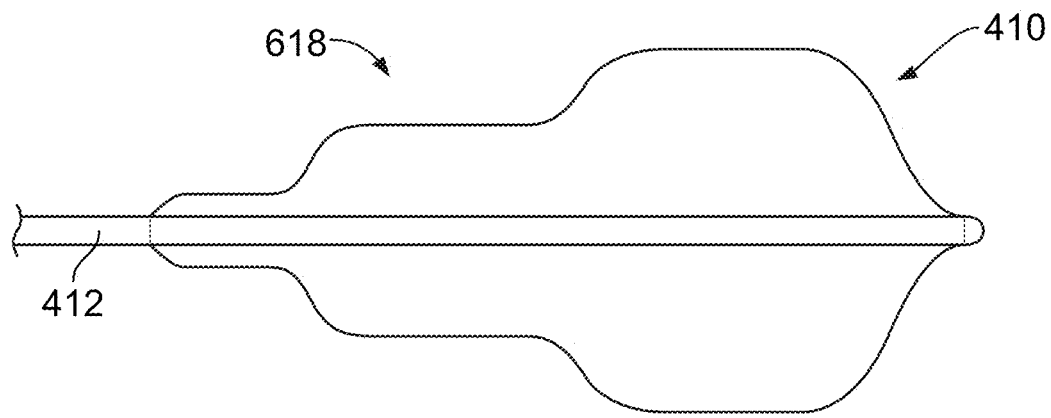

Referring now specifically to FIGS. 6A-L, various approaches to expandable dilators are presented. It is recognized that there is a proportion of balloon size, depth of skin delivery and adjacency to the target central region of the dimpled area that results in the optimal mechanical advantage to produce the best effect. The physician or operator will select the balloon size, depth of delivery and target location. In some circumstances they may use additional sizes, chose alternative depth or target location. In one or more approaches, a 10 mm deep and/or 10 mm adjacent to the lesion in the direction of the major subcutaneous tethers and employing a balloon size of at least 12-16 mm in diameter produces desired therapies. As shown in FIG. 6A, expandable dilator 410 has a relatively large mid-section 702 and proximal 704 and distal 706 portions gradually tapering in a generally symmetrical manner to the elongate member 412 supporting the expandable dilator 410. The expandable dilator 410 can also increase in size in a stepwise fashion 618 distally, and then neck down to the elongate member 412. Here, the expandable dilators are generally symmetrical rotationally about the elongate member.

Figure 6C:
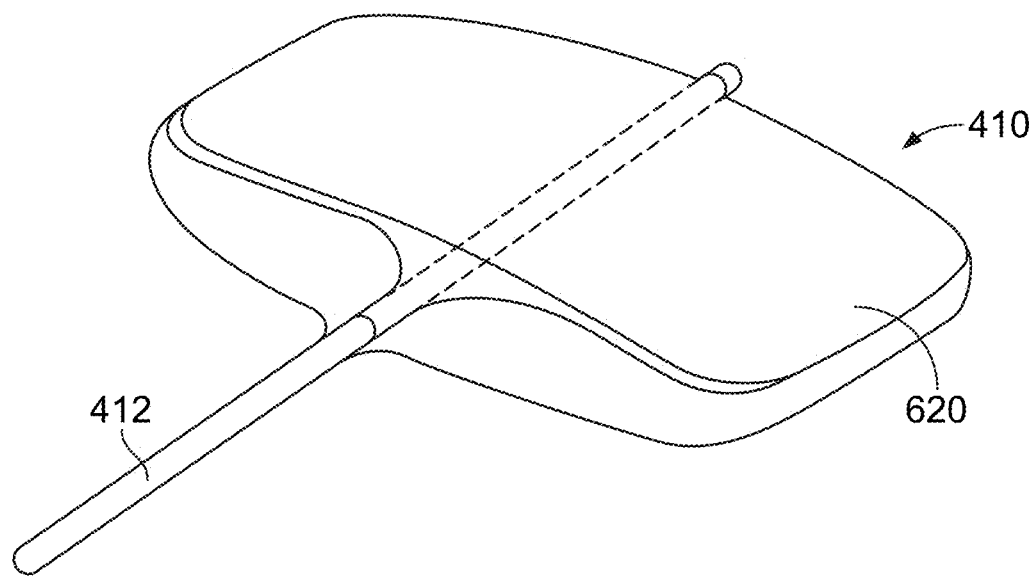

In other approaches, the expandable dilator 410 is asymmetrical rotationally about the elongate member 412. For example, the expandable dilator 410 in an expanded configuration assumes a generally laterally extending or flattened appearance 620 so that the expandable dilator 410 projects laterally a greater distance than it does in a vertical direction (FIG. 6C). In this way, the dilator is configured to treat a relatively larger area between tissue layers as lateral subcision is enhanced. It is to be recognized that this is but one example of such a dilator as various other shapes and sizes of generally laterally extending dilators define other embodiments of the present disclosure.

Figure 6D:
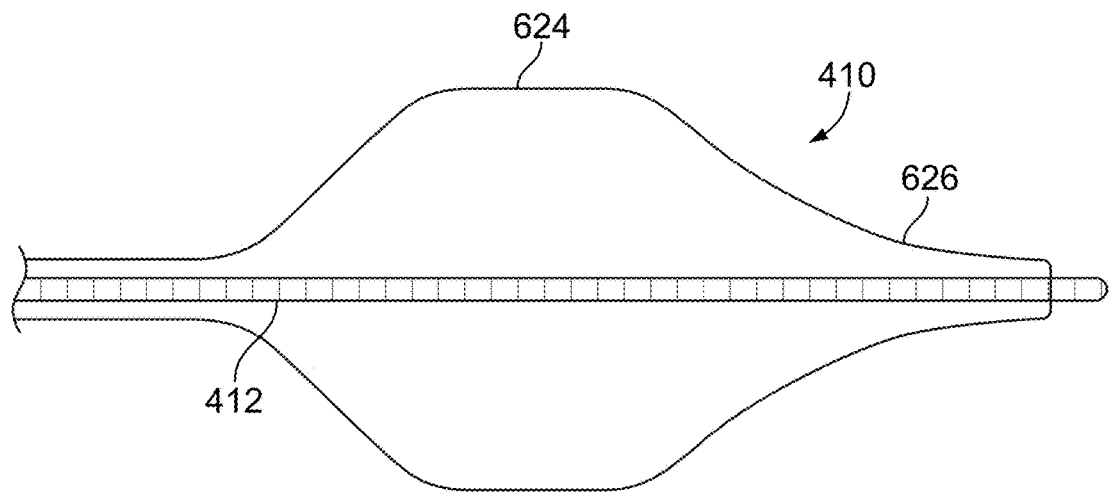
Figure 6E:
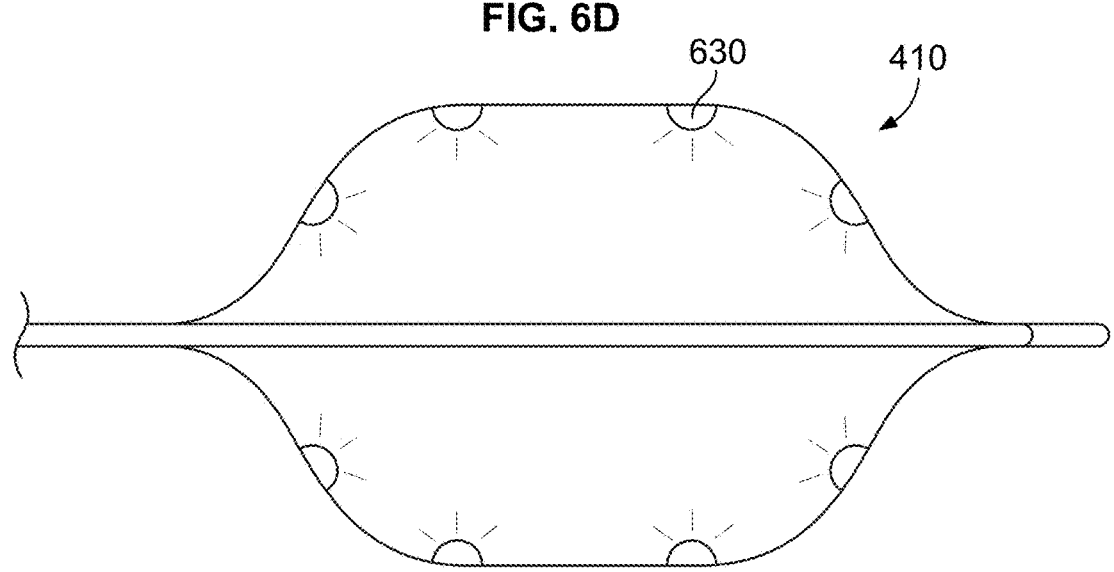
Figure 6F:
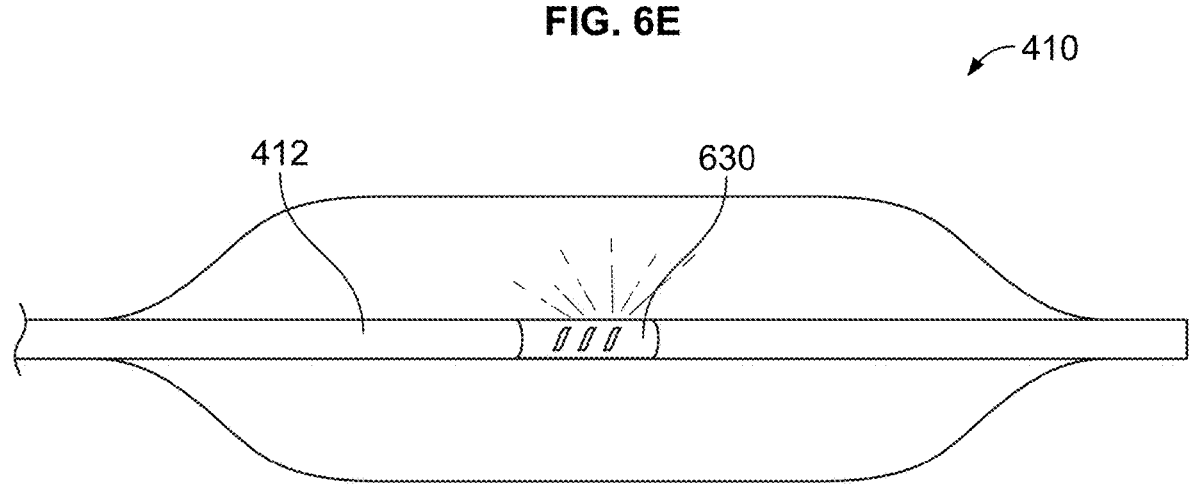
Figure 6G:
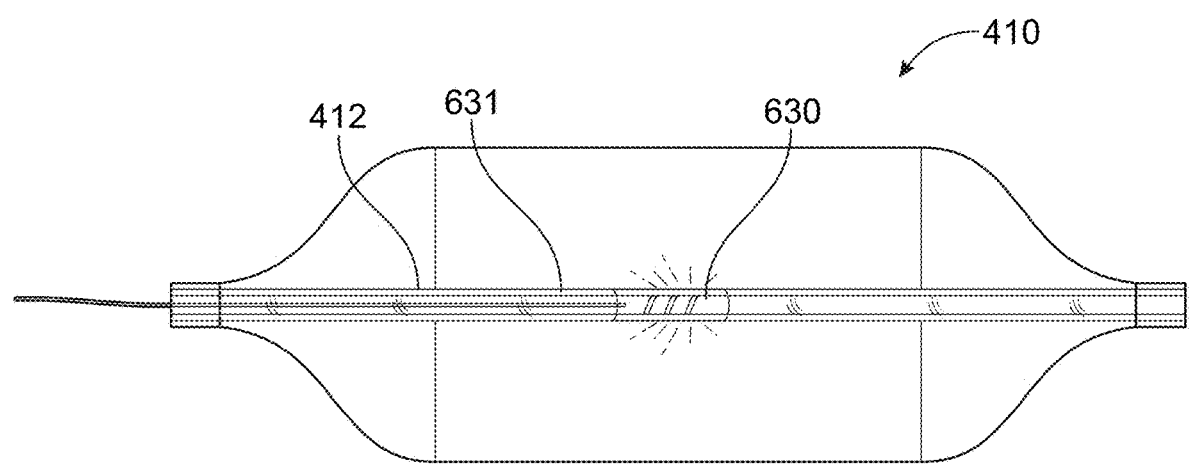
Figure 6H:
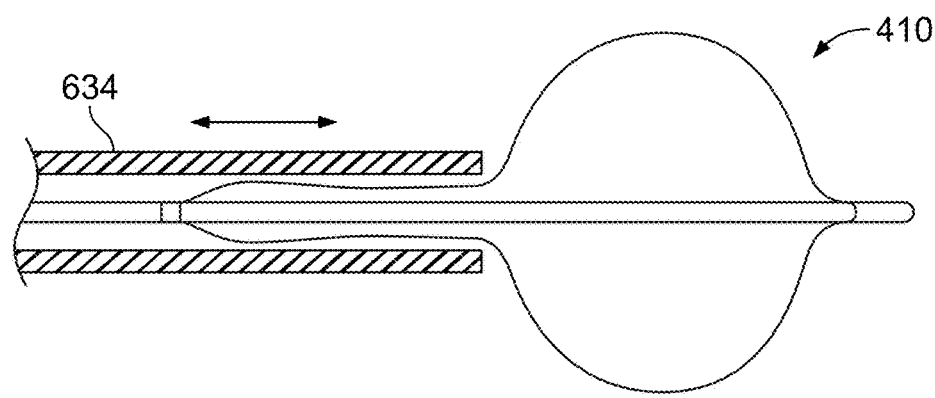

With reference to FIG. 6D, the expandable dilator 410 includes an enlarged mid-section 624 and a relatively long taper 626 extending distally from the mid-section 624. Such an arrangement lends itself well to gradually separating tissue layers as the dilator is advanced subcutaneously.

In other embodiments (FIGS. 6E and F), the expandable dilator 410 is equipped one or more illuminating structures 630 such as LEDs. Thus, the illuminating structures are placed in one or more of along a portion or an entirety of structure defining the expandable dilator 410 or along a portion or an entirety of the elongate member 412 supporting the expandable dilator 410. In an alternative embodiment (FIG. 6G), the light source 630 can also be associated with a slidable member 631 within a transparent lumen within the dilator 410, allowing the light source to be positioned along the length of the dilator 410 while the balloon is stationary. These lights 630 are useful in employing transillumination in an interventional procedure. The location of the expandable dilator 410 is directly viewed by an operator as it is translated subcutaneously between tissue layers. The lights are also useful in communicating if a dilator has been fully or partially expanded. Such information is useful to an operator as the degree to which complete or partial dilation within tissue can be indicative of the progress of a treatment.

In a further embodiment (FIG. 6H), a sleeve 634 is provided about the elongate member 410 and positionable about the expandable dilator 410 to control the degree to which the dilator 410 is expanded. Thus, smaller and/or larger regions can be treated with the expandable dilator 410 as desired or dictated by a particular application. The sleeve 634 also serves as a means for collapsing the expandable dilator for removal for re-positioning between tissue layers.

Figure 6I:
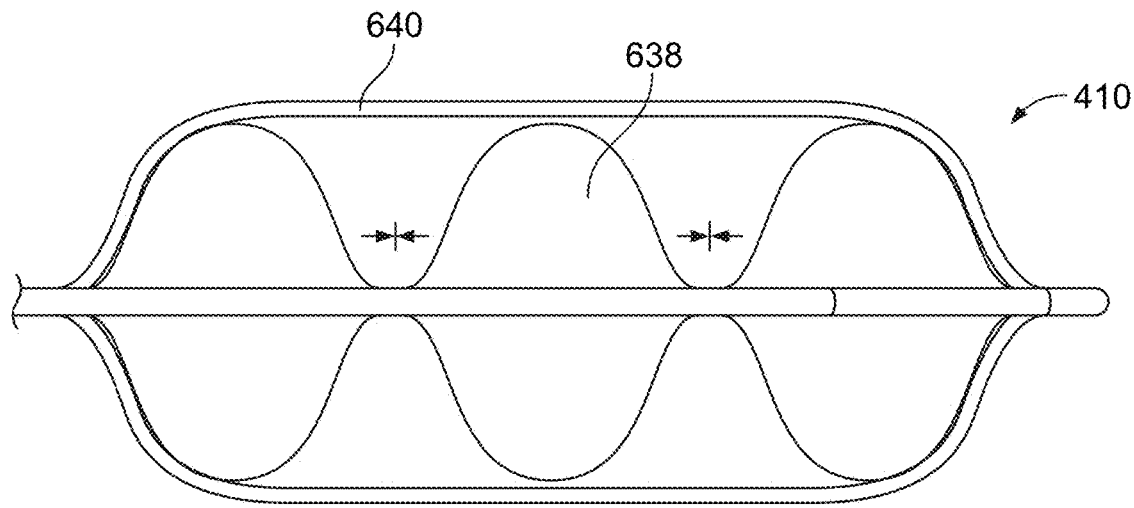

In a related approach as shown in FIG. 6I, the expandable dilator 410 is defined by a plurality of expandable portions 638 encased in an outer membrane 640. In this approach, the elongate member 412 includes structure that permits each expandable portion 638 to be expanded and retracted independently. For example, in an embodiment including three expandable portions, the elongate member is equipped with three separate lumens and/or ports each in communication with one expandable portion. The membrane 640 provides an outer surface with a smooth transition between dilator 410 sections.

Figure 6J:
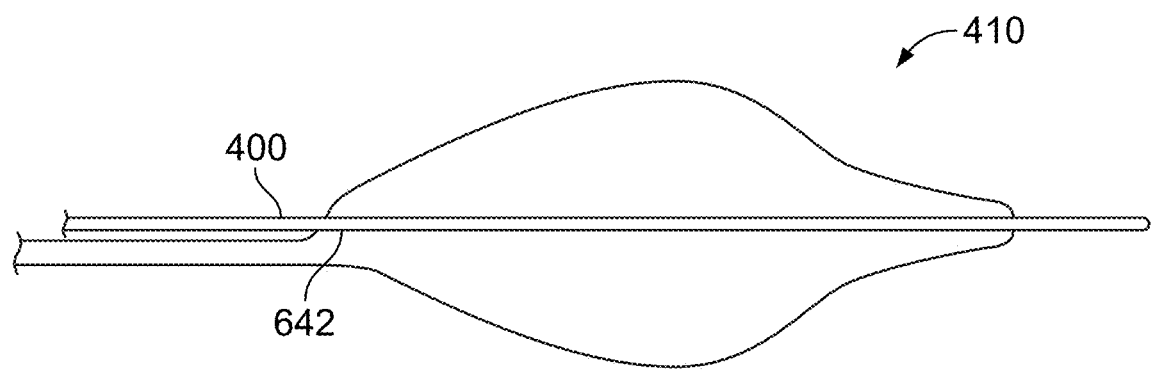

Furthermore, in one or more embodiments, an over-the-wire approach can be employed to deliver a dilator to and within an interventional site. Additionally, as depicted in FIG. 6J, a rapid exchange approach to dilator delivery is used in certain embodiments. In this approach, rather than advancing an entire length of an expandable dilator 410 and its elongate member 412 over a guidewire 400, the dilator 410 is provided with an additional lumen 642 over which just the dilator is advanced. In this way, one or more dilator assemblies can be guided over, removed and replaced from the guidewire in a more rapid fashion or succession. In this regard, the entire contents of U.S. Pat. Nos. 6,921,411 and 6,273,879 are incorporated herein by reference.

Figure 6K:
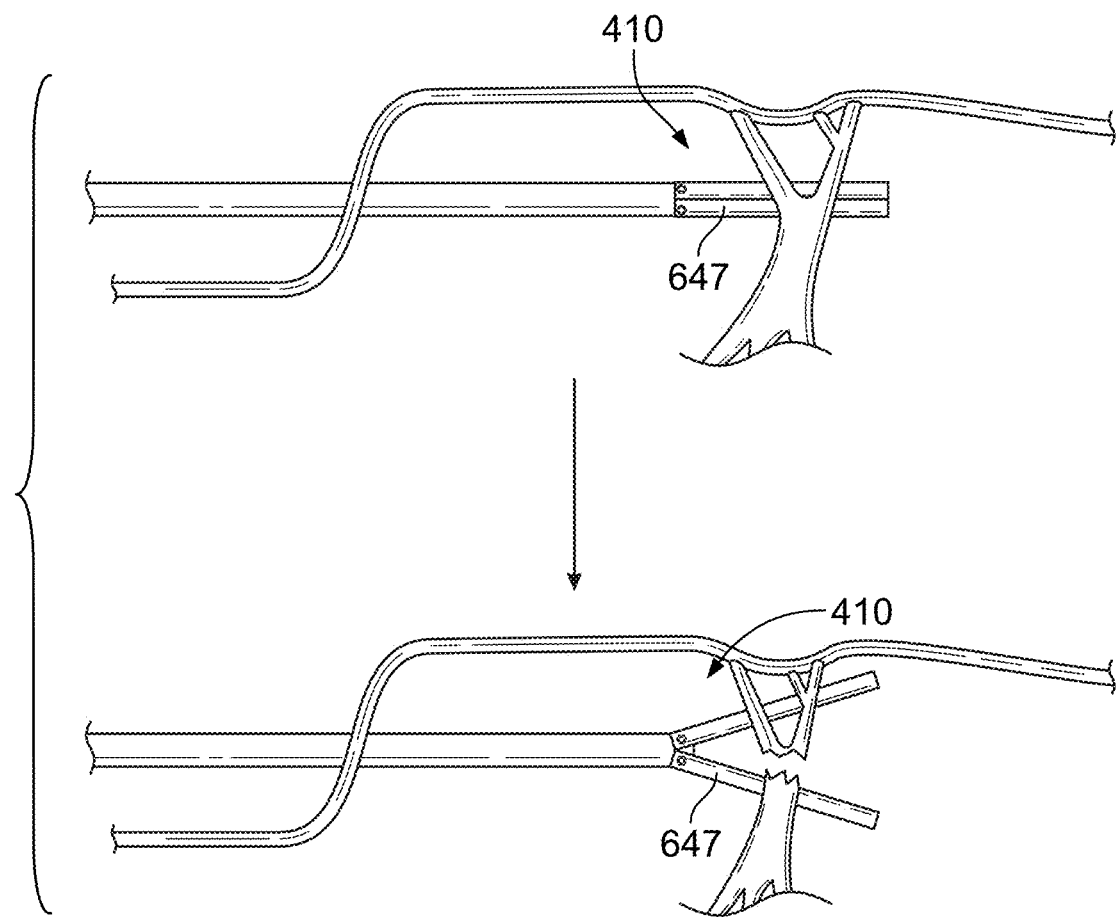
Figure 6L:
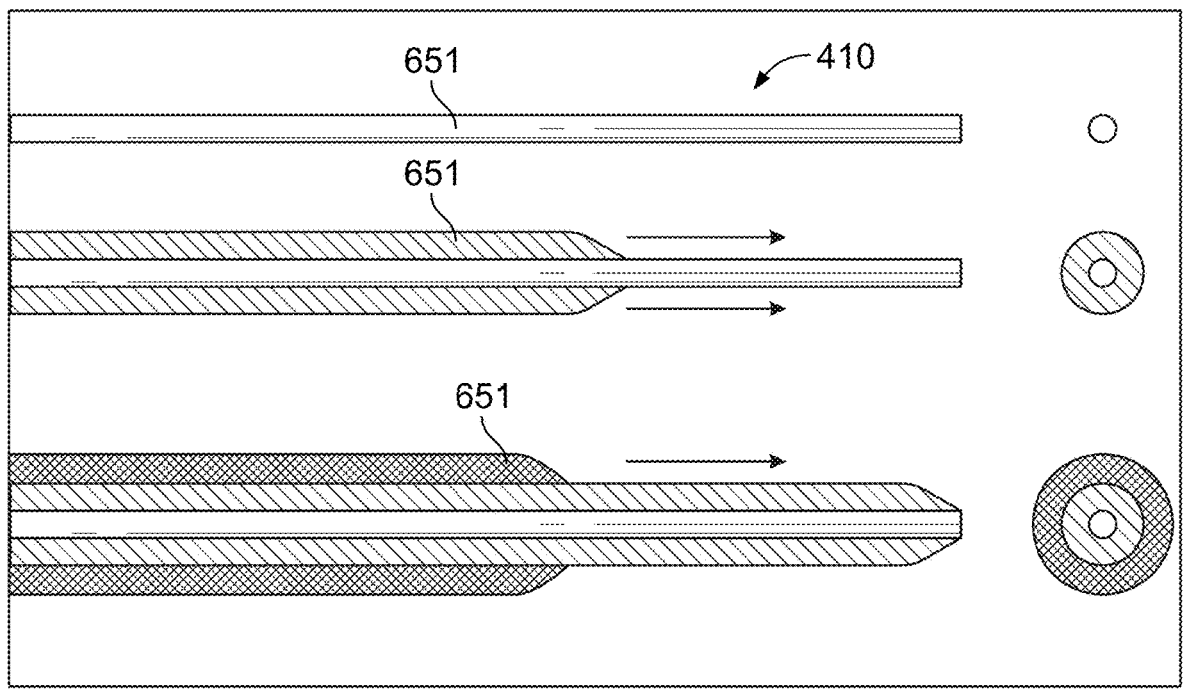

As shown in FIG. 6K, a dilator 410 can include jaws 647 that assume open, partially open and closed configurations. In use, the device is advanced to the interventional site in a closed configuration and thereafter opened to stretch or rupture septa to treat cellulite. The dilator 410 is guided over a guidewire and the jaws open and mechanically dissect and/or spread apart and dilate the tissue. The dilator 410 is advanced or retracted or repositioned as desired to treat various locations.

In another approach (FIG. 6L), the dilator 410 includes a plurality of telescoping tubes 651 that are sequentially advanced and stacked dilators having progressively larger diameters. As the overall diameter of the assembly increases to a desired target, the dilating function is accomplished.

Figure 6M:
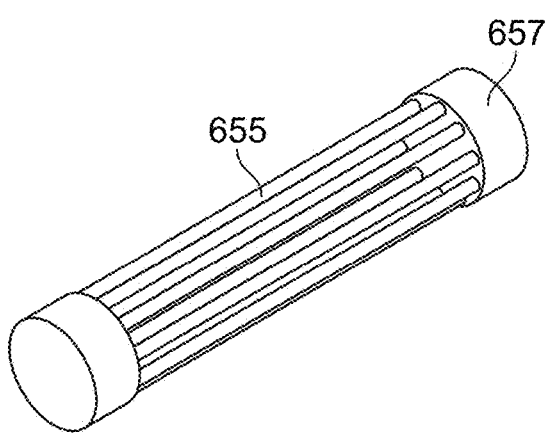
Figure 6N:
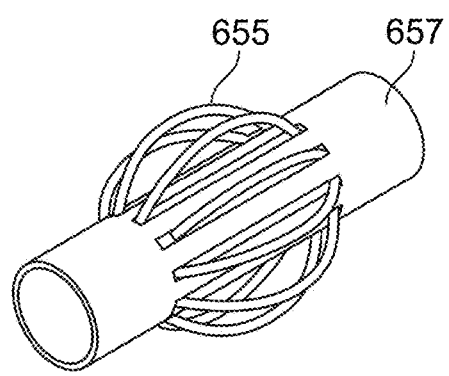

As shown in FIGS. 6M-N, the dilator can be a plurality of wires 655 that project radially outward from a tube 657 via forced displacement in a repeatable manner. Such structure provides desired mechanical control via direct actuation and buckling of the wires 655 in both distal and proximal directions and is associated with minimal re-sheathing issues. The wires can be round or flat in cross-section, and various number of wires can define the expandable structure. Moreover, the wire array can be covered in an elastomeric material to spread the load and allow for the mechanism to be retracted without other material obstructing the array.

Figure 6O:
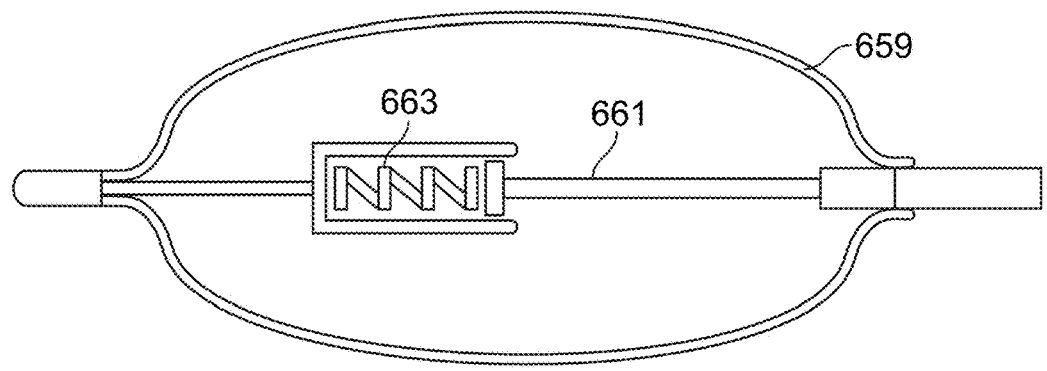
Figure 6P:
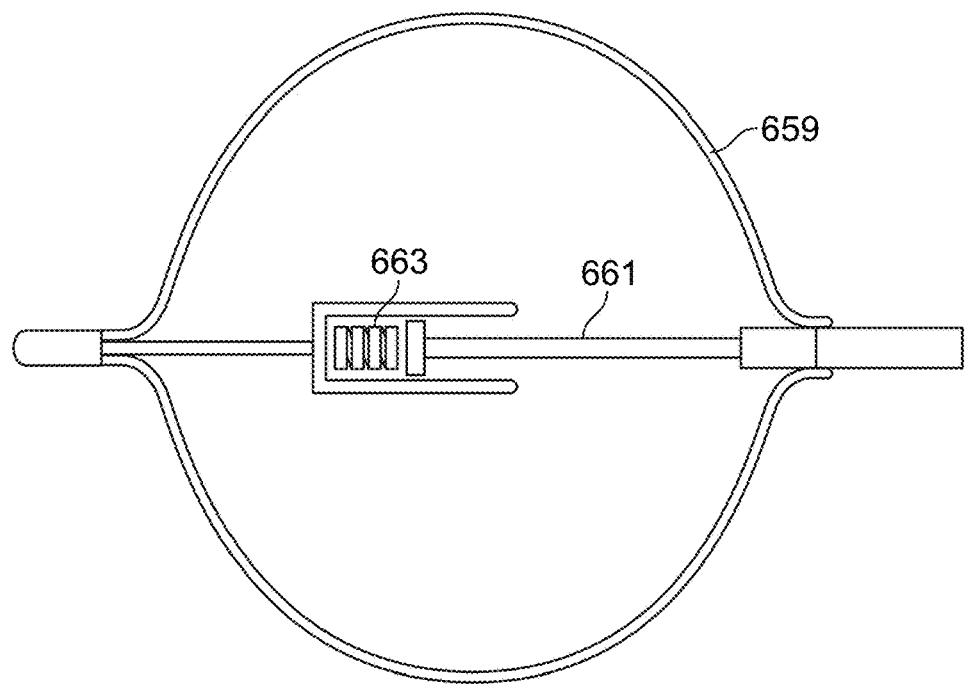

The dilator can also be (See FIGS. 6O-P) a balloon 659 that is distally attached to a sliding structure 661 that is biased in the distal direction to pull the balloon flat when it is not actively being inflated. In one particular approach, a spring 663 is provided in a center member of the balloon 659, the spring 663 being configured to be compressed to shorten a longitudinal length of the balloon 659. The spring 663 can be positioned within a longitudinal length of the balloon or just proximal thereto. In this arrangement, a non-compliant or mostly non-compliant balloon can be caused to expand greater than its set shape, one goal being providing a force balance such that the balloon can be placed at its target formed shape at a particular pressure, and then be transformed with additional pressure to an even more extended shape. This facilitates providing multi-diameter balloons and an overdrive diameter where the user determines that there is a need for additional expansion. Here, the center/crossing member of the balloon 659 is one of the points of constraint to allow a non-compliant balloon to obtain its designed shape at pressure. Where the center of the balloon 659 includes a spring 663 of sufficient stiffness, the balloon 659 can initially reach a designed shaped at a target pressure. If there is a desire for more expansion, pressure to the balloon is increased and instead of the pressure working to stretch the balloon material to increase size, the spring portion of the center member compresses in effect shortening the overall balloon length. This allows the additional pressure to reshape the now shortened balloon to a larger diameter. As pressure is lowered, the spring 663 would be released. This arrangement also facilitates allowing for a larger recoverable range of balloon sizes, beyond that which compliance alone provides. Also, other approaches to providing this functionality involve including a proximal mounting point of the balloon being configured to translate and be constrained via a spring, or a springless embodiment can be employed where a center member is positionally in two lengths with the user controlling which is used.

Figure 6Q:
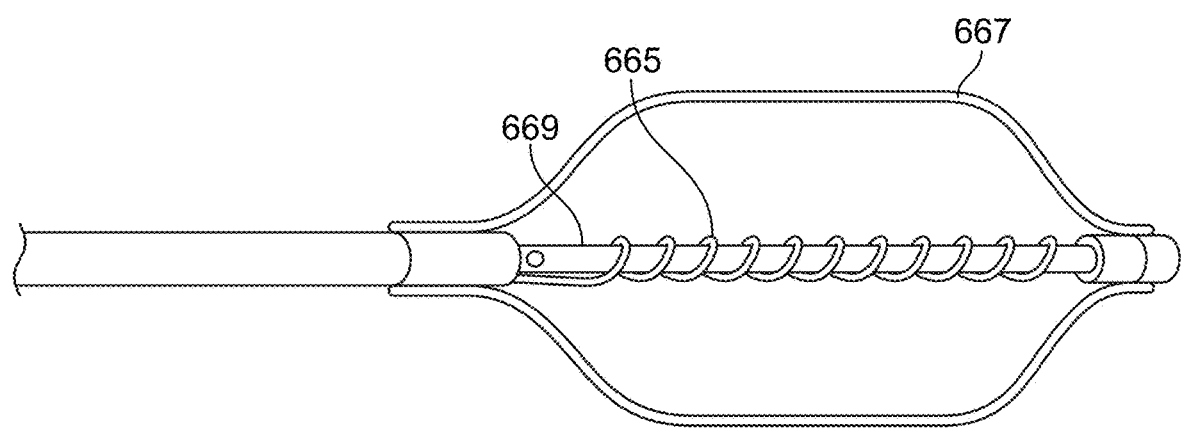

In yet another approach (FIG. 6Q), the dilator 665 can include an element 667 configured along a central shaft 669. The element 667 can be formed by a Nichrome wire to resistively heat fluid employed to expand the dilator or balloon 665. Thermistors or thermocouples can be positioned along the shaft 669 to facilitate temperature control. The element 667 can alternatively function as a heat exchanger thus being a cooling circuit. Lower energies would be associated with heating or cooling the small volume of fluid contained by a dilator. Alternative approaches to heated or cooled dilators can rely on heated or cooled (e.g. saline solution) fluids employed to expand the dilator. Cooling or heating of the balloon could aid in therapy delivery in several ways. In the case of heating, the application of lower level heating works to loosen collagen and increase its flexibility. When combined with balloon inflation this makes the restructure of the bands that are causing cellulite easier and lowers the required forces needed for the balloon to exert. The application of higher heat shrinks collagen and a combination of balloon disruption with heat allows some element of skin laxity that may be present to be addressed, in effect tightening the tissue. Cold or cooling also works to limit the flexibility of any septa or bands such that forces applied to them by the balloon would be lost less in stretch and work more directly on disruption. In another embodiment, the cooling temperature could be controlled to encourage cryolyposis. While fat loss is not necessarily needed when treating cellulite, it may help in the overall healing process and allow for faster remodeling of the area post procedure.

Figure 6R:
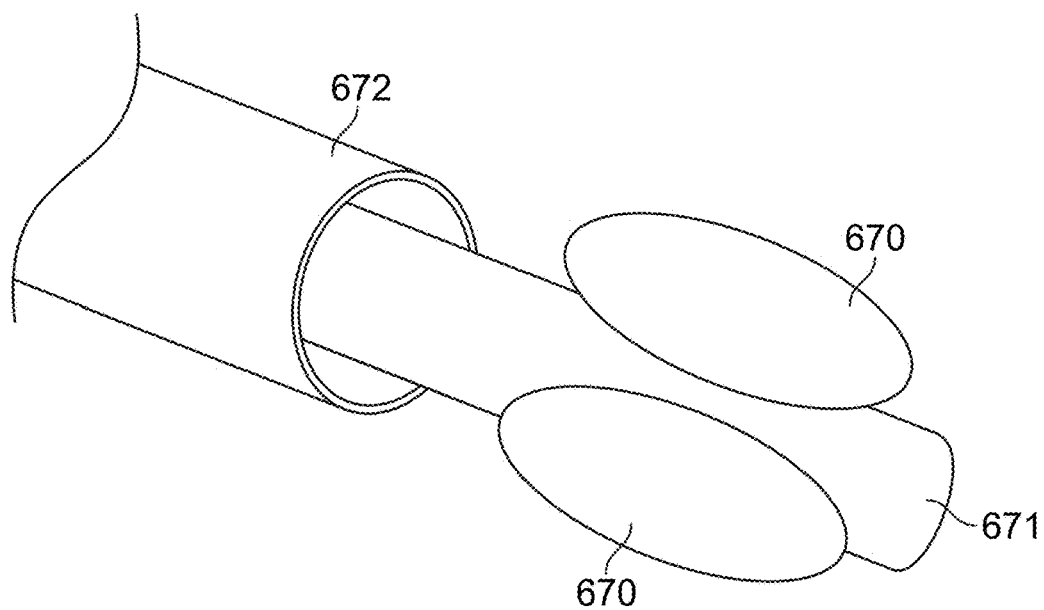
Figure 6S:
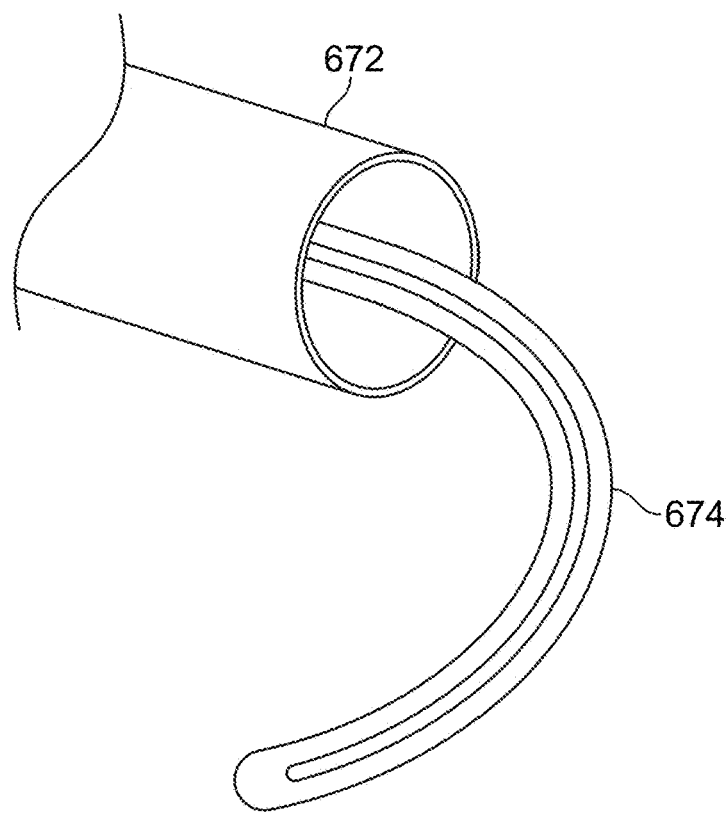

With reference to FIGS. 6R-S, there is shown a treatment device including double balloon 670 structure arranged to disrupt, stretch or rupture septa. In this approach, the balloons 670 are attached to an elongate member 671 such as a tube and the elongate member 671 is both translatable and rotationally received in a sheath 672. Thus, the balloons 670 are positionable as desired relative to septa such as rotationally oriented before deployment and/or expansion, and then preferentially expanded in a direction most likely to accomplish disrupting, stretching or rupturing septa. The device can be deployed over a guidewire. Moreover, as shown in FIG. 6S, a curved or deflectable member 674 can be provided as a support for the balloons 670 (balloons not shown in FIG. 6S). A single balloon can also be employed. In this way, further control over the proper orientation and placement of the balloons 670 is possible, and the balloon or balloons can be configured or be placed about and around target septa. In one aspect, the structure of the balloon encircles target septa. Further in certain approaches, a toroidal shaped balloon is presented about septa. In another additional or alternative aspect, the treatment ensures tensioning septa without movement to a lower tension location away from the treating balloon.

Figure 6T:
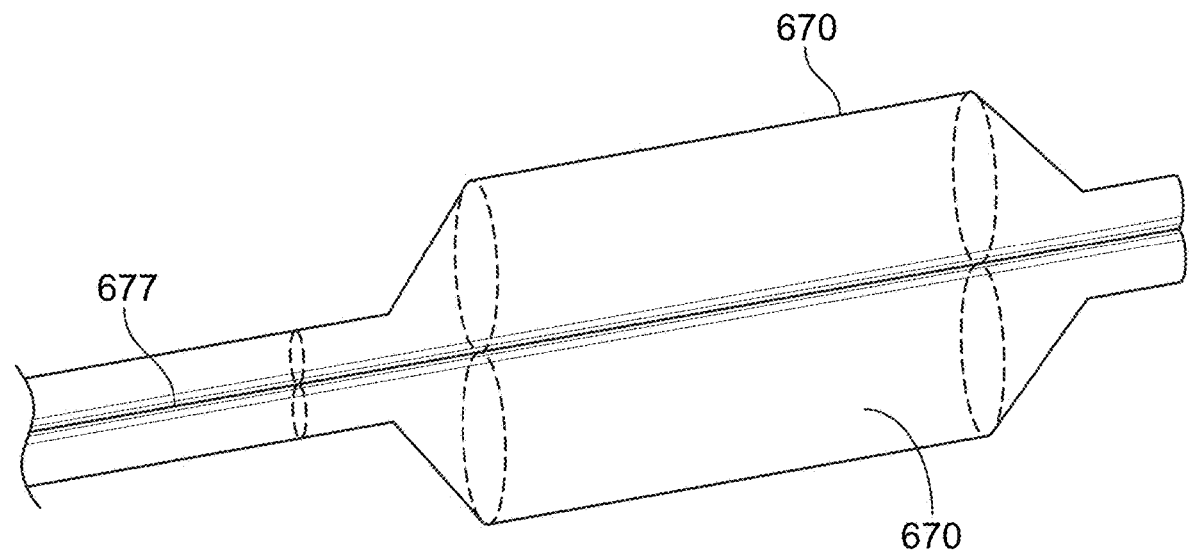
Figure 6U:
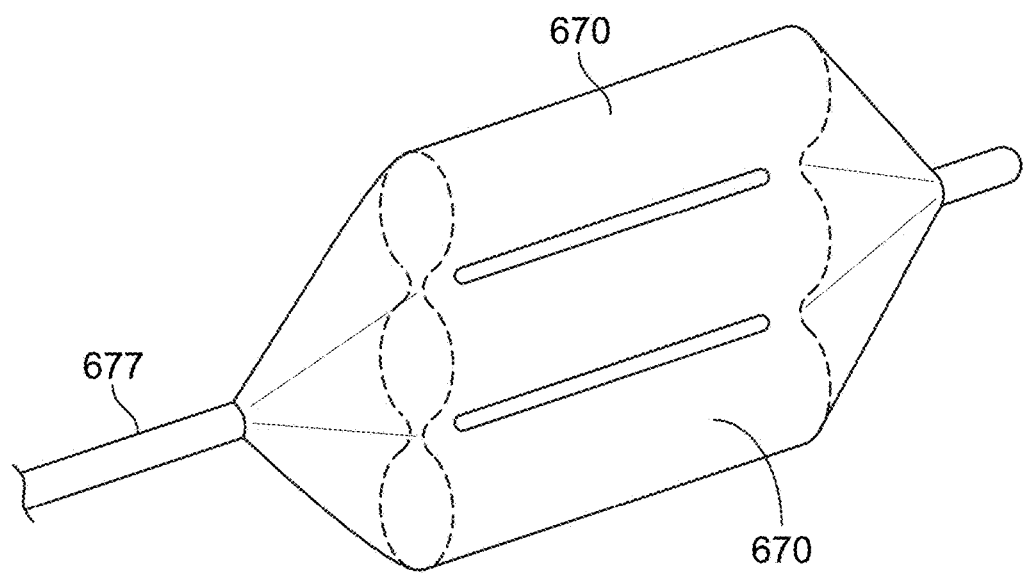

In further alternative or additional aspects (See FIG. 6T), in place of a member 677 that supports and crosses the balloon 670 being concentric and centered, it would be offset flush to one side or the other. This can be then repeated in a mirror image fashion to define balloon structure 670 on an opposite side of the member 677. In various additional or alternative aspects, a balloon can be larger or differently shaped in one direction than the other either dimensionally, through inflation or from different materials, which may be a benefit if there is a need to reduce the overall volume of the balloon for an extensive spreading or expanding. In a particular embodiment, a single lumen version assembly includes a larger balloon with one or more welded areas that would restrict expansion in one axis (See FIG. 6U).

Figure 7A:
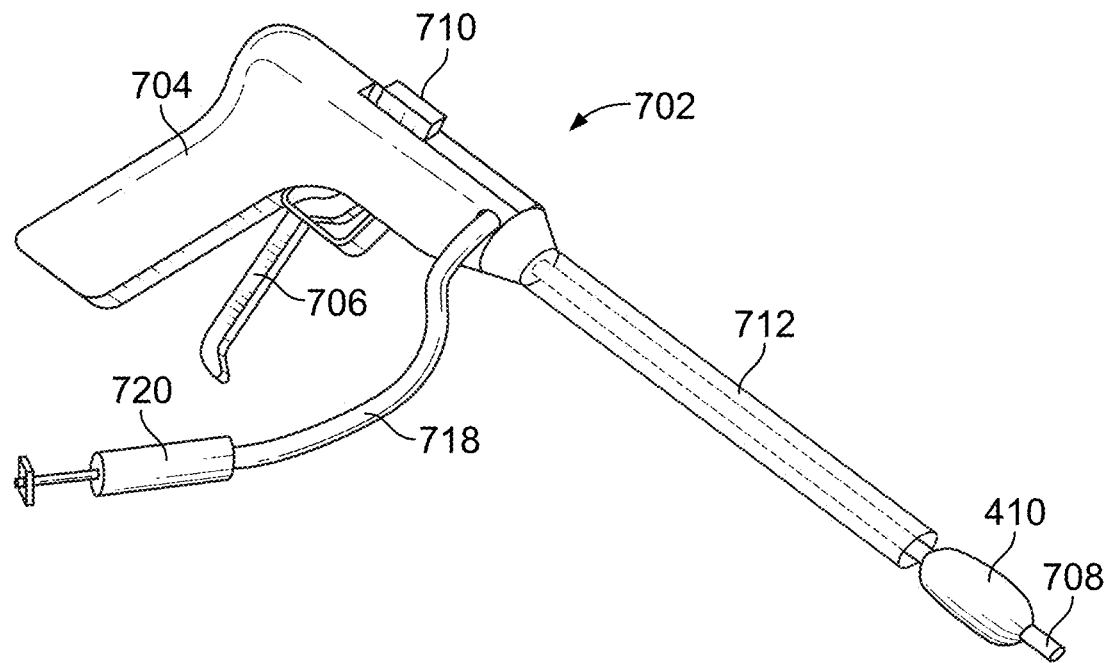
FIGS. 7A-J are perspective views, depicting another embodiment of a cellulite treatment system.
Figure 7B:
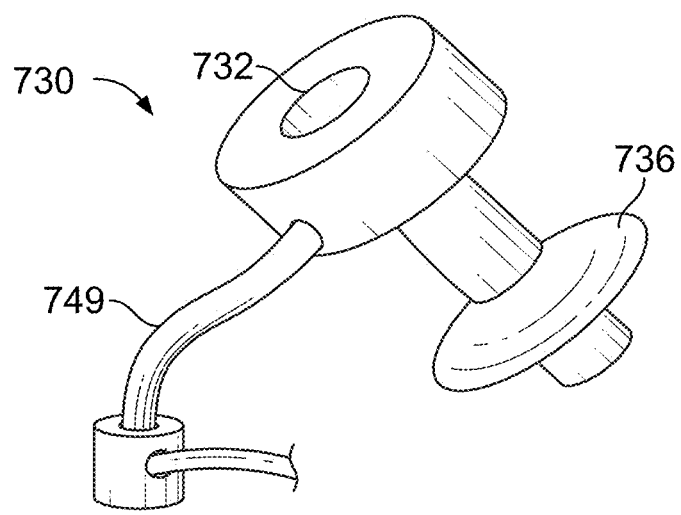
Figure 7C:
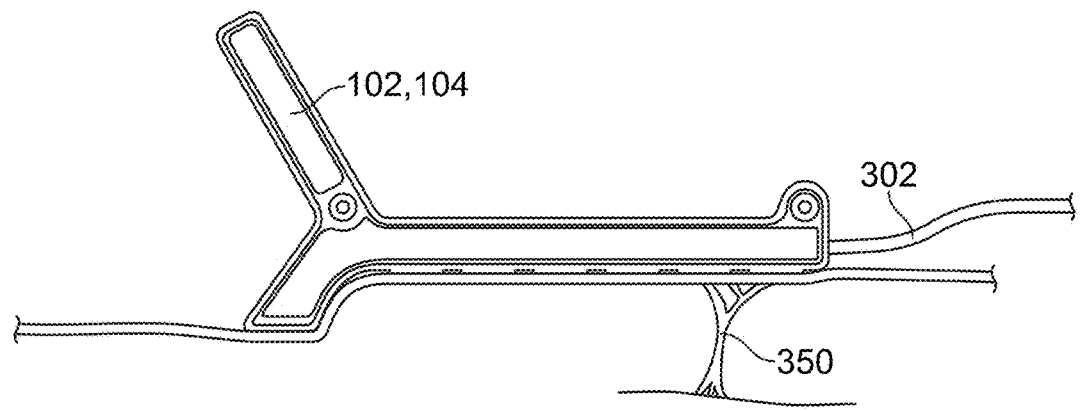
Figure 7D:
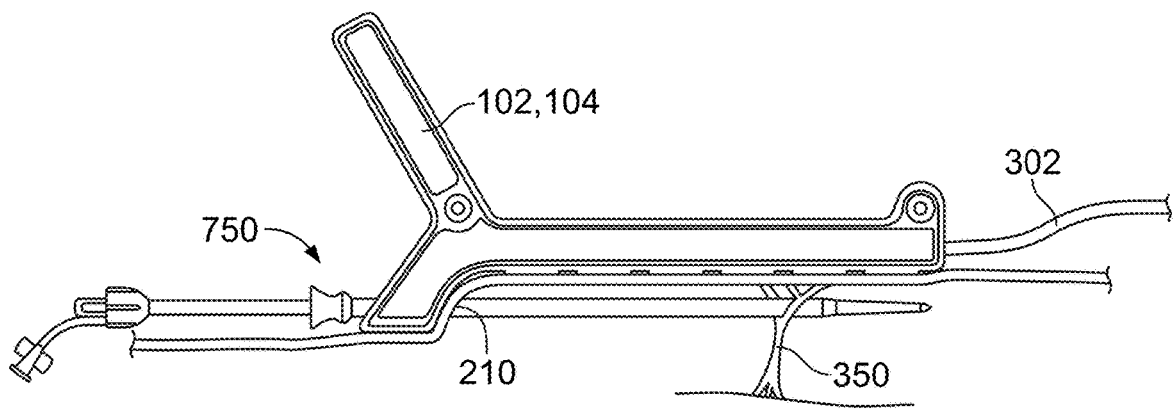
Figure 7E:
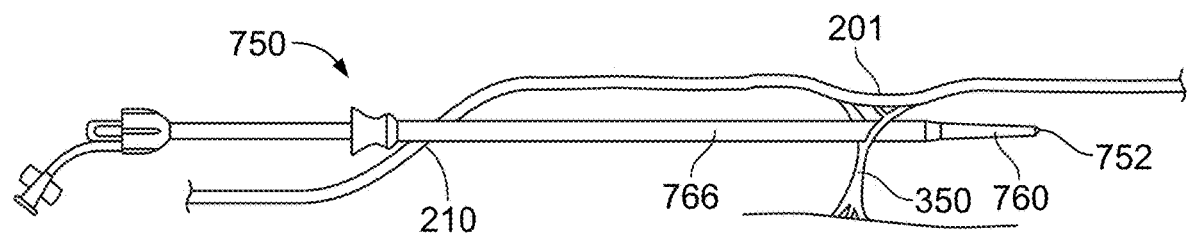
Figure 7F:
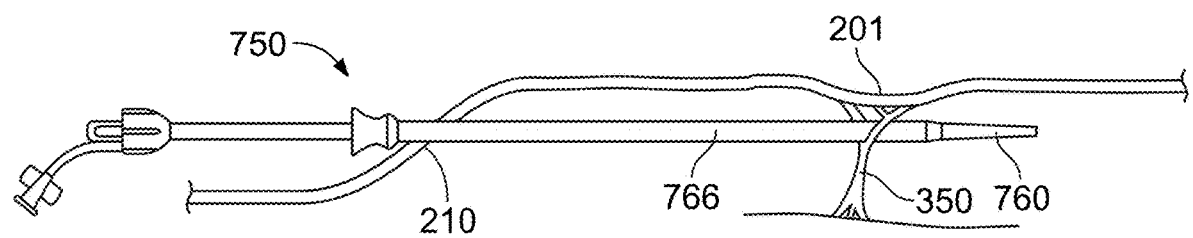

Turning now to FIGS. 7A-B, the various components of the present disclosure can be combined into a cellulite treatment assembly 702 that facilitates ease of use. Such a device is placed within the previously described introducer or other port (FIG. 7B) gaining access to the subcutaneous site. For example, as shown in FIG. 7A, the treatment assembly 702 includes a handle 704 sized and shaped to conveniently fit in an operator's hand. A lever 706 is rotatable attached to the handle 704 and is configured to control expansion and contraction of an expandable dilator 410. Notably, where the dilator is a balloon, the device can have an integrated fluid contained in the handle that expands the balloon upon lever retraction and deflates the balloon upon lever advancement, and further, the device can have a pressure gauge to show pressure within the balloon. Alternatively, the device can be connected by tubing to an external fluid source. Here, the expandable dilator 410 is mounted on a needle 708 and is presented as a single piece. A sliding control lever 710 is also provided on the handle 704 and is configured to control the advancement and retraction of a sheath 712 which is positionable over the dilator 410. Thus, manipulation of the sheath 712 allows for both releasing and recapturing the expandable dilator 410 as well as controls the expansion of the dilator 410.

Also provided is structure for delivering anesthetics or medicines to or within an interventional site. In one embodiment, a tube 718 is attached to the handle 704 and placed in fluid communication with a distal portion of the needle 708. The fluid to be delivered to through the needle 708 is attached via a plunger 720 or other means to a proximal end of the tube 718 and is conveniently arranged so that an operator can deliver the fluid as needed or desired. Additionally, an alternative introducer port 730 can be provided for maintaining access to the interventional site (FIG. 7B). Such a port 730 includes a through channel 732 sized and shaped to receive interventional instrumentation. A distal terminal end of the port 730 is equipped with an expandable member 736 such as a balloon which is configured to secure the port 730 at an insertion site. Moreover, a tube assembly 740 is additionally provided to enable fluids such as medicine to be infused through the insertion site. A stopcock is additionally provided to such control infusion.

Figure 7G:
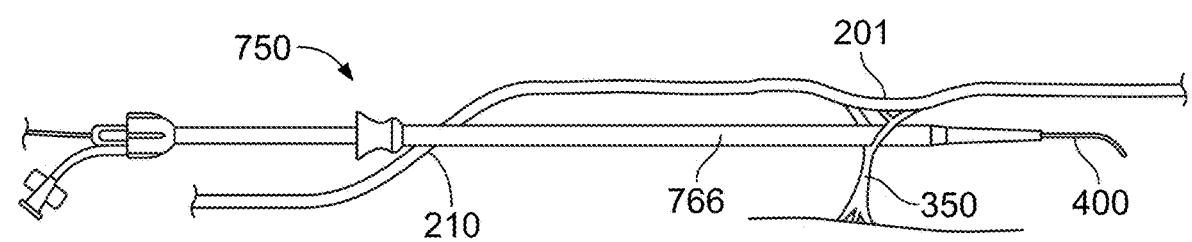

Referring now to FIGS. 7C-J, in one particular approach, the interventional tool 750 is embodied in a balloon attached to a shaft. In one or more embodiments, there is provided an integrated tool additionally or alternatively including a dual lumen stiff shaft with one lumen for a trocar tipped obturator 752 and the other lumen an inflation lumen for the expandable member 410. The integrated tool 750 is preferably 18 French in outer diameter, more preferably 16 French or less, so that the insertion site 210 does not require a stitch or stitches to be closed and can be closed with an adhesive or adhesive bandage. The expandable member 410 may be different sizes between about 10 mm to about 30 mm in diameter and about 20 mm to about 100 mm in length. At the distal end of the shaft is a long tapered tip 760 with a shallow angle taper that allows the tool to be pushed through the tissue more easily. Behind the tapered tip initially in a folded profile that is equal to or smaller than the diameter of the proximal end of the tapered tip is an expandable member 410 mounted on the dual lumen shaft. There is an integrated sheath 766 that is initially over the expandable member 410 and forms a continuous taper to the proximal end of the tapered tip 760. The suction, compression, or adhesive stabilizer 102, 104 is used while the tool is inserted to the farthest treatment location along the previously mapped treatment path (See FIGS. 3B and 7C-D). Once the expandable member 410 has been inserted to the desired location, the suction or adhesive stabilizer is removed (FIG. 7E) and the trocar tipped obturator is either removed as shown FIG. 7F, or it can be just pulled back inside the long tapered tip for safety. If it is removed, optionally, a guidewire 400 can be placed through its lumen and extended out of the distal end of the shaft (FIG. 7G). In an alternative embodiment, the interventional tool has a third lumen such that the trocar tipped obturator is pulled back inside the long tapered tip and the guidewire is placed through the third lumen and extended out of the distal end of the shaft. The guidewire can be used in order to put a larger expandable member tool back in if the initial size chosen did not create the desired result.

Figure 7H:
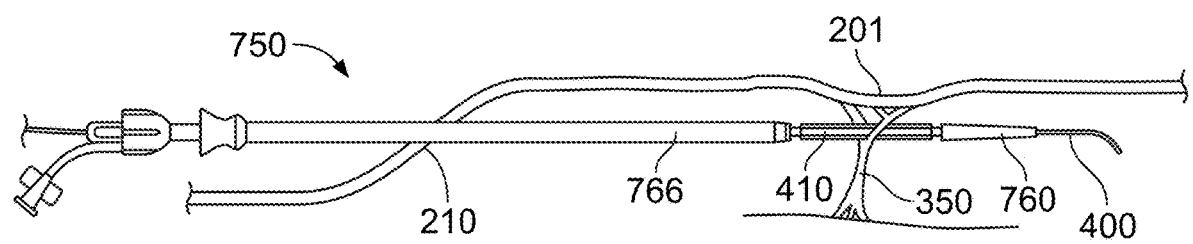
Figure 7I:
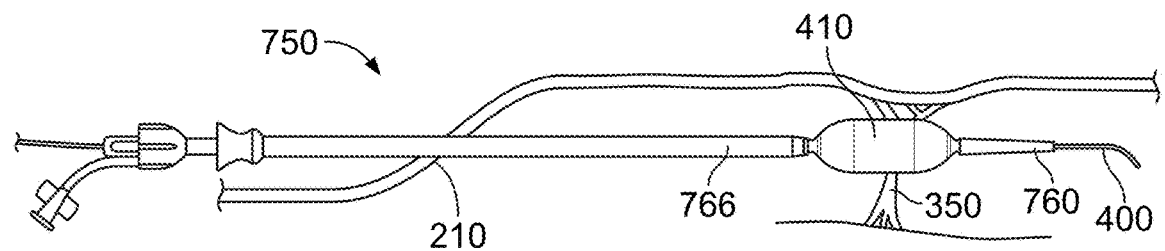
Figure 7J:
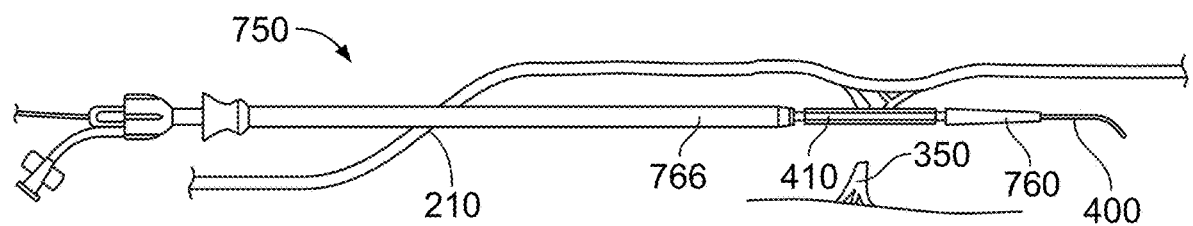

To treat the septae, the integrated sheath 766 is slid proximally to uncover the expandable member 410 (FIG. 7H). The expandable member 410 is inflated/deflated or expanded/compressed (FIGS. 7I-J). The sheath 766 is then advanced back over the deflated expandable member 410 and the entire tool is pulled back to the next most distal treatment location along the previously mapped treatment path. Thereafter, the procedure is repeated and as such the sheath is slid proximally, the expandable member is inflated/deflated, the sheath is advanced back over the deflated expandable member. Next, the entire tool is pulled back to next treatment location, the steps repeated until the previously mapped treatment path has been completed. Then the tool is pulled back to the skin opening and the procedure is repeated along the next previously mapped treatment path. As noted above, the location and performance of the expandable member along the treatment paths can be identified through: palpation: transillumination built into the tool or in a guidewire or on the end of an illuminated obturator; ultrasound imaging or visualization through the skin; fluoroscopically; or magnetically.

Figure 8A:
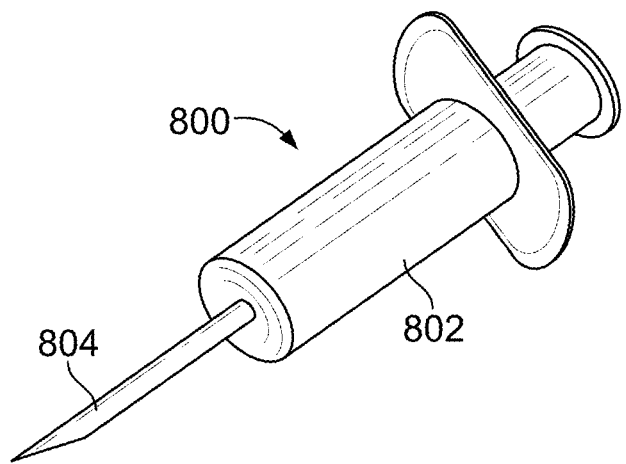
FIGS. 8A-K are perspective views, depicting components of a spot treatment system.
Figure 8B:
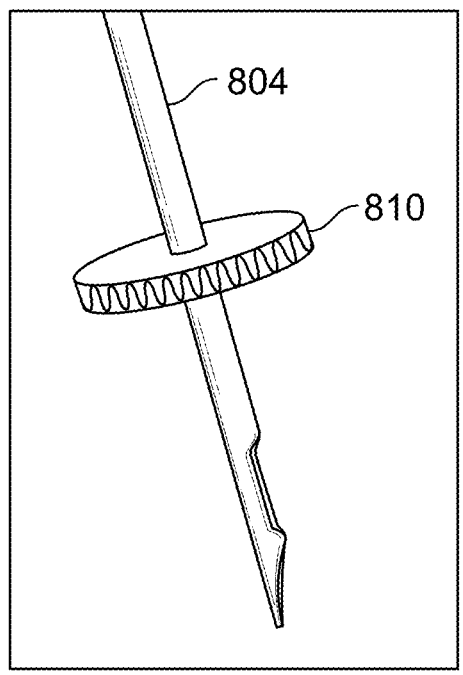
Figure 8C:
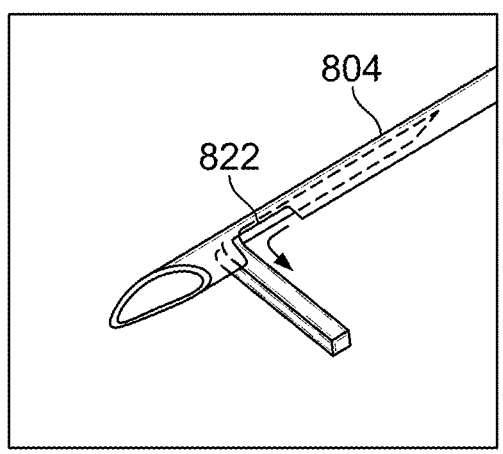

In an alternative embodiment, spot treatment of septa is possible employing a cellulite treatment system 800 configured to address one interventional site at a time. Such approaches can employ one or more of the disclosed stabilizers or introducer structures, or the treatment systems can lack one or more of such structures. Thus, cutting structures can be inserted perpendicular to skin to accomplish treatment or can be advanced below the skin in a direction generally parallel to the surface of the skin or angles with respect thereto. Moreover, the structures of disclosed guidewires can alternatively or additionally be configured to define cutting structures. In one particular aspect, the cutting action is rotary in character, such that the cutter spins with controlled speeds configured to cut septa in a manner dictated by observed septa structure at the interventional site. The cutter is alternatively or additionally configured to accomplish cutting action by engaging or dragging the cutter against target septa. Again, here, the degree to which the dragging is performed is dictated by the septa and septa inherent structure. In one approach, a system 800 includes an elongate handle 802 that is provided for grasping by an operator (See FIGS. 8A-C). Extending longitudinally from the handle 802 is a needle assembly 804. The needle 804 is configured to create an insertion site adjacent a specific cellulite target area, or directly into a dimple cellulite site. Further, it is through the needle assembly 804 that interventional site instrumentation is advanced to address and treat septa residing below a dimple expression on a subject's skin. For example, any of the previously described dilators can be employed to treat septa. Additionally, in a slightly more traumatic embodiment, the dilator can be replaced with or additionally include or cooperate with a harmonic scalpel, selective cautery structure or energy transmitting structure for dissecting tissue and/or controlling bleeding. In one approach, once a correct depth is accessed, a cutting instrument is swept 360 degrees to cut surrounding septa. Additionally or alternatively, an endoscope can be employed in an assembly including a cutter to sever septa in a targeted manner. That is, septa that are viewed by the endoscope are targeted for severing by the cutter. Here, direct visual confirmation of a treatment is provided.

In one embodiment, the needle 804 can be fashioned with a stop 810 that is positionable along the needle 804 as desired or dictated by a particular procedure or anatomy. The stop 810 is located so that when the needle 804 is placed within tissue, its terminal end is positioned at a desired depth such as between tissue layers connected by septa. A side opening 822 is further provided at the terminal end of the needle 804. It is through this side opening 822 that interventional devices such as dilators, scalpels, cautery structure or energy transmitting devices are advanced between tissue layers. Such devices are then employed to selectively treat the septa residing below the skin for the purpose of eliminating or reducing the appearance of cellulite. Once it is determined that the treatment has been successful, the spot cellulite treatment system 800 is then removed and employed at another location exhibiting cellulite.

Figure 8D:
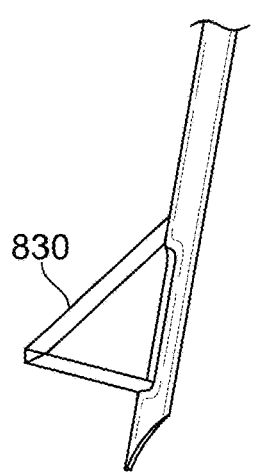
Figure 8E:
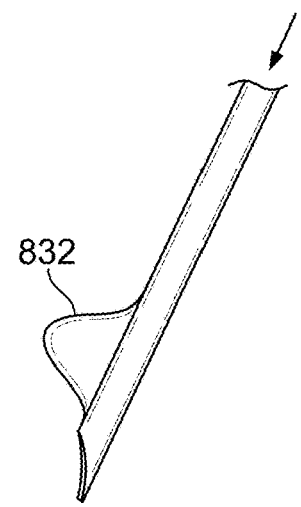
Figure 8F:
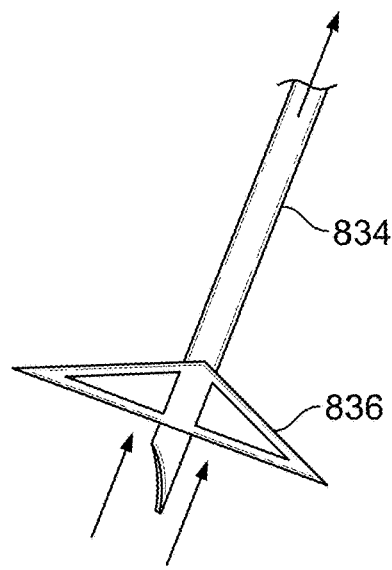
Figure 8G:
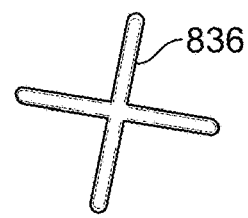
Figure 8H:
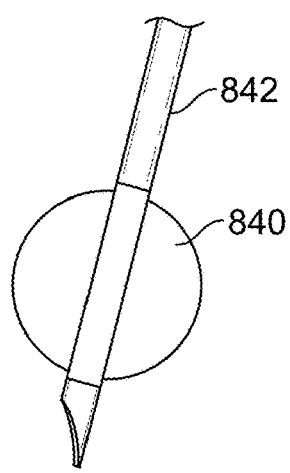
Figure 8I:
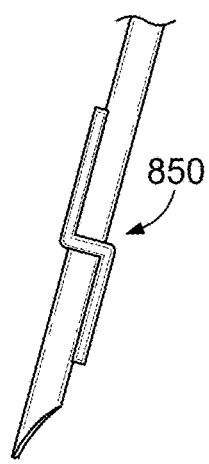
Figure 8J:
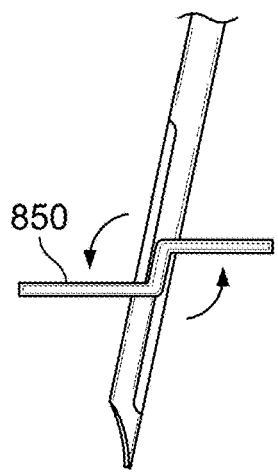

Turning now to FIGS. 8D-J, there are shown further aspects of tools employed for spot treatment of cellulite in alternative approaches. With reference to FIG. 8D, a spot treatment device can be equipped with a wire that includes linkages 830 manipulation of which function to push out a cutting blade arrangement that is sized and shaped to cut connective tissue. As shown in FIG. 8E, a distal end portion of a spot treatment device can be equipped with a wire arranged to be advanceable to define a loop 832, the loop having a gauge facilitating the structure to be employed to cut tissue in a non-atraumatic treatment approach. Alternatively, RF energy can be employed to cut septa. FIGS. 8F-G depicts a deformable hypotube 834 that is expandable such that two or more arms 836 project to define blades for cutting in another non-atraumatic approach to treatment. FIG. 8H illustrates a balloon structure 840 attached to a needle hypotube 842 which can be expanded below a dimple to eliminate or reduce the appearance of cellulite. Finally, in another non-atraumatic approach (FIG. 8I-J), a distal end portion of a spot treatment device can be fashioned with blades 850, one to cut for deployment and at least one that is configured to rotate and cut connective tissue.

Figure 8K:
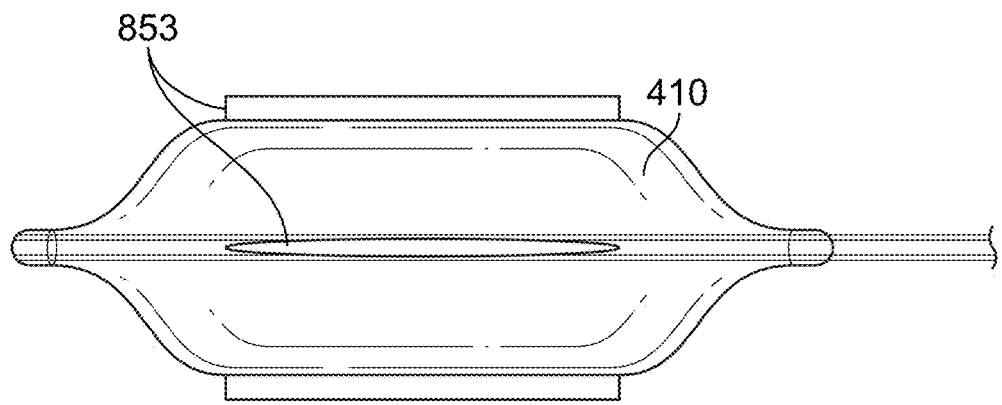
Figure 8L:
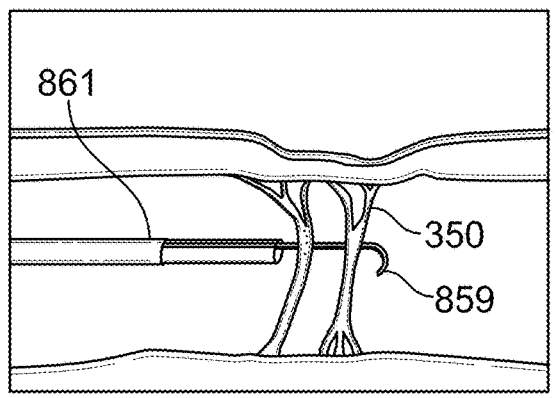
FIGS. 8L-O are cross-sectional views, depicting treatment involving a lasso.
Figure 8M:
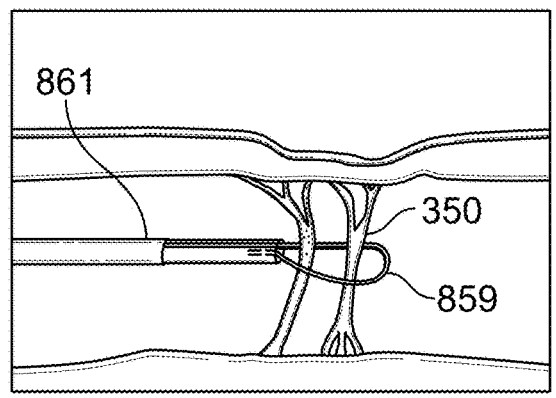
Figure 8N:
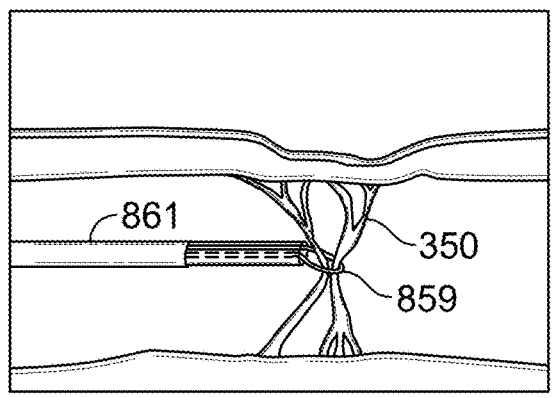
Figure 8O:
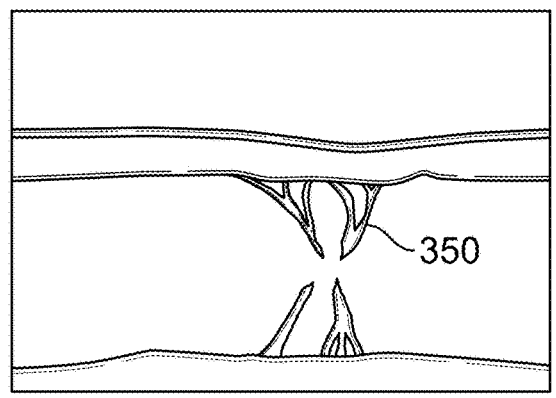

As shown in FIG. 8K, a dilator 410 can additionally be equipped with longitudinally extending blades 853 that are deployed when the dilator 410 is expanded. The blades 853 are configured to engage and cut target tissue or septa in an alternative approach to treatment. Such cutting is employed in an alternative to a non-traumatic approach and accomplished by rotating or otherwise advancing, sweeping or retracting the dilator 410. The assembly is unexpanded and withdrawn from the interventional site after use such as through a tube.

In yet another treatment approach, a curved wire forming a lasso 859 attached to a shaft 861 (FIGS. 8L-O) can be deployed about septa 350 within a target zone 861. Pulling the lasso 859 to reduce the perimeter it defines results in cutting septa 350 and treating cellulite. In one aspect, the lasso is formed from nitinol wire, or is pre-formed wire or pieces thereof. The lasso 859 encircles targeted septa and via tightening, cuts the septa. One approach involves cutting a targeted area without shaft movement thus providing a controlled approach to treatment.

Figure 9A:
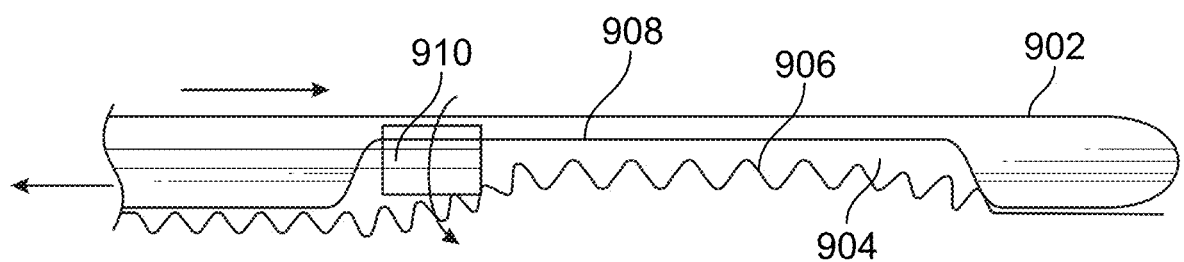
FIG. 9A-B are cross-sectional views, depicting an atherectomy device and use thereof.
Figure 9B:
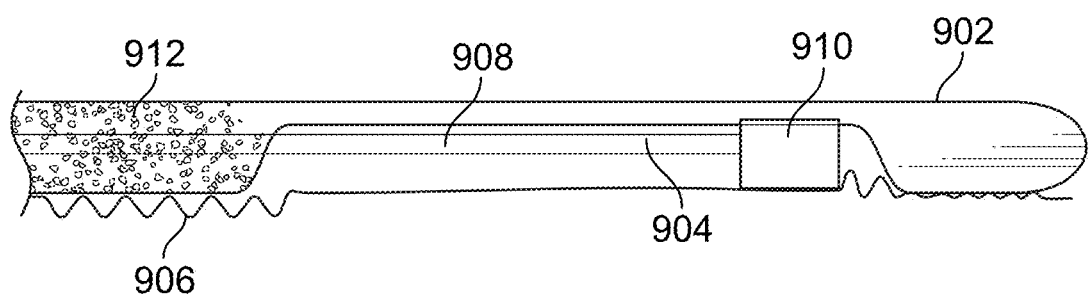

An atherectomy-style cutter 902 (See FIGS. 9A-B) can be configured to remove tissue through an opening 904 on the side of the instrument, can be used in certain ancillary, more traumatic approaches to treatment. Cutting structure 906 is attached to an elongate actuator 908 via a block or other connection 910. Manipulation of the actuator 908 causes the cutting structure 906 to engage targeted tissue. A lumen 912 is further provided as a conduit for applying a suction force to the interventional site so that severed or macerated tissue 912 can be removed. This device can be employed to harvest fat for subsequent placement at a site that has been treated with a dilator and used to fill the space created. The cutter 902 can also be employed as a primary treatment device for cutting septa to treat cellulite.

With reference again to FIGS. 4A-C, it is to be recognized that the expandable dilator approach to creating spaces subcutaneously have applications beyond treating cellulite. That is, manipulating connective tissue such as septa can be applied to various other conditions or maladies. For example, the disclosed dilators are employed for body sculpting, eliminating wrinkles, treating acne scars, and/or lifting and repositioning skin. Foam fillers or stents or spacers of varying lengths and other structures such as subcutaneous attachment structures that are absorbable or permanent are used to accomplish such objectives. Further, a diode laser can be used under the skin to tighten the skin in target areas. In this way, skin can be smoothed over to remove unwanted creases, scars, wrinkles or stretch marks. Moreover, spaces created by dilation can be filled with materials, for example the patient's own fat harvested from another location or an expandable spacer constrained in a sheath can be released in the space created by dilation, to provide a more youthful appearance or desired resilience. Also, employing the spaces created by dilation, subcutaneous structures can be moved, translated, anchored or pulled (such as with a barbed suture) to create a desired outward appearance. These and other approaches to subcutaneous tissue treatments therefore form part of the present disclosure.

Various approaches and apparatus can be employed to expand and contract dilators or balloons used in cellulite treatment systems. Many require two handed operation and in many cases are operated by an assistant or additional person. In the case of a cellulite procedure, the practitioner does not have regular contact with balloon inflators and may need to accomplish the inflation on their own with a single hand. Additionally, conventional balloon inflators are designed for high pressure levels and are designed to allow the user to slowly approach the desired target pressure. Present inflators are typically designed to be a more universal tool to be inflate different types of balloons to different pressures. There is a desire with a cellulite procedure to streamline this process for both the training of the practitioner new to the procedure as well as enabling faster, precise inflation during a procedure. An additional benefit of a syringe based system is that current inflators are more geared towards an operating room with a patient unaware of their surroundings so appearance is very functional and imparts a medical procedure "feel". The cellulite patient will likely be aware during the procedure and all tools should appear either like other equipment they encounter in a similar environment or deemphasis the medical nature of the procedure to aid in patient comfort. Unlike standard inflators, a cellulite practitioner will have experience with syringes. Additionally, lower balloon pressures allow a more direct inflation method as mechanical advantage is not needed.

In one approach (FIG. 10A), a standard control syringe and a series of one-way valves are provided to allow the syringe (of any size) to be used. A syringe 930 is drawn back and saline is pulled from a reservoir 931 through a one-way valve 932. The syringe 930 is next depressed which pushes saline forward through a second one-way valve 933 into a balloon 934. A first one way valve 932 prevents the saline from the syringe 930 returning to the reservoir 931. The syringe 930 can be drawn back and filled from the reservoir 931, and pushed forward into the balloon 934 where the balloon 934 has a volume greater than the syringe 930, the one-way valve 933 preventing any backflow while the syringe is reloaded with saline from the reservoir 931. As the balloon 934 approaches target pressure which can be monitored on the pressure gauge 938, it will get to a point where an optional pop off valve 939 engages at a target inflation pressure. This pop off valve 939 will keep the balloon 934 at target pressure. In the event the user still advances the syringe 930 to inflate, over flow will be redirected back to the reservoir 931 while maintaining target pressure. Here, the syringe 930 stroke is smooth (unlike the rotary motion of the standard inflator) but as septa in cellulite targets rupture there is a change in pressure in the balloon as the septal structure break. This change maybe sensed by the user in the syringe 930 giving tactile feedback during treatment. To deflate the balloon 934, one or more stop cocks or valves 940 are turned to reverse the original path. As the syringe 930 is drawn back it pulls saline from the balloon 934 and when advanced it pushes the saline back in the reservoir 931. This is repeated until the balloon 934 is deflated. The saline in the system is closed so that the field is as dry as possible and there is no residual saline in the area of treatment. It is also noted that, the smaller the syringe used the more pumps required but the higher pressure can be obtained with the same user input force. The reservoir 931 could also be a prefilled syringe or a saline bag.

Figure 10A:
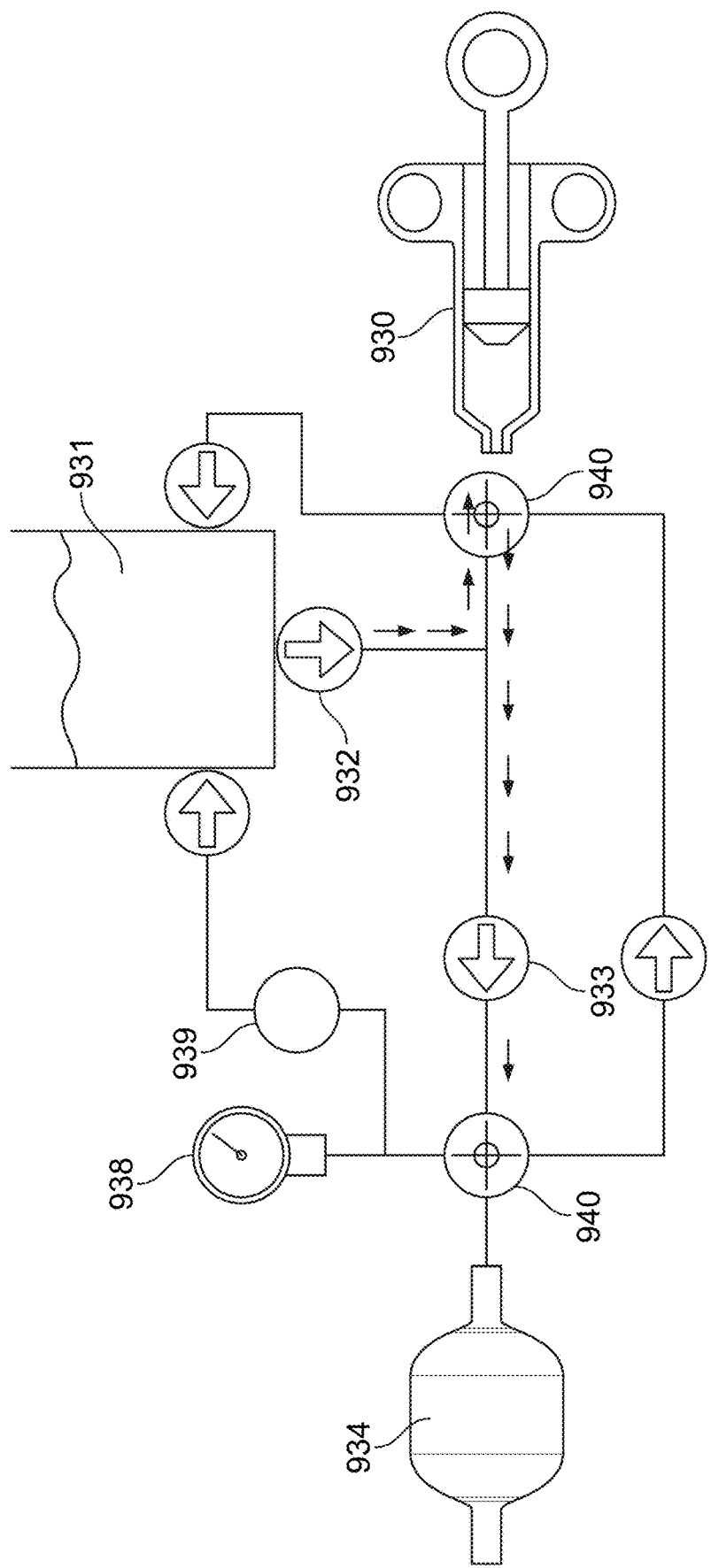
FIG. 10A is a schematic representation, depicting functionality of a pump assist assembly.
Figure 10B:
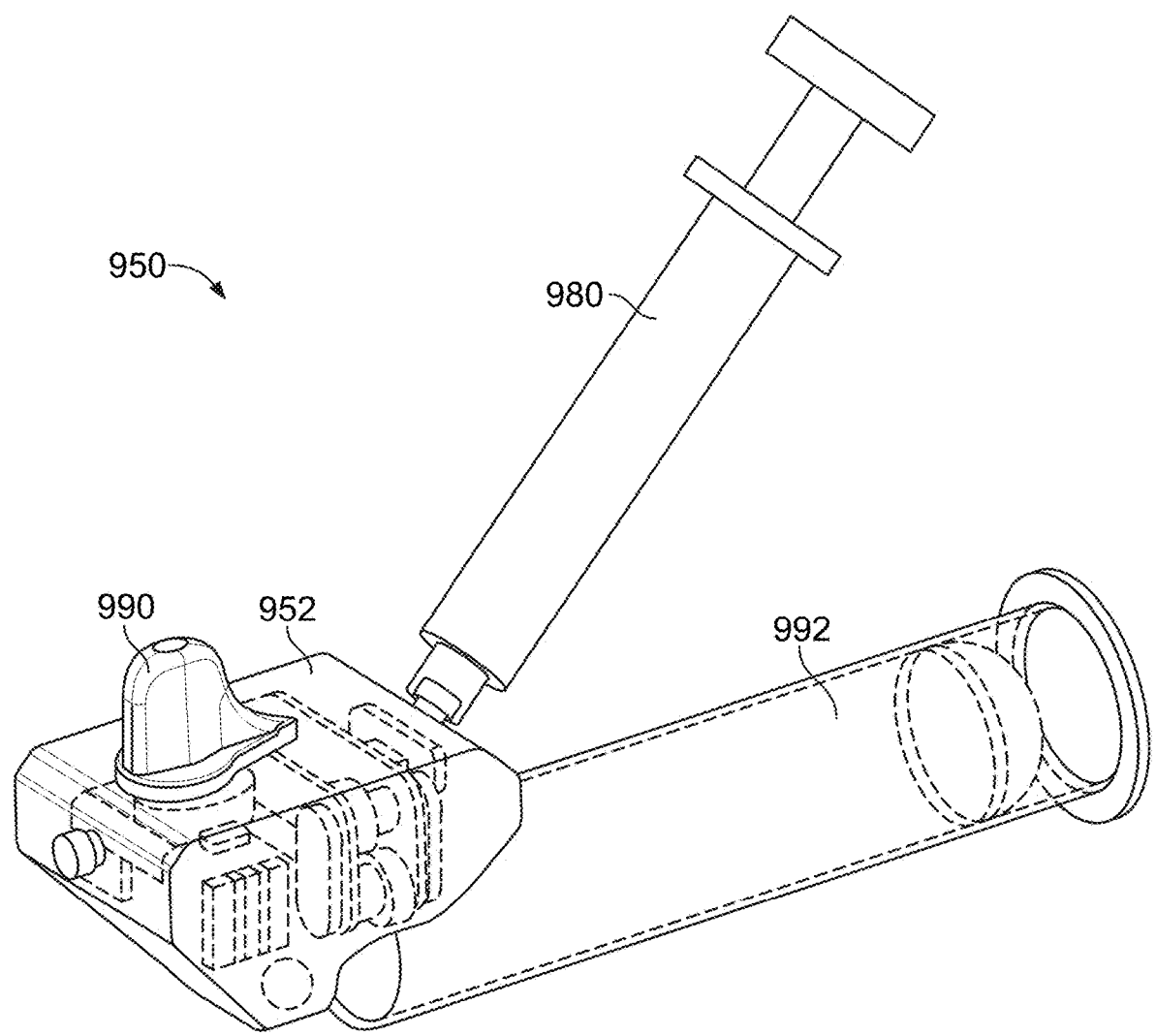
FIG. 10B is a partial cross-sectional view, depicting a rapid pump assist assembly.
Figure 10C:
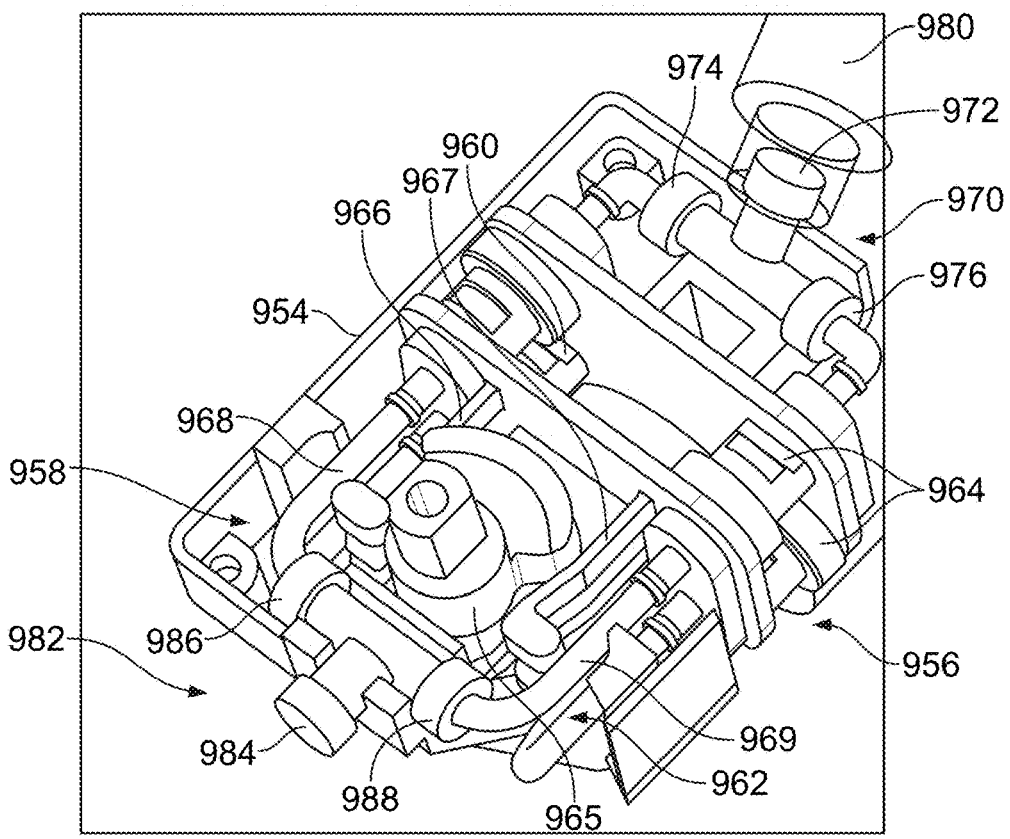
FIG. 10C is an enlarged perspective view, depicting internal structure of the rapid pump assist assembly of FIG. 10A.
Figure 10D:
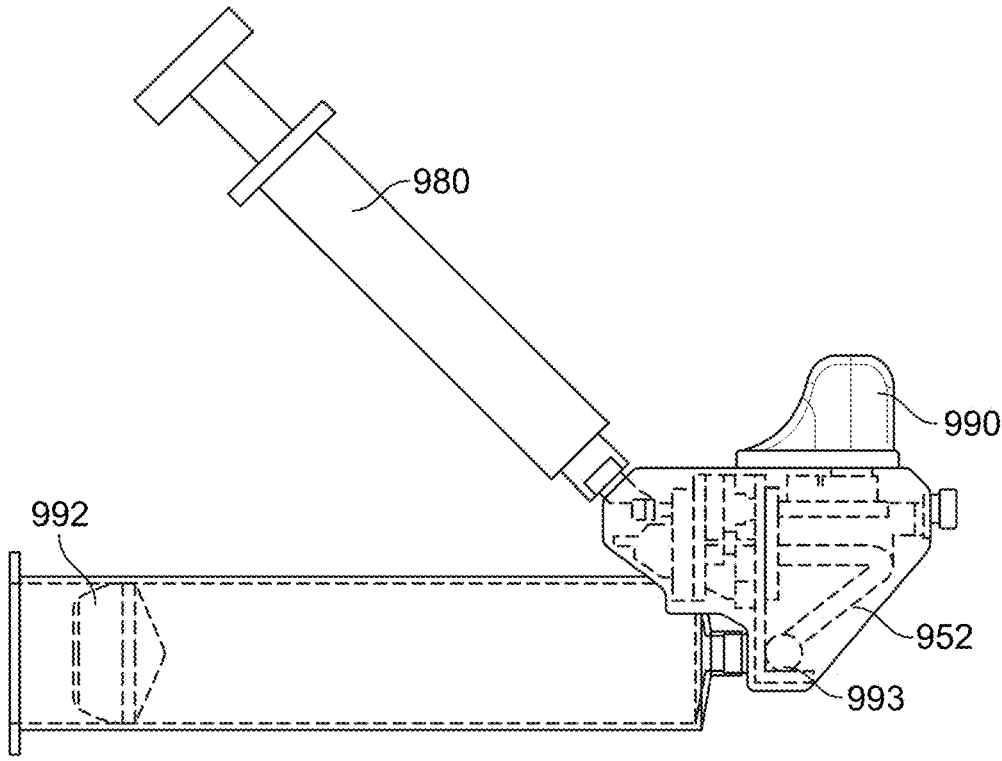
FIG. 10D is a side view, depicting the rapid pump assist assembly of FIG. 10A.
Figure 11A:
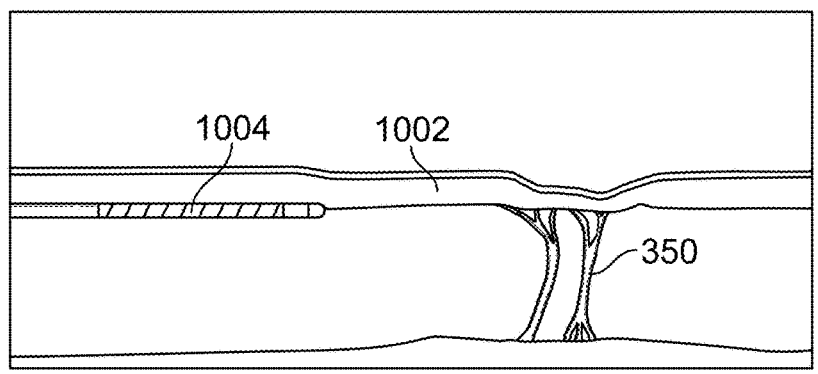
FIGS. 11A-D are partial cross-sectional views, depicting another treatment approach.
Figure 11B:
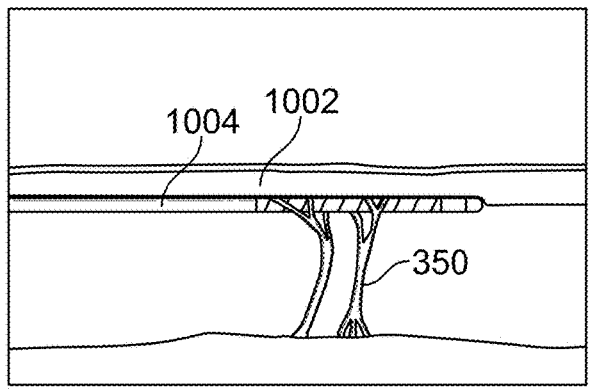
Figure 11C:
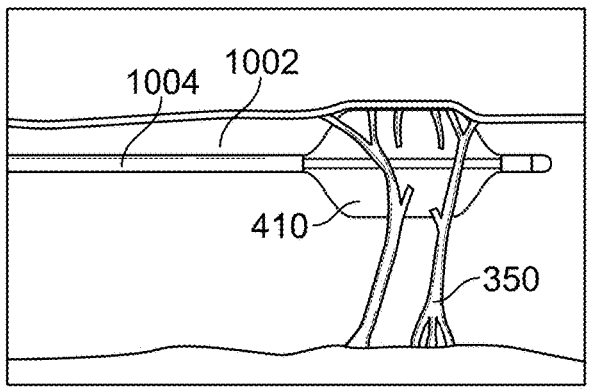
Figure 11D:
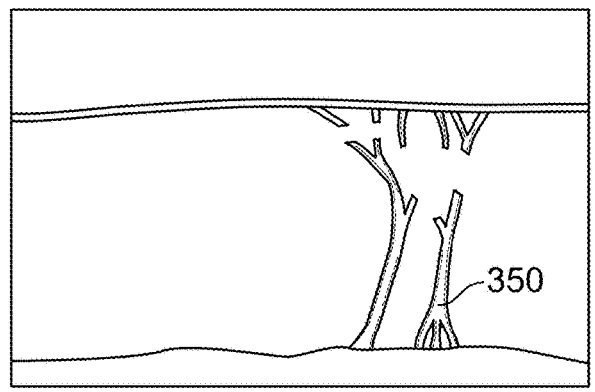

In one aspect, a simple syringe can provide for the expansion and contraction of such members. In another approach, an automated pump can provide the desired expansion and contraction. With reference to FIGS. 10B-D, the expansion and contraction of a balloon or other dilator can be accomplished using a rapid pump assist device 950. The rapid pump assist device 950 includes a housing 952 embodying an inlet assembly 954 and an outlet assembly 956. Two inlet pinch valve assemblies 958 (See FIG. 10B which shows the device with a portion of the housing removed), each connected to a single one-way inlet valve 960 are associated with the inlet 954, and two outlet pinch valve assemblies 962, each connected to a single one-way outlet valve 964 are associated with the outlet 956. Each pinch valve assembly includes a rotation part 965 that is configured to engage first 966 and second 967 arms as it rotates from a first to a second position. When in such positions, the arms 966, 967 are deflected against inlet 968 or outlet 969 tubing to thereby pinch the tubing closed or to allow the tubing to remain open. Connected at one end of the housing 952 is a first T-fitting 970 having a first port 972, a second port 974 and a third port 976, the first port 972 being sized and shaped to connect to a syringe pump 980. The second 974 and third 976 ports are associated with the inlet and outlet functionality, respectively. At an opposite end of the housing 952 is a second T-fitting 982 having first 984, second 986 and third 988 ports, the first port 984 thereof being sized and shaped to mate with a tube in fluid communication with a balloon or other dilator (not shown). The second 986 and third 988 ports of the second T-fitting 982 are in fluid communication with the inlet and outlet, respectively. As seen in FIG. 10A, a knob 990 connects to a rotation part 965 to thereby provide structure for grasping and turning by a user. A reservoir 992 connects to the arrangement via a third fitting 993 (FIG. 10C) and is associated with the inlet 954 and outlet 956 assemblies. Also provided are pressure relief valves (not shown) in fluid communication with the reservoir 992 and the dilator, the relief valves having different cracking pressure ratings so that there is a control of maximum pressures provided by the dilator or balloon.

Balloon inflation or dilator expansion is accomplished with the inlet pinch valves 958 in a passive state, leaving an inlet line 954 open while closing off an outlet line 956 such that the outlet pinch valves 962 are in an active state. Deflation or contraction is achieved by turning the knob 990 to close the inlet line 954 and opening the outlet line 956. Control of inflation or deflation is provided by the actuation of the knob 990. It is noted that in an alternative approach, the one-way valves and pinch valves can be replaced by rotating one-way valves to achieve the desired functionality.

Turning now to FIGS. 11A-D, there is shown another approach to cellulite treatment. Here, crossing the superficial fat space 1002 below the dermis is accomplished with sharp tools or with blunt or tapered dissecting tools 1004. In one aspect, cutting or slicing structure can be attached at the end of an elongate instrument that is sized and shaped to be advanced below the skin to engage and cut septa. In one particular approach, such cutting or slicing structure such as that describe above is configured to be pulled or pushed against connective tissue to accomplish cutting, and the treatment can involve a stabilizer or be achieved without a stabilizer. In another aspect, a blunt tip device or balloon 410 is associated with or attached to the elongate tool, such as near its terminal end portion, and used to track and target cellulite sites without a stabilizer and along the bottom of the dermis. Septa 350 is often characterized by including a tree-like structure and a main trunk of the tensioning septa 350 that creates a cellulite dimple location. With the dermal tracking and the inflation of a balloon 410, this would ensure the optimal depth and positioning, and the user is able to disrupt the direct connection between the branches of the tensioning septa 350 right at the intersection with the dermis. This facilitates allowing for smaller balloons or more targeted/effective therapy.

Accordingly, various approaches to cellulite treatment methods and apparatus are presented. The disclosed approaches are configured to provide an effective and focused approach to treating, minimizing and preventing cellulite. The disclosed approaches can also be used to repair and reduce the appearance of cellulite in a targeted and atraumatic manner. Further, the disclosed proactive treatment modalities are easy and effective to use.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A cellulite treatment method comprising:
   identifying a treatment site where cellulite exists;
   employing an engagement device to provide a stable foundation without pulling tissue into a cavity or recess;
   selecting a depth to be accessed between tissue layers;
   creating an insertion site with a needle;
   advancing the needle in a direction parallel to skin overlying the treatment site;
   after creating an insertion site releasing tissue;
   advancing an expandable dilator within the insertion site to an interventional site using transillumination; and
   expanding the expandable dilator to rupture without cutting at least a septum at the interventional site.

2. The method of claim 1, further comprising creating a treatment regimen involving employing the insertion site to treat multiple areas.

3. The method of claim 1, further comprising advancing a hypotube over the needle.

4. The method of claim 1, further comprising advancing a guidewire within a hypotube.

5. The method of claim 1, further comprising advancing the expandable dilator over a guidewire.

6. The method of claim 1, further comprising manipulating the expandable dilator to stretch or re-orient septa connecting tissue layers.

7. The method of claim 1, further comprising scanning skin of a subject to identify treatment areas and create a treatment regimen, a scanning date being stored so that the efficacy of the cellulite treatment can be assessed.

* * * * *